US008637023B2

(12) United States Patent
Lin et al.

(10) Patent No.: US 8,637,023 B2
(45) Date of Patent: *Jan. 28, 2014

(54) HEMOJUVELIN FUSION PROTEINS

(75) Inventors: Herbert Y. Lin, Watertown, MA (US);
Jodie Babitt, Newton, MA (US);
Raymond T. Chung, Chestnut Hill, MA (US); Tarek A. Samad, Princeton, NJ (US); Alan L. Schneyer, Concord, MA (US); Clifford J. Woolf, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/407,502

(22) Filed: Feb. 28, 2012

(65) Prior Publication Data
US 2012/0258105 A1   Oct. 11, 2012

Related U.S. Application Data

(60) Continuation of application No. 13/171,438, filed on Jun. 28, 2011, now Pat. No. 8,293,236, which is a division of application No. 11/884,509, filed as application No. PCT/US2006/005367 on Feb. 16, 2006, now Pat. No. 7,968,091.

(60) Provisional application No. 60/653,479, filed on Feb. 16, 2005.

(51) Int. Cl.
*A61K 39/00* (2006.01)
*A61K 38/18* (2006.01)
*C07K 14/475* (2006.01)

(52) U.S. Cl.
USPC ........... 424/134.1; 514/1.1; 514/5.4; 514/7.6; 530/350

(58) Field of Classification Search
None
See application file for complete search history.

(56) References Cited

U.S. PATENT DOCUMENTS

| | | | |
|---|---|---|---|
| 5,571,714 A | 11/1996 | Dasch et al. | |
| 5,719,120 A | 2/1998 | Letarte et al. | |
| 5,830,847 A | 11/1998 | Letarte et al. | |
| 6,015,693 A | 1/2000 | Letarte et al. | |

FOREIGN PATENT DOCUMENTS

| | | |
|---|---|---|
| CN | 1284380 | 2/2001 |
| WO | WO/94/24314 | 10/1994 |
| WO | WO/95/12608 | 5/1995 |
| WO | WO/02/051438 | 7/2002 |
| WO | WO/02/098444 | 12/2002 |
| WO | WO/03/004615 | 1/2003 |
| WO | WO/03/089608 | 10/2003 |
| WO | WO/2004/003150 | 1/2004 |
| WO | WO/2004/004750 | 1/2004 |
| WO | WO/2004/016606 | 2/2004 |
| WO | WO2004/092405 A2 | 10/2004 |
| WO | WO/2005/028517 A2 | 3/2005 |
| WO | WO/2005/028517 A3 | 3/2005 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Wiater et al., J. Biol. Chem., 278(10):7934-7941 (2003).
Weinstein et al., Blood, 100(10):3776-3781 (2002).
Xia et al., Mol. Endocrinol., 18:979-994 (2004).
Xia et al., Endocrinology 146(8):3614-3621 (2005).
Xia et al., J. Biol. Chem., 282(25):18129-18140 (2007).
Yamaguchi et al., Nature, 346:281-284 (1990).
International Preliminary Report on Patentability, Application No. PCT/US2006/005367, Dated: Aug. 21, 2007.
Examination Report, European Application No. 06735151.0, Dated: Nov. 12, 2008.
European Examination Report, Application No. EP 06735151.0, Mailing Date: Apr. 16, 2010.
Augsburger et al., Neuron., 24:127-141 (1999).
Babitt, J.L., et al., J. Biol. Chem., 280:29820-29827 (2005).
Babitt, et al., Nat. Genet., 38(5):531-539 (2006).
Balemans et al. Dev. Biol., 250:231-250 (2002).
Brinks et al., J. Neurosci., 24(15) 3862-3869 (2004).
Brown, C.B., et al., Science, 283:2080-2082(1999).
Chappuis-Flament et al., J. Cell Biol., 154(1):231-243 (2001).
Cheng, S.K., et al., Genes Dev., 17:31-36 (2003).
Database TrEMBL Q95XN8, Du, et al., "The sequence of C. elegans cosmid Y71G12B", Dec. 2001, 100% identical to SEQ ID No. 18.
Database, Auffray, C., et al., NCBI Accession No. CAB98207, Jul. 2000, 100% identical to SEQ ID No. 10 over 446 residues.
Database, WPI Week 2001 Derwent Publications Ltd., 2001-317422 XP002416009 & CN 1 284 380 A (Inst Hematology Chinese Acad Medical Sci) Feb. 21, 2001.
De Angelis et al., Microbiol., 147:1863-1873 (2001).
del Re, E., et al., J. Biol. Chem., 279:22765-22772 (2004).
Dennler et al., EMBO J., 17:3091-3100 (1998).
Feng et al., Science, 297:392-395 (2002).
Gray et al., Proc. Natl. Acad. Sci. USA, 100(9):5193-5198 (2003).

(Continued)

*Primary Examiner* — Christine J Saoud
*Assistant Examiner* — Jon M Lockard
(74) *Attorney, Agent, or Firm* — Lathrop & Gage LLP

(57) ABSTRACT

The present invention provides new systems and strategies for the regulation of iron metabolism in mammals. In particular, methods of using agonists and antagonists of TGF-β superfamily members to modulate the expression or activity of hepcidin, a key regulator of iron metabolism, are described. The inventive methods find applications in the treatment of diseases associated with iron overload, such as juvenile hemochromatosis and adult hemochromatosis, and in the treatment of diseases associated with iron deficiency, such as anemia of chronic disease and EPO resistant anemia in end-stage of renal disease. The present invention also relates to screening tools and methods for the development of novel drugs and therapies for treating iron metabolism disorders.

18 Claims, 22 Drawing Sheets

(56) References Cited

OTHER PUBLICATIONS

Groppe et al., Nature, 420:636-642(2002).
Hollnagel et al., J. Biol. Chem., 274(28):19838-19845 (1999).
Hoodless et al., Cell, 85:489-500 (1996).
Hsu, D. et al., Mol. Cell, 1:673-683 (1998).
Keutmann et al., Molec. Encocrinology, 18(1):228-240 (2004).
Klahr, J. Nephrol., 16:179-185 (2003).
Korchynskyi et al., J. Biol. Chem., 277:4883-4891 (2002).
Krijt et al., Blood, 104(13) 4308-4310 (2004).
Lopez-Rovira et al., J. Biol. Chem., 277(5):3176-3185 (2002).
Lopez-Casillas et al., Cell, 73:1435-1444 (1993).
Lu et al., Dev Dyn 222(4):667-680 (2001).
Macias-Silva et al., Cell, 87:1215-1224 (1996).
Martinez et al., Haematologica, 89:1441-1445 (2004).
Massague et al., Annu. Rev. Biochem., 67:753-791 (1998).
Massague et al., Genes Dev., 14:627-644 (2000).
Massague, Nat. Rev. Mol. Cell Biol., 200(1):169-178 (2000).
Matsunaga et al., Nat. Cell Biol., 6:749-755 (2004).
McMahon et al., Genes Dev., 12:1438-1452 (1998).
Monnier et al., Nature, 419:392-395 (2002).
Nemeth et al., Blood, 105(4):1803-1806 (2005).
Niederkofler et al., J. Neurosci., 24(4):808-818 (2004).
Nishi et al., Endocrinology, 142:437-445 (2001).
Oldekamp et al., Gene Expr. Patterns; 4:283-288 (2004).
Onichtchouk et al., Nature, 401:480-485 (1999).
Papanikolaou et al., Nature Genetics, 36:77-82 (2004).
Puglisi et al., Eur. J. Endocrinol., 151:511-520 (2004).
Rajagopalan et al., Nat. Cell Biol., 6:756-762 (2004).
Roetto et al., Nature Genetics, 33(1):21-22 (2003).
Samad et al., J. Neuroscience, 24:2027-2036 (2004).
Samad et al., J. Biol. Chem., 280:14122-14129 (2005).
Schmidtmer et al., Gene Expr. Patterns, 4:105-110 (2004).
Shen et al., Trends Genet., 16:303-309 (2000).
Shi et al., Cell, 113:685-700 (2003).
Storm et al., Development, 122:3969-3979 (1996).

\* cited by examiner

|  | Serum Iron | TIBC |  |
|---|---|---|---|
| BMP2 (18 mcg) | 114.02 | 216.80 | n=8 mice |
| Vehicle | 169.12 | 249.09 | n=7 mice |
| p value | 0.0194 | 0.0268 |  |

*Fig. 12*

| | JH3-201 | | JH3-202 | | JH6-205 | | JH7-201 | | JH10-201 | | JH12-201 | | JH11-201 | | JH4-203 | | JH8-202 | | JH9-202 | |
|---|---|---|---|---|---|---|---|---|---|---|---|---|---|---|---|---|---|---|---|---|
| D1S252 | 104 | 92 | 102 | 102 | 96 | 96 | 104 | 104 | 92 | 92 | 92 | 92 | 92 | 104 | 92 | 102 | 92 | 102 | 92 | 92 |
| D1S2698 | 167 | 167 | 165 | 165 | ND | 163 | 165 | 167 | 167 | 167 | 165 | 165 | 167 | 167 | 161 | 175 | 171 | 173 | 171 | 169 |
| CA3AL590452 | 249 | 249 | 249 | 251 | 255 | 249 | 249 | 247 | 248 | 248 | ND | ND | ND | ND | 249 | 251 | 248 | 248 | 248 | 251 |
| CA1AL355505 | 264 | 264 | 264 | 264 | 264 | 264 | 264 | 264 | 264 | 264 | 264 | 264 | 264 | 268 | 264 | 264 | 264 | 264 | 264 | 264 |
| GGAA1AL355505 | 297 | 297 | 297 | 297 | 297 | 297 | 297 | 297 | 297 | 297 | 297 | 297 | 293 | 293 | 293 | 293 | 293 | 293 | 297 | 297 |
| CA1AL160282 | 195 | 195 | 195 | 195 | 195 | 195 | 195 | 195 | 195 | 195 | 195 | 195 | 195 | 195 | 195 | 195 | 193 | 193 | 195 | 195 |
| D1S2344 | 255 | 255 | 255 | 255 | 255 | 255 | 255 | 255 | 255 | 255 | 255 | 255 | 255 | 153 | 255 | 255 | 259 | 259 | 253 | 253 |
| GATA1AL160282 | 383 | 380 | 380 | 380 | 380 | 380 | 380 | 380 | 380 | 380 | 363 | 363 | 380 | 384 | 363 | 363 | 364 | 364 | 363 | 363 |
| D1S442 | 270 | 270 | 270 | 270 | 270 | 270 | 270 | 270 | 270 | 270 | 270 | ND | 270 | 279 | 278 | 278 | 270 | 270 | 272 | 272 |
| CA1AL445591 | 377 | 377 | 377 | 377 | 377 | 377 | 377 | 377 | 377 | 377 | 317 | ND | 377 | 379 | 377 | 377 | 379 | 379 | 379 | 379 |
| CA3AL359207 | 407 | 407 | 407 | 407 | 407 | 407 | 407 | 409 | 407 | 407 | 407 | 407 | 407 | 407 | 419 | 419 | 408 | 408 | 419 | 419 |
| CA2AL359207 | 221 | 221 | 221 | 221 | 221 | 221 | 221 | 221 | 221 | 221 | 221 | 221 | 221 | 225 | 221 | 221 | 221 | 221 | 221 | 221 |
| CA1AL359207 | 256 | 256 | 256 | 256 | 256 | 256 | 256 | 242 | 258 | 258 | ND | ND | 256 | 242 | 246 | 246 | 242 | 242 | 246 | 246 |
| CA2AL590867 | 196 | 196 | 196 | 196 | 196 | 196 | 196 | 184 | 196 | 196 | ND | 208 | 196 | 184 | 194 | 194 | 196 | 196 | 184 | 184 |
| CA2AL381904 | 238 | 238 | 238 | 238 | 238 | 238 | 238 | 244 | 238 | 238 | ND | ND | 238 | 244 | 238 | 238 | 238 | 238 | 244 | 244 |
| CA1AL381904 | 208 | 208 | 208 | 208 | 208 | 208 | 208 | 208 | 208 | 208 | ND | ND | 208 | 206 | 208 | 208 | 208 | 208 | 208 | 208 |
| CA1AL356378 | 235 | 235 | 235 | 235 | 235 | 235 | 235 | 237 | 235 | 235 | ND | ND | 235 | 237 | 235 | 235 | 235 | 235 | 237 | 237 |
| CA1AL596177 | 176 | 178 | 176 | 176 | 239 | 239 | 176 | 170 | 178 | 178 | ND | ND | 176 | 176 | 174 | 174 | 180 | 180 | 184 | 184 |
| D1S2612 | 289 | 289 | 289 | 289 | 289 | 289 | 289 | 277 | 289 | 289 | 176 | 176 | 289 | 277 | 289 | 289 | 289 | 289 | 285 | 285 |
| CA1AL591493 | 170 | 170 | 170 | 170 | 170 | 170 | 170 | 170 | 170 | 170 | 170 | 170 | 170 | 182 | 180 | 180 | 174 | 174 | 180 | 180 |
| CA1AL358073 | 398 | 398 | 402 | 398 | 398 | 398 | 398 | 398 | 400 | 396 | ND | ND | 396 | 398 | 398 | 398 | 402 | 402 | 398 | 398 |
| D1S3466 | 176 | 176 | 164 | 164 | 176 | 176 | 164 | 176 | 174 | 178 | 176 | 176 | 176 | 176 | 176 | 176 | 172 | 172 | 176 | 176 |
| D1S498 | 201 | 201 | 205 | 205 | 201 | 201 | 209 | 201 | 201 | 197 | ND | ND | 205 | 107 | 197 | 197 | 197 | 197 | 205 | 205 |
| D1S2347 | 191 | 191 | 195 | 195 | 191 | 191 | 189 | 191 | 193 | 191 | ND | 193 | 195 | 195 | 195 | 195 | 190 | 193 | 191 | 195 |
| D1S2343 | 291 | 291 | 272 | 272 | 291 | 291 | 285 | 291 | 283 | 283 | 256 | ND | 274 | 272 | 272 | 272 | 272 | 272 | 272 | 272 |
| D1S2635 | 242 | 242 | 256 | 256 | 260 | 260 | 256 | 260 | 258 | 242 | ND | ND | 258 | 258 | 258 | 258 | 256 | 256 | 256 | 256 |
| | 157 | 151 | 161 | 157 | 154 | 159 | 157 | 157 | 157 | 163 | 161 | 154 | 157 | 152 | 159 | 152 | 161 | 159 | 159 | 154 |

*Fig. 17*

```
                        SEQUENCE LISTING

<160> NUMBER OF SEQ ID NOS: 30

<210> SEQ ID NO 1
<211> LENGTH: 19
<212> TYPE: DNA
<213> ORGANISM: Artificial Sequence
<220> FEATURE:
<223> OTHER INFORMATION: Synthetic primer

<400> SEQUENCE: 1
ctgcaacccc aggacagag                                                        19

<210> SEQ ID NO 2
<211> LENGTH: 23
<212> TYPE: DNA
<213> ORGANISM: Artificial Sequence
<220> FEATURE:
<223> OTHER INFORMATION: Synthetic primer

<400> SEQUENCE: 2
ggaataaata aggaagggag ggg                                                   23

<210> SEQ ID NO 3
<211> LENGTH: 22
<212> TYPE: DNA
<213> ORGANISM: Artificial Sequence
<220> FEATURE:
<223> OTHER INFORMATION: Synthetic primer

<400> SEQUENCE: 3
aggatgcaga aggagatcac tg                                                    22

<210> SEQ ID NO 4
<211> LENGTH: 24
<212> TYPE: DNA
<213> ORGANISM: Artificial Sequence
<220> FEATURE:
<223> OTHER INFORMATION: Synthetic primer

<400> SEQUENCE: 4
gggtgtaacg caactaagtc atag                                                  24

<210> SEQ ID NO 5
<211> LENGTH: 28
<212> TYPE: DNA
<213> ORGANISM: Artificial Sequence
<220> FEATURE:
<223> OTHER INFORMATION: Synthetic primer
```

```
<400> SEQUENCE: 5
accgaattcg ggggacctgg ctggatag                                    28

<210> SEQ ID NO 6
<211> LENGTH: 24
<212> TYPE: DNA
<213> ORGANISM: Artificial Sequence
<220> FEATURE:
<223> OTHER INFORMATION: Synthetic primer

<400> SEQUENCE: 6
cggagggcat accccaacac acag                                        24

<210> SEQ ID NO 7
<211> LENGTH: 24
<212> TYPE: DNA
<213> ORGANISM: Artificial Sequence
<220> FEATURE:
<223> OTHER INFORMATION: Synthetic primer

<400> SEQUENCE: 7
ctgtgtgttg gggtatgccc tccg                                        24

<210> SEQ ID NO 8
<211> LENGTH: 29
<212> TYPE: DNA
<213> ORGANISM: Artificial Sequence
<220> FEATURE:
<223> OTHER INFORMATION: Synthetic primer

<400> SEQUENCE: 8
ccctctagat ggtgccagtc tccaaaagc                                   29

<210> SEQ ID NO 9
<211> LENGTH: 26
<212> TYPE: DNA
<213> ORGANISM: Artificial Sequence
<220> FEATURE:
<223> OTHER INFORMATION: Synthetic primer

<400> SEQUENCE: 9
ggaagcttat gggccagtcc cctagt                                      26

<210> SEQ ID NO 10
<211> LENGTH: 29
<212> TYPE: DNA
<213> ORGANISM: Artificial Sequence
<220> FEATURE:
<223> OTHER INFORMATION: Synthetic primer

<400> SEQUENCE: 10
ccggatccgc taagttctct aaatccgtc                                   29

<210> SEQ ID NO 11
<211> LENGTH: 29
<212> TYPE: DNA
<213> ORGANISM: Artificial Sequence
<220> FEATURE:
<223> OTHER INFORMATION: Synthetic primer

<400> SEQUENCE: 11
cgagaattca cttacagggc ttccggtca                                   29

<210> SEQ ID NO 12
<211> LENGTH: 36
```

-continued

<212> TYPE: DNA
<213> ORGANISM: Artificial Sequence
<220> FEATURE:
<223> OTHER INFORMATION: Synthetic primer

<400> SEQUENCE: 12
gcattgagaa tgagcatgtc cacagaggag cagcag                          36

<210> SEQ ID NO 13
<211> LENGTH: 42
<212> TYPE: DNA
<213> ORGANISM: Artificial Sequence
<220> FEATURE:
<223> OTHER INFORMATION: Synthetic primer

<400> SEQUENCE: 13
cctctgtgga catgctcatt ctcaatgcaa gatcctccgc tg                   42

<210> SEQ ID NO 14
<211> LENGTH: 40
<212> TYPE: DNA
<213> ORGANISM: Artificial Sequence
<220> FEATURE:
<223> OTHER INFORMATION: Synthetic primer

<400> SEQUENCE: 14
cgtctcgagt tactgaatgc aaagccacag aacaaagagc                      40

<210> SEQ ID NO 15
<211> LENGTH: 41
<212> TYPE: DNA
<213> ORGANISM: Artificial Sequence
<220> FEATURE:
<223> OTHER INFORMATION: Synthetic primer

<400> SEQUENCE: 15
gacagatctg cggccgctca ttctcaatgc aagatcctcc g                    41

<210> SEQ ID NO 16
<211> LENGTH: 24
<212> TYPE: DNA
<213> ORGANISM: Artificial Sequence
<220> FEATURE:
<223> OTHER INFORMATION: Synthetic primer

<400> SEQUENCE: 16
gagcagttgt gctggatcat cagg                                       24

<210> SEQ ID NO 17
<211> LENGTH: 19
<212> TYPE: PRT
<213> ORGANISM: Mus musculus

<400> SEQUENCE: 17

Arg Val Ala Glu Asp Val Ala Arg Ala Phe Ser Ala Glu Gln Asp Leu
1               5                   10                  15

Gln Leu Cys

<210> SEQ ID NO 18
<211> LENGTH: 21
<212> TYPE: DNA
<213> ORGANISM: Artificial Sequence
<220> FEATURE:
<223> OTHER INFORMATION: Synthetic primer

<400> SEQUENCE: 18

-continued cgtgaccaga cttttggaca c                                              21

<210> SEQ ID NO 19
<211> LENGTH: 21
<212> TYPE: DNA
<213> ORGANISM: Artificial Sequence
<220> FEATURE:
<223> OTHER INFORMATION: Synthetic primer

<400> SEQUENCE: 19
ggcatgatta gtggagttca g                                              21

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
agcagccaaa ctatgggcta                                                20

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
tggttgagtt gaggtggtca                                                20

<210> SEQ ID NO 22
<211> LENGTH: 21
<212> TYPE: DNA
<213> ORGANISM: Artificial Sequence
<220> FEATURE:
<223> OTHER INFORMATION: Synthetic primer

<400> SEQUENCE: 22
tccttagact gcacagcaga a                                              21

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
ataaataagg acgggagggg                                                20

<210> SEQ ID NO 24
<211> LENGTH: 426
<212> TYPE: PRT
<213> ORGANISM: Homo sapiens

<400> SEQUENCE: 24

Met Gly Glu Pro Gly Gln Ser Pro Ser Pro Arg Ser Ser His Gly Ser
1               5                   10                  15

Pro Pro Thr Leu Ser Thr Leu Thr Leu Leu Leu Leu Cys Gly His Ala
            20                  25                  30

His Ser Gln Cys Lys Ile Leu Arg Cys Asn Ala Glu Tyr Val Ser
        35                  40                  45

Ser Thr Leu Ser Leu Arg Gly Gly Gly Ser Ser Gly Ala Leu Arg Gly

```
                        50                  55                  60
Gly Gly Gly Gly Arg Gly Gly Val Gly Ser Gly Gly Leu Cys
 65                  70                  75                  80
Arg Ala Leu Arg Ser Tyr Ala Leu Cys Thr Arg Thr Ala Arg Thr
                 85                  90                  95
Cys Arg Gly Asp Leu Ala Phe His Ser Ala Val His Gly Ile Glu Asp
                100                 105                 110
Leu Met Ile Gln His Asn Cys Ser Arg Gln Gly Pro Thr Ala Pro Pro
                115                 120                 125
Pro Pro Arg Gly Pro Ala Leu Pro Gly Ala Ser Gly Leu Pro Ala
130                 135                 140
Pro Asp Pro Cys Asp Tyr Glu Gly Arg Phe Ser Arg Leu His Gly Arg
145                 150                 155                 160
Pro Pro Gly Phe Leu His Cys Ala Ser Phe Gly Asp Pro His Val Arg
                165                 170                 175
Ser Phe His His His Phe His Thr Cys Arg Val Gln Gly Ala Trp Pro
                180                 185                 190
Leu Leu Asp Asn Asp Phe Leu Phe Val Gln Ala Thr Ser Ser Pro Met
                195                 200                 205
Ala Leu Gly Ala Asn Ala Thr Ala Thr Arg Lys Leu Thr Ile Ile Phe
210                 215                 220
Lys Asn Met Gln Glu Cys Ile Asp Gln Lys Val Tyr Gln Ala Glu Val
225                 230                 235                 240
Asp Asn Leu Pro Val Ala Phe Glu Asp Gly Ser Ile Asn Gly Gly Asp
                245                 250                 255
Arg Pro Gly Gly Ser Ser Leu Ser Ile Gln Thr Ala Asn Pro Gly Asn
                260                 265                 270
His Val Glu Ile Gln Ala Ala Tyr Ile Gly Thr Thr Ile Ile Ile Arg
                275                 280                 285
Gln Thr Ala Gly Gln Leu Ser Phe Ser Ile Lys Val Ala Glu Asp Val
                290                 295                 300
Ala Met Ala Phe Ser Ala Glu Gln Asp Leu Gln Leu Cys Val Gly Gly
305                 310                 315                 320
Cys Pro Pro Ser Gln Arg Leu Ser Arg Ser Glu Arg Asn Arg Arg Gly
                325                 330                 335
Ala Ile Thr Ile Asp Thr Ala Arg Arg Leu Cys Lys Glu Gly Leu Pro
                340                 345                 350
Val Glu Asp Ala Tyr Phe His Ser Cys Val Phe Asp Val Leu Ile Ser
                355                 360                 365
Gly Asp Pro Asn Phe Thr Val Ala Ala Gln Ala Ala Leu Glu Asp Ala
                370                 375                 380
Arg Ala Phe Leu Pro Asp Leu Glu Lys Leu His Leu Phe Pro Ser Asp
385                 390                 395                 400
Ala Gly Val Pro Leu Ser Ser Ala Thr Leu Leu Ala Pro Leu Leu Ser
                405                 410                 415
Gly Leu Phe Val Leu Trp Leu Cys Ile Gln
                420                 425

<210> SEQ ID NO 25
<211> LENGTH: 422
<212> TYPE: PRT
<213> ORGANISM: Rattus norvegicus

<400> SEQUENCE: 25

Met Gly Asp Arg Gly Arg Ser Pro Ser Leu Arg Ser Pro His Gly Ser
```

-continued

```
1               5               10              15
Pro Pro Thr Leu Ser Thr Leu Thr Leu Leu Leu Leu Cys Gly Gln
                20              25              30

Ala His Ser Gln Cys Lys Ile Leu Arg Cys Asn Ala Glu Tyr Val Ser
            35              40              45

Phe Thr Leu Ser Leu Arg Gly Gly Ser Pro Asp Thr Pro Arg Gly
    50              55              60

Gly Gly Arg Gly Gly Pro Ala Ser Gly Gly Leu Cys Arg Ala Leu Arg
65              70              75              80

Ser Tyr Ala Leu Cys Thr Arg Arg Thr Ala Arg Thr Cys Arg Gly Asp
                85              90              95

Leu Ala Phe His Ser Ala Val His Gly Ile Glu Asp Leu Met Ile Gln
            100             105             110

His Asn Cys Ser Arg Gln Gly Pro Thr Ala Ser Pro Pro Ala Arg Gly
            115             120             125

Pro Ala Leu Pro Gly Ala Gly Pro Ala Pro Leu Thr Pro Asp Pro Cys
        130             135             140

Asp Tyr Glu Ala Arg Phe Ser Arg Leu His Gly Arg Thr Pro Gly Phe
145             150             155             160

Leu His Cys Ala Ser Phe Gly Asp Pro His Val Arg Ser Phe His Asn
                165             170             175

His Phe His Thr Cys Arg Val Gln Gly Ala Trp Pro Leu Leu Asp Asn
            180             185             190

Asp Phe Leu Phe Val Gln Ala Thr Ser Ser Pro Val Ala Ser Gly Ala
            195             200             205

Asn Ala Thr Thr Ile Arg Lys Ile Thr Ile Ile Phe Lys Asn Met Gln
        210             215             220

Glu Cys Ile Asp Gln Lys Val Tyr Gln Ala Glu Val Asp Asn Leu Pro
225             230             235             240

Ala Ala Phe Glu Asp Gly Ser Val Asn Gly Gly Asp Arg Pro Gly Gly
                245             250             255

Ser Ser Leu Ser Ile Gln Thr Ala Asn Leu Gly Ser His Val Glu Ile
            260             265             270

Arg Ala Ala Tyr Ile Gly Thr Thr Ile Ile Val Arg Gln Thr Ala Gly
        275             280             285

Gln Leu Ser Phe Ser Ile Arg Val Ala Glu Asp Val Ala Arg Ala Phe
            290             295             300

Ser Ala Glu Gln Asp Leu Gln Leu Cys Val Gly Gly Cys Pro Pro Ser
305             310             315             320

Gln Arg Leu Ser Arg Ser Glu Arg Asn Arg Arg Gly Ala Ile Ala Ile
                325             330             335

Asp Thr Ala Arg Arg Leu Cys Lys Glu Gly Leu Pro Val Glu Asp Ala
            340             345             350

Tyr Phe Gln Ser Cys Val Phe Asp Val Ser Val Ser Gly Asp Pro Asn
            355             360             365

Phe Thr Val Ala Ala Gln Ser Ala Leu Asp Asp Ala Arg Val Phe Leu
    370             375             380

Thr Asp Leu Glu Asn Leu His Leu Phe Pro Val Asp Ala Gly Pro Pro
385             390             395             400

Leu Ser Pro Ala Thr Cys Leu Val Arg Leu Ser Val Leu Phe Val
                405             410             415

Leu Trp Phe Cys Ile Gln
            420
```

<210> SEQ ID NO 26
<211> LENGTH: 420
<212> TYPE: PRT
<213> ORGANISM: Mus musculus

<400> SEQUENCE: 26

```
Met Gly Gln Ser Pro Ser Pro Arg Ser Pro His Gly Ser Pro Pro Thr
1               5                   10                  15

Leu Ser Thr Leu Thr Leu Leu Leu Leu Cys Gly Gln Ala His Ser
            20                  25                  30

Gln Cys Lys Ile Leu Arg Cys Asn Ala Glu Tyr Val Ser Ser Thr Leu
        35                  40                  45

Ser Leu Arg Gly Gly Ser Pro Asp Thr Pro Arg Gly Gly Gly Arg
    50                  55                  60

Gly Gly Leu Ala Ser Gly Gly Leu Cys Arg Ala Leu Arg Ser Tyr Ala
65                  70                  75                  80

Leu Cys Thr Arg Arg Thr Ala Arg Thr Cys Arg Gly Asp Leu Ala Phe
                85                  90                  95

His Ser Ala Val His Gly Ile Glu Asp Leu Met Ile Gln His Asn Cys
            100                 105                 110

Ser Arg Gln Gly Pro Thr Ala Pro Pro Ala Arg Gly Pro Ala Leu
        115                 120                 125

Pro Gly Ala Gly Pro Ala Pro Leu Thr Pro Asp Pro Cys Asp Tyr Glu
130                 135                 140

Ala Arg Phe Ser Arg Leu His Gly Arg Ala Pro Gly Phe Leu His Cys
145                 150                 155                 160

Ala Ser Phe Gly Asp Pro His Val Arg Ser Phe His Asn Gln Phe His
                165                 170                 175

Thr Cys Arg Val Gln Gly Ala Trp Pro Leu Leu Asp Asn Asp Phe Leu
            180                 185                 190

Phe Val Gln Ala Thr Ser Ser Pro Val Ser Ser Gly Ala Asn Ala Thr
        195                 200                 205

Thr Ile Arg Lys Ile Thr Ile Ile Phe Lys Asn Met Gln Glu Cys Ile
    210                 215                 220

Asp Gln Lys Val Tyr Gln Ala Glu Val Asp Asn Leu Pro Ala Ala Phe
225                 230                 235                 240

Glu Asp Gly Ser Ile Asn Gly Gly Asp Arg Pro Gly Gly Ser Ser Leu
                245                 250                 255

Ser Ile Gln Thr Ala Asn Leu Gly Ser His Val Glu Ile Arg Ala Ala
            260                 265                 270

Tyr Ile Gly Thr Thr Ile Ile Arg Gln Thr Ala Gly Gln Leu Ser
        275                 280                 285

Phe Ser Ile Arg Val Ala Glu Asp Val Ala Arg Ala Phe Ser Ala Glu
290                 295                 300

Gln Asp Leu Gln Leu Cys Val Gly Gly Cys Pro Pro Ser Gln Arg Leu
305                 310                 315                 320

Ser Arg Ser Glu Arg Asn Arg Arg Gly Ala Ile Ala Ile Asp Thr Ala
                325                 330                 335

Arg Arg Leu Cys Lys Glu Gly Leu Pro Val Glu Asp Ala Tyr Phe Gln
            340                 345                 350

Ser Cys Val Phe Asp Val Ser Val Ser Gly Asp Pro Asn Phe Thr Val
        355                 360                 365

Ala Ala Gln Thr Ala Leu Asp Asp Ala Arg Ile Phe Leu Thr Asp Leu
    370                 375                 380
```

```
Glu Asn Leu His Leu Phe Pro Ser Asp Ala Gly Pro Pro Leu Ser Pro
385                 390                 395                 400

Ala Ile Cys Leu Val Pro Leu Leu Ser Ala Leu Phe Val Leu Trp Leu
                405                 410                 415

Cys Phe Ser Lys
            420

<210> SEQ ID NO 27
<211> LENGTH: 408
<212> TYPE: PRT
<213> ORGANISM: Danio rerio

<400> SEQUENCE: 27

Met Ala Ala Ser Ala Gly Gly Asn His Ser His Thr Thr Trp Arg
1               5                   10                  15

His Ile Val Ile Ile Val Leu Met Val Leu Leu Phe Ser Ala Pro Ser
                20                  25                  30

Val Cys Ala Gln Cys Arg Ile Leu Arg Cys Asn Ser Asp Phe Val Ala
            35                  40                  45

Ala Thr Leu Glu Ser Gly Val Ile Gly Gly Asn Lys Glu Gly Val
50                  55                  60

Asn Thr Gly Tyr Cys Ser Ala Leu Arg Ser Tyr Ala Leu Cys Thr Gln
65                  70                  75                  80

Arg Thr Ala Arg Ala Cys Arg Gly Asp Leu Ala Tyr His Ser Ala Val
                85                  90                  95

Gln Gly Ile Glu Asp Leu Leu Ile Gln Tyr Arg Cys Pro Lys Ala Gly
            100                 105                 110

Pro Thr Ala Gln Pro Gln Pro Arg Pro Leu Pro Gln Ala Pro Leu Ser
        115                 120                 125

Gly Asp Gly Cys Phe Tyr Glu Lys Gly Phe Ile Gln Arg Glu Gly Arg
130                 135                 140

Ala Pro Glu Tyr Leu His Cys Gly Val Phe Gly Asp Pro His Ile Arg
145                 150                 155                 160

Thr Phe Asn Glu Glu Phe Gln Thr Cys Ala Val Gln Gly Ala Trp Pro
                165                 170                 175

Leu Ile Asp Asn Gln Tyr Leu Tyr Ile Gln Ala Thr Ser Ser Pro Thr
            180                 185                 190

Arg Glu Ser Ser Asp Thr Thr Ile Leu Thr Glu Val Thr Val Ile Phe
        195                 200                 205

Gln Asn Trp Arg Glu Cys Ala Glu Gln Gln Val Tyr Gln Ala Lys Leu
210                 215                 220

Gly Asn Val Pro Pro Ala Phe Ala Asp Gly Ser Val Thr Gly Gly Asp
225                 230                 235                 240

Arg Arg Gly His Gln Ser Leu Arg Ile His Ser Gln Asp Pro Gly Arg
                245                 250                 255

His Ala Glu Ile Trp Ala Thr His Ile Gly Thr Met Ile Ile Val Arg
            260                 265                 270

Gln Val Gly Gln Ser Leu Ser Leu Ser Val Arg Ser Pro Arg Ala Ile
        275                 280                 285

Val Glu Ser Tyr Thr Pro Glu Gln Asp Leu Gln Leu Cys Val Trp Gly
290                 295                 300

Cys Pro Ile Ser Gln Arg Leu Glu Met Leu His Ala His Pro Phe Asp
305                 310                 315                 320

Pro Ala Tyr Thr His Cys Ser Ser Leu Phe Pro Gly Arg Asp Val Tyr
                325                 330                 335
```

-continued

```
Phe Gln Ala Cys Leu Phe Asp Val Gln Val Thr Gly Asp Val Asn Ser
                340                 345                 350

Ser Ala Ser Ala Val Ala Ala Leu Glu Asp Ala Arg Ala Met Ile Ser
            355                 360                 365

Asp Pro Ala Ser Val His Leu Val Thr Gly Thr Gly Asn Asn Ser
370                 375                 380

Pro Ser Leu Leu Val Val Leu Gly Phe Ser Phe Leu Thr Glu Thr Leu
385                 390                 395                 400

Arg His Ser Phe Leu Gly Ser Ala
                405

<210> SEQ ID NO 28
<211> LENGTH: 432
<212> TYPE: PRT
<213> ORGANISM: Homo sapiens

<400> SEQUENCE: 28

Met Gly Arg Gly Ala Gly Arg Ser Ala Leu Gly Phe Trp Pro Thr Leu
1               5                   10                  15

Ala Phe Leu Leu Cys Ser Phe Pro Ala Ala Thr Ser Pro Cys Lys Ile
                20                  25                  30

Leu Lys Cys Asn Ser Glu Phe Trp Ser Ala Thr Ser Gly Ser His Ala
            35                  40                  45

Pro Ala Ser Asp Asp Thr Pro Glu Phe Cys Ala Ala Leu Arg Ser Tyr
50                  55                  60

Ala Leu Cys Thr Arg Arg Thr Ala Arg Thr Cys Arg Gly Asp Leu Ala
65                  70                  75                  80

Tyr His Ser Ala Val His Gly Ile Glu Asp Leu Met Ser Gln His Asn
                85                  90                  95

Cys Ser Lys Asp Gly Pro Thr Ser Gln Pro Arg Leu Arg Thr Leu Pro
            100                 105                 110

Pro Ala Gly Asp Ser Gln Glu Arg Ser Asp Ser Pro Glu Ile Cys His
        115                 120                 125

Tyr Glu Lys Ser Phe His Lys His Ser Ala Thr Pro Asn Tyr Thr His
130                 135                 140

Cys Gly Leu Phe Gly Asp Pro His Leu Arg Thr Phe Thr Asp Arg Phe
145                 150                 155                 160

Gln Thr Cys Lys Val Gln Gly Ala Trp Pro Leu Ile Asp Asn Asn Tyr
                165                 170                 175

Leu Asn Val Gln Ala Thr Asn Thr Pro Val Leu Pro Gly Ser Ala Ala
            180                 185                 190

Thr Ala Thr Ser Lys Leu Thr Ile Ile Phe Lys Asn Phe Gln Glu Cys
        195                 200                 205

Val Asp Gln Lys Val Tyr Gln Ala Glu Met Asp Glu Leu Pro Ala Ala
210                 215                 220

Phe Val Asp Gly Ser Lys Asn Gly Gly Asp Lys His Gly Ala Asn Ser
225                 230                 235                 240

Leu Lys Ile Thr Glu Lys Val Ser Gly Gln His Val Glu Ile Gln Ala
                245                 250                 255

Lys Tyr Ile Gly Thr Thr Ile Val Val Arg Gln Val Gly Arg Tyr Leu
            260                 265                 270

Thr Phe Ala Val Arg Met Pro Glu Glu Val Val Asn Ala Val Glu Asp
        275                 280                 285

Trp Asp Ser Gln Gly Leu Tyr Leu Cys Leu Arg Gly Cys Pro Leu Asn
290                 295                 300
```

```
Gln Gln Ile Asp Phe Gln Ala Phe His Thr Asn Ala Glu Gly Thr Gly
305                 310                 315                 320

Ala Arg Arg Leu Ala Ala Ser Pro Ala Pro Thr Ala Pro Glu Thr
                325                 330                 335

Phe Pro Tyr Glu Thr Ala Val Ala Lys Cys Lys Glu Lys Leu Pro Val
            340                 345                 350

Glu Asp Leu Tyr Tyr Gln Ala Cys Val Phe Asp Leu Leu Thr Thr Gly
                355                 360                 365

Asp Val Asn Phe Thr Leu Ala Ala Tyr Tyr Ala Leu Glu Asp Val Lys
            370                 375                 380

Met Leu His Ser Asn Lys Asp Lys Leu His Leu Tyr Glu Arg Thr Arg
385                 390                 395                 400

Asp Leu Pro Gly Arg Ala Ala Ala Gly Leu Pro Leu Ala Pro Arg Pro
                405                 410                 415

Leu Leu Gly Ala Leu Val Pro Leu Leu Ala Leu Leu Pro Val Phe Cys
                420                 425                 430

<210> SEQ ID NO 29
<211> LENGTH: 432
<212> TYPE: PRT
<213> ORGANISM: Gallus gallus

<400> SEQUENCE: 29

Met Gly Arg Gly Ala Gly Ser Thr Ala Leu Gly Leu Phe Gln Ile Leu
1               5                   10                  15

Pro Val Phe Leu Cys Ile Phe Pro Pro Val Thr Ser Pro Cys Lys Ile
            20                  25                  30

Leu Lys Cys Asn Ser Glu Phe Trp Ala Ala Thr Ser Gly Ser His His
            35                  40                  45

Leu Gly Ala Glu Glu Thr Pro Glu Phe Cys Thr Ala Leu Arg Ala Tyr
50                  55                  60

Ala His Cys Thr Arg Arg Thr Ala Arg Thr Cys Arg Gly Asp Leu Ala
65                  70                  75                  80

Tyr His Ser Ala Val His Gly Ile Asp Asp Leu Met Val Gln His Asn
                85                  90                  95

Cys Ser Lys Asp Gly Pro Thr Ser Gln Pro Arg Leu Arg Thr Leu Pro
            100                 105                 110

Pro Gly Asp Ser Gln Glu Arg Ser Asp Ser Pro Glu Ile Cys His Tyr
            115                 120                 125

Glu Lys Ser Phe His Lys His Ser Ala Ala Pro Asn Tyr Thr His Cys
            130                 135                 140

Gly Leu Phe Gly Asp Pro His Leu Arg Thr Phe Thr Asp Thr Phe Gln
145                 150                 155                 160

Thr Cys Lys Val Gln Gly Ala Trp Pro Leu Ile Asp Asn Asn Tyr Leu
                165                 170                 175

Asn Val Gln Val Thr Asn Thr Pro Val Leu Pro Gly Ser Ser Ala Thr
            180                 185                 190

Ala Thr Ser Lys Leu Thr Ile Ile Phe Lys Ser Phe Gln Glu Cys Val
            195                 200                 205

Glu Gln Lys Val Tyr Gln Ala Glu Met Asp Glu Leu Pro Ala Ala Phe
            210                 215                 220

Ala Asp Gly Ser Lys Asn Gly Gly Asp Lys His Gly Ala Asn Ser Leu
225                 230                 235                 240

Lys Ile Thr Glu Lys Val Ser Gly Gln His Ile Glu Ile Gln Ala Lys
                245                 250                 255
```

```
Tyr Ile Gly Thr Thr Ile Val Val Arg Gln Val Gly Arg Tyr Leu Thr
            260                 265                 270

Phe Ala Val Arg Met Pro Glu Glu Val Val Asn Ala Val Glu Asp Arg
        275                 280                 285

Asp Ser Gln Gly Leu Tyr Leu Cys Leu Arg Gly Cys Pro Leu Asn Gln
    290                 295                 300

Gln Ile Asp Phe Gln Thr Phe Arg Leu Ala Gln Ala Glu Gly Arg
305                 310                 315                 320

Ala Arg Arg Lys Gly Pro Ser Leu Pro Ala Pro Glu Ala Phe Thr
                325                 330                 335

Tyr Glu Ser Ala Thr Ala Lys Cys Arg Glu Lys Leu Pro Val Glu Asp
            340                 345                 350

Leu Tyr Phe Gln Ser Cys Val Phe Asp Leu Leu Thr Thr Gly Asp Val
        355                 360                 365

Asn Phe Met Leu Ala Ala Tyr Tyr Ala Phe Glu Asp Val Lys Met Leu
    370                 375                 380

His Ser Asn Lys Asp Lys Leu His Leu Tyr Glu Arg Thr Arg Ala Leu
385                 390                 395                 400

Ala Pro Gly Asn Ala Ala Pro Ser Glu His Pro Trp Ala Leu Pro Ala
                405                 410                 415

Leu Trp Val Ala Leu Leu Ser Leu Ser Gln Cys Trp Leu Gly Leu Leu
            420                 425                 430

<210> SEQ ID NO 30
<211> LENGTH: 437
<212> TYPE: PRT
<213> ORGANISM: Homo sapiens

<400> SEQUENCE: 30

Met Gly Leu Arg Ala Ala Pro Ser Ser Ala Ala Ala Ala Ala Ala Glu
1               5                   10                  15

Val Glu Gln Arg Arg Ser Pro Gly Leu Cys Pro Pro Leu Glu Leu
            20                  25                  30

Leu Leu Leu Leu Leu Phe Ser Leu Gly Leu Leu His Ala Gly Asp Cys
        35                  40                  45

Gln Gln Pro Ala Gln Cys Arg Ile Gln Lys Cys Thr Thr Asp Phe Val
    50                  55                  60

Ser Leu Thr Ser His Leu Asn Ser Ala Val Asp Gly Phe Asp Ser Glu
65                  70                  75                  80

Phe Cys Lys Ala Leu Arg Ala Tyr Ala Gly Cys Thr Gln Arg Thr Ser
                85                  90                  95

Lys Ala Cys Arg Gly Asn Leu Val Tyr His Ser Ala Val Leu Gly Ile
            100                 105                 110

Ser Asp Leu Met Ser Gln Arg Asn Cys Ser Lys Asp Gly Pro Thr Ser
        115                 120                 125

Ser Thr Asn Pro Glu Val Thr His Asp Pro Cys Asn Tyr His Ser His
    130                 135                 140

Ala Gly Ala Arg Glu His Arg Arg Gly Asp Gln Asn Pro Pro Ser Tyr
145                 150                 155                 160

Leu Phe Cys Gly Leu Phe Gly Asp Pro His Leu Arg Thr Phe Lys Asp
                165                 170                 175

Asn Phe Gln Thr Cys Lys Val Glu Gly Ala Trp Pro Leu Ile Asp Asn
            180                 185                 190

Asn Tyr Leu Ser Val Gln Val Thr Asn Val Pro Val Val Pro Gly Ser
        195                 200                 205
```

-continued

```
Ser Ala Thr Ala Thr Asn Lys Ile Thr Ile Ile Phe Lys Ala His His
    210                 215                 220

Glu Cys Thr Asp Gln Lys Val Tyr Gln Ala Val Thr Asp Asp Leu Pro
225                 230                 235                 240

Ala Ala Phe Val Asp Gly Thr Thr Ser Gly Gly Asp Ser Asp Ala Lys
                245                 250                 255

Ser Leu Arg Ile Val Glu Arg Glu Ser Gly His Tyr Val Glu Met His
                260                 265                 270

Ala Arg Tyr Ile Gly Thr Thr Val Phe Val Arg Gln Val Gly Arg Tyr
        275                 280                 285

Leu Thr Leu Ala Ile Arg Met Pro Glu Asp Leu Ala Met Ser Tyr Glu
    290                 295                 300

Glu Ser Gln Asp Leu Gln Leu Cys Val Asn Gly Cys Pro Leu Ser Glu
305                 310                 315                 320

Arg Ile Asp Asp Gly Gln Gly Gln Val Ser Ala Ile Leu Gly His Ser
                325                 330                 335

Leu Pro Arg Thr Ser Leu Val Gln Ala Trp Pro Gly Tyr Thr Leu Glu
                340                 345                 350

Thr Ala Asn Thr Gln Cys His Glu Lys Met Pro Val Lys Asp Ile Tyr
                355                 360                 365

Phe Gln Ser Cys Val Phe Asp Leu Leu Thr Thr Gly Asp Ala Asn Phe
    370                 375                 380

Thr Ala Ala Ala His Ser Ala Leu Glu Asp Val Glu Ala Leu His Pro
385                 390                 395                 400

Arg Lys Glu Arg Trp His Ile Phe Pro Ser Ser Gly Asn Gly Thr Pro
                405                 410                 415

Arg Gly Gly Ser Asp Leu Ser Val Ser Leu Gly Leu Thr Cys Leu Ile
                420                 425                 430

Leu Ile Val Phe Leu
                435
```

HEMOJUVELIN FUSION PROTEINS

CROSS-REFERENCE TO RELATED APPLICATIONS

The present application is a continuation of U.S. patent application Ser. No. 13/171,438, filed Jun. 28, 2011, which is a divisional application of U.S. patent application Ser. No. 11/884,509, filed on Jun. 17, 2008, which is a U.S. National Stage of International Application No. PCT/US2006/005367, filed on Feb. 16, 2006, which claims priority to U.S. Provisional Application No. 60/653,479 filed on Feb. 16, 2005 and entitled "Methods and Compositions to Regulate Iron Metabolism". The Provisional Application which is incorporated herein by reference in its entirety their entireties.

REFERENCE TO A "SEQUENCE LISTING"

The sequence listing material in the text file entitled "11884509_SeqList.txt" (30,633 bytes), which was created on Nov. 8, 2010, is herein incorporated by reference in its entirety.

BACKGROUND OF THE INVENTION

Iron is an essential element for the growth and survival of nearly all living organisms (P. Aisen et al., J. Biochem. Cell Biol., 2001, 33: 940-959) except for a few unusual bacterial species. It plays an important role in oxygen transport and storage (in combination with oxygen-binding molecules such as hemoglobin and myoglobulin) and is a key component of many enzymes that catalyze the redox reactions required for the generation of energy (e.g., cytochromes), the production of various metabolic intermediates, and for host defense (e.g., nicotinamide adenine dinucleotide phosphate [NADPH] oxidase). Iron can also be toxic. It catalyzes the generation of reactive radical species that can attack cellular membranes, proteins, and DNA (J. M. C. Gutteridge et al., Biochem. J., 1982, 296: 605-609), and activates NF-κB, the prototype transcription factor for genes involved in inflammation (S. Xiong et al., J. Biol. Chem., 2003, 278: 17646-17654). At high levels, iron accumulation in tissues is damaging.

To prevent iron deficiency or iron overload, virtually all organisms have developed elaborate mechanisms for regulating iron intake and efflux (C. Finch, Blood, 1994, 84: 1697-1702). In adult mammals, iron homeostasis depends upon regulated absorption of iron by the enterocyte, a highly specialized cell of the duodenum that coordinates dietary iron uptake and transport into the body. In the fetus, the mechanisms involved in placental materno-fetal iron transport are also tightly regulated. Iron is stored in the body in the form of the protein complexes, ferritin and hemosiderin, and is transported in the plasma via the protein complex, transferrin. Under normal circumstances, only trace amounts of iron exist outside these physiologic sinks, although stored iron can be mobilized by reuse. Perturbations in these highly regulated mechanisms can lead to iron overload or iron deficiency in the body.

Iron deficiency is the most common nutritional disorder in the world. As many as 4-5 billion people 65-80% of the world's population) may be iron deficient; and 2 billion people (over 30% of the world's population, mostly children and women of childbearing age) are anemic, mainly due to iron deficiency. In developing countries, the disease is exacerbated by malaria and worm infections. Iron deficiency affects more people than any other condition, constituting a public health condition of epidemic proportions. Iron overload disorders are less prevalent; however, they can lead to serious life-threatening conditions. Worldwide, some 24 million people of northern European ancestry suffer from a genetic disorder called hemochromatosis. Another 600 million carry one of the genes responsible for the disorder, and absorb up to 50% more iron than non-carriers. The disease leads to iron accumulation, particularly in the liver and other storage organs, which can cause organ failure (like cirrhosis of the liver), heart attack, cancer, and pancreatic damage.

Dysfunctions in iron metabolism pose a major problem worldwide due not only to their frequency but also to the lack of therapeutic options (N. C. Andrews, N. Engl. J. Med., 1999, 341: 1986-1995). Iron overload conditions are generally treated by administration of iron chelating agents, which exert their effects by remobilizing accumulated iron and allowing for its excretion. In practice, however, none of the chelating agents which have been evaluated to date have proved entirely satisfactory, suffering from poor gastrointestinal absorption, and either low efficacy, poor selectivity, or undesirable side effects. The preferred treatment for reducing iron levels in most hemochromatosis patients is called therapeutic phlebotomy, a procedure which simply consists of removing blood from the body. Patients with hemochromatosis usually need a large number of phlebotomies in a relative short period of time (up to once or twice a week). Thus, in addition to carrying the same risks as with any blood donation (e.g., nausea, vomiting, dizziness, fainting, hematoma, seizures or local infection), phlebotomy can also be highly constraining to the patient.

Several forms of iron salt are used to treat iron deficiency conditions. It generally takes several months of replacement therapy to replenish body iron stores. Some patients have difficulty tolerating iron salts, because these substances tend to cause gastrointestinal distress. Studies have also reported that liquid iron-salt preparations, given to young children, may cause permanent staining of the teeth. However, more problematic is the finding that high doses of iron supplements, taken orally or by injection, can increase susceptibility to bacterial infection.

Clearly, the development of novel agents and methods for the prevention and treatment of iron metabolism disorders, remains highly desirable.

SUMMARY OF THE INVENTION

The present invention provides improved systems and strategies for regulating iron metabolism in mammals, including humans. In particular, the invention encompasses reagents and processes for the treatment of conditions associated with iron deficiency or iron overload. The invention also provides screening tools and methods for the identification of compounds useful for the treatment of iron metabolism disorders. Compared to existing therapies such as iron supplementation, iron chelation, and phlebotomy, the inventive methods and compositions are less likely to induce undesirable side-effects.

In general, the present invention involves the use of modulators of the signaling activity of members of the TGF-β superfamily to control and/or regulate the expression or activity of hepcidin, a key regulator of iron metabolism in mammals.

More specifically, in one aspect, the present invention provides methods for regulating hepcidin expression or activity in a subject by administering to the subject an effective amount of a compound that modulates the signaling activity of at least one TGF-β superfamily member. The present invention also provides methods for regulating hepcidin expression or activity in a biological system by contacting the biological system with an effective amount of a compound that modulates the signaling activity of at least one TGF-β superfamily member. In certain embodiments, the TGF-β superfamily member is TGF-β or BMP. The compound administered to the subject or contacted with the biological system may comprise an agent selected from the group consisting of an agonist of TGF-β, an antagonist of TGF-β, an agonist of BMP, an antagonist of BMP, or combinations thereof. The biological system may be a cell, a biological fluid, a biological tissue or an animal.

In certain embodiments, the agent is selected from the group consisting of a HJV.Fc fusion protein, a Dragon.Fc fusion protein, a DLN.Fc fusion protein, a sTβRII.Fc fusion protein, a sTβRII-B.Fc fusion protein, and a sTβRIIIΔ.Fc fusion protein. In some embodiments, the agent comprises a fusion protein selected from the group consisting of a mutant HJV.Fc fusion protein, a mutant Dragon.Fc fusion protein and mutant DLN.Fc fusion protein, wherein the mutant fusion protein is non-proteolytically cleavable.

In methods for inhibiting hepcidin expression or activity in a subject or a biological system, the compound administered to the subject or contacted with the biological system is preferably an agonist of TGF-β, an antagonist of BMP, or combinations thereof. In methods for enhancing hepcidin expression or activity in a subject or a biological system, the compound administered to the subject or contacted with the biological system is preferably an antagonist of TGF-β, an agonist of BMP, or combinations thereof.

In another aspect, the present invention provides methods for regulating iron metabolism or an iron metabolic process' in a subject or a biological system by administering to the subject or contacting the biological system with an effective amount of a compound that modulates the signaling activity of at least one TGF-β superfamily member. The iron metabolic process may be iron uptake, iron absorption, iron transport, iron storage, iron processing, iron mobilization, iron utilization, or combinations thereof.

When the subject or biological system exhibits or is at risk of exhibiting iron deficiency, the compound used in these methods is preferably an agonist of TGF-β, an antagonist of BMP, or combinations thereof. When the subject or biological system exhibits or is at risk of exhibiting iron overload, the compound is, preferably, an antagonist of TGF-β, an agonist of BMP, or combinations thereof.

In still another aspect, the present invention provides methods for treating or preventing conditions associated with perturbations in iron metabolism in a subject. The inventive methods comprise administering to the subject an effective amount of a compound that modulates the signaling activity of at least one TGF-β superfamily member. In certain embodiments, the TGF-β superfamily member is TGF-β or BMP. In some embodiments, administration of the compound to the subject results in regulation of hepcidin expression or activity in the subject.

Compounds administered in the inventive methods may comprise an agent selected from the group consisting of an agonist of TGF-β, an antagonist of TGF-β, an agonist of BMP, an antagonist of BMP, or combinations thereof. In certain embodiments, the agent is selected from the group consisting of a HJV.Fc fusion protein, a Dragon.Fc fusion protein, a DLN.Fc fusion protein, a sTβRII.Fc fusion protein, a sTβRII-B.Fc fusion protein, and a sTβRIIIΔ.Fc fusion protein. In some embodiments, the agent comprises a fusion protein selected from the group consisting of a mutant HJV.Fc fusion protein, a mutant Dragon.Fc fusion protein and mutant DLN.Fc fusion protein, wherein the mutant fusion protein is non-proteolytically cleavable.

When the subject has or is at risk of having a condition associated with iron deficiency, the compound used in these methods is, preferably, an antagonist of BMP, an agonist of TGF-β, or combinations thereof. Conditions associated with iron deficiency that can be treated and/or prevented by methods of the present invention include, but are not limited to, anemia of chronic disease, iron deficiency anemia, functional iron deficiency, and microcytic anemia. In certain embodiments, the methods further comprise administering an iron supplementation treatment to the subject.

When the subject has or is at risk of having a condition associated with iron overload, the compound used in the methods of treatment is, preferably, an agonist of BMP, an antagonist of TGF-β, or combinations thereof. Conditions associated with iron overload that can be treated and/or prevented by methods of the present invention include, but are not limited to, adult hemochromatosis and juvenile hemochromatosis. In certain embodiments, the methods further comprise administering an iron chelation treatment to the subject. In some embodiments, the methods further comprise performing phlebotomy to the subject.

In yet another aspect, the present invention provides methods for identifying compounds that regulate hepcidin expression or activity in a biological system, and methods for identifying compounds that regulate iron metabolism or an iron metabolic process in a biological system. In these methods, the biological system preferably expresses at least one TGF-β superfamily member.

These methods comprise incubating the biological system with a candidate compound under conditions and for a time sufficient for the candidate compound to modulate the signaling activity of the TGF-β superfamily member; thereby obtaining a test system; measuring, in the test system, at least one factor that is representative of the signaling activity of the TGF-β superfamily member; incubating the system under the same conditions and for the same time absent the candidate compound, thereby obtaining a control system; measuring the factor in the control system; comparing the factor measured in the test and control systems; and determining that the candidate compound regulates hepcidin expression or iron metabolism in the system, if the factor measured in the test system is less than or greater than the factor measured in the control system.

In certain embodiments, the TGF-β superfamily member is TGF-β or BMP, and the compound identified as regulator is selected from the group consisting of an agonist of TGF-β, an antagonist of TGF-β, an agonist of BMP, and an antagonist of BMP. In some embodiments, the agent comprises a fusion protein selected from the group consisting of a mutant HJV.Fc fusion protein, a mutant Dragon.Fc fusion protein and mutant DLN.Fc fusion protein, wherein the mutant fusion protein is non-proteolytically cleavable.

The present invention also provides pharmaceutical compositions comprising a pharmaceutically acceptable carrier, and an effective amount of at least one regulator of iron metabolism or at least one regulator of hepcidin expression or activity identified by the inventive screening methods. Also provided are methods of using these identified regulators in the treatment or prevention of conditions associated with perturbations in iron metabolism.

BRIEF DESCRIPTION OF THE DRAWING

FIG. 12 is a table reporting measurements of serum iron and total iron binding capacity in mice after intraorbital treatment with BMP-2 ligand.

FIG. 17 shows a table summarizing genetic analysis of kindreds affected with juvenile hemochromatosis. Haplotype data in ten Greek families with juvenile hemochromatosis. Genotypes are shown for 27 informative markers from the 1p13-q23 genetic interval in the indicated individuals, with each of the consensus haplotypes shaded in a different color. Markers designated 'D1S' are described in build 33 of the human genome, and newly generated microsatellite markers are designated by repeat type and human genomic clone accession numbers. ND indicates genotypes that were not determined. Alleles of uncertain phase are underlined, inferred alleles are italicized and alleles observed most frequently in 56 Greek control chromosomes are shown in bold. Marker order is based on a revised interpretation of the April 2003 build 33 of the human genome assembly. The red bar indicates the critical interval associated with juvenile hemochromatosis.

DEFINITIONS

Figure 1:
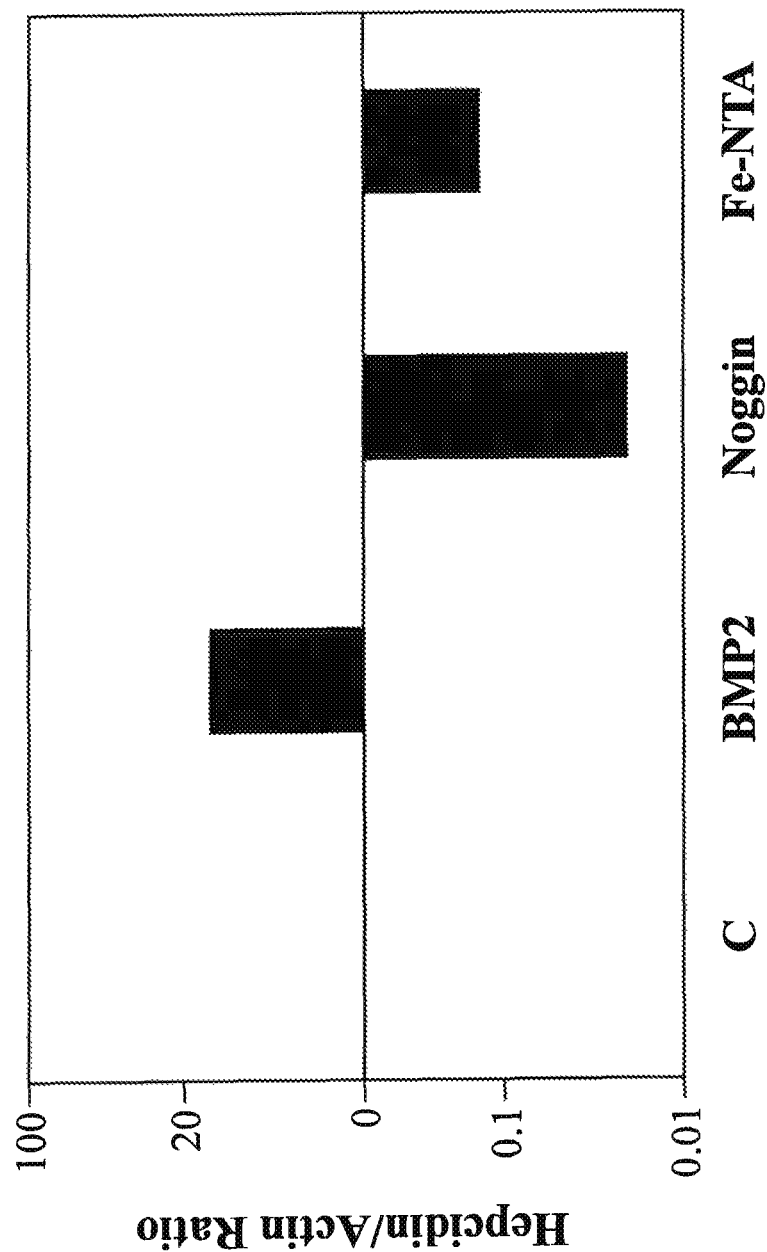
FIG. 1 is a graph showing the effects of BMP-2, Noggin.Fc (which is known to inhibit endogenous BMP signaling), and Fe-NTA (non-transferrin-bound iron) on the hepcidin/actin ratio in HepG2 cells compared to the hepcidin/actin ratio in control cells, C (i.e., HepG2 cells incubated in the absence of these agents).

Throughout the specification, several terms are employed that are defined in the following paragraphs.

As used herein, the term "a TGF-β superfamily member" refers to any member of the TGF-β superfamily, which includes, among others, activins, inhibins, Transforming Growth Factors beta (TGF-βs), Growth and Differentiation Factors (GDFs), Bone Morphogenetic Proteins (BMPs), and Müllerian Inhibiting Substance (MIS). In the context of the present invention, certain preferred TGF-β superfamily members include TGF-βs and BMPs.

The term "perturbations" when applied to iron metabolism or an iron metabolic process, refers to any disturbances, dysregulations and/or deviations from normal state, function and/or level of activity. Iron metabolic processes include iron uptake, iron absorption, iron transport, iron storage, iron processing, iron mobilization, and iron utilization. Generally, perturbations in iron metabolism result in iron overload or iron deficiency. As used herein, the term "iron overload" refers to an amount of iron present in a subject's tissue or in a biological system which is significantly above the normal level in that particular tissue or that particular biological system. The term "iron deficiency" refers to an amount of iron present in a subject's tissue or in a biological system which is significantly below the normal level in that particular tissue or that particular biological system. An amount of iron significantly below or significantly above the normal level corresponds to any amount of iron that is physiologically undesirable and/or that is or may become harmful to the subject or the biological system. Methods for the determination of iron levels are known in the art (see below).

As used herein, the term "condition associated with perturbations of iron metabolism or an iron metabolic process" refers to any disease, disorder, syndrome or condition that is characterized by iron overload or iron deficiency.

The term "prevention" is used herein to characterize a method that is aimed at delaying or preventing the onset of a pathophysiological condition associated with perturbations in iron metabolism (for example in a subject which may be predisposed to the condition but has not yet been diagnosed as having it).

The term "treatment" is used herein to characterize a method that is aimed at (1) delaying or preventing the onset of a condition associated with perturbations in iron metabolism; or (2) slowing down or stopping the progression, aggravation, or deterioration of the symptoms of the condition; or (3) bringing about ameliorations of the symptoms of the condition; or (4) curing the condition. A treatment may be administered prior to the onset of the disease, for a prophylactic or preventive action. It may also be administered after initiation of the disease, for a therapeutic action.

The terms "compound" and "agent" are used herein interchangeably. They refer to any naturally occurring or non-naturally occurring (i.e., synthetic or recombinant) molecule, such as a biological macromolecule (e.g., nucleic acid, polypeptide or protein), organic or inorganic molecule, or an extract made from biological materials such as bacteria, plants, fungi, or animal (particularly mammalian, including human) cells or tissues. The compound may be a single molecule, a mixture of two or more molecules, or a complex of at least two molecules.

The term "candidate compound" refers to a compound or agent (as defined above) that is to be tested for an activity of interest. In certain screening methods of the invention, candidate compounds are evaluated for their ability to regulate hepcidin expression and/or to regulate iron metabolism through modulation of the signaling activity of a TGF-β superfamily member.

The term "regulation" when applied to a biological phenomenon (such as iron metabolism, and hepcidin expression or activity) refers to a process that allows for control of the biological phenomenon. The term "regulation" also refers to the ability of a compound to control the biological phenomenon. For example, a process or a compound that regulates iron metabolism has the ability to decrease iron levels in a subject or biological system that exhibits iron overload; and/or the ability to increase iron levels in a subject or biological system that exhibits iron deficiency. In the context of the present invention, the mechanism by which regulation of the biological phenomenon takes place is preferably through modulation of the signaling activity of a TGF-β superfamily member. In the screening methods of the invention, when a candidate compound is found to regulate hepcidin expression or activity, it is identified as a "regulator" of the expression or activity of hepcidin.

As used herein, the term "modulation of the signaling activity of a TGF-β superfamily member" refers to the ability of a compound to increase or prolong, or to decrease or reduce the duration of the effect of a TGF-β superfamily member. In the screening methods of the invention, when a candidate compound is found to induce such an enhancement or inhibition, it is identified as a "modulator" of the signaling activity of the TGF-β superfamily member.

The term "agonist" is intended to be used as is accepted in the art. In general, the term refers to a compound that increases or prolongs the duration of the effect of a polypeptide or a nucleic acid. An agonist may be a direct agonist, in which case it is a molecule that exerts its effect by interacting with (e.g., binding to) the polypeptide or nucleic acid, or an indirect agonist, in which case it exerts its effect via a mechanism other than by interaction with the polypeptide or nucleic acid (e.g., by altering the expression or stability of the polypeptide or nucleic acid, by altering the expression or activity of a target of the polypeptide or nucleic acid, by interacting with an intermediate in a pathway involving the polypeptide or nucleic acid, etc.).

The term "antagonist" is intended to be used as is accepted in the art. In general, the term refers to a compound that decreases or reduces the duration of the effect of a polypeptide or a nucleic acid. An antagonist may be a direct antagonist, in which case it is a molecule that exerts its effect by interacting with (e.g., binding to) the polypeptide or nucleic acid, or an indirect antagonist, in which case it exerts its effect via a mechanism other than by interaction with the polypeptide or nucleic acid (e.g., by altering the expression or stability of the polypeptide or nucleic acid, by altering the expression or activity of a target of the polypeptide or nucleic acid, by interacting with an intermediate in a pathway involving the polypeptide or nucleic acid, etc.).

As used herein, the term "effective amount" refers to any amount of a compound or agent that is sufficient to fulfill its intended purpose(s). In the context of the present invention, the purpose(s) may be, for example: to modulate the signaling activity of a TGF-β superfamily member; and/or to regulate hepcidin expression or activity; and/or to regulate iron metabolism or an iron metabolic process; and/or to delay or prevent the onset of a condition associated with perturbations in iron metabolism; and/or to slow down or stop the progression, aggravation, or deterioration of the symptoms of the condition; and/or to bring about ameliorations of the symptoms of the condition; and/or to cure the condition.

The term "subject" refers to a human or another mammal, that can be affected by a pathophysiological condition associated with perturbations in iron metabolism but may or may not have such a condition.

The terms "system" and "biological system" are used herein interchangeably. A system may be any biological entity that can exhibit iron overload or iron deficiency. The biological system is preferably one that expresses at least one TGF-β superfamily member. Some preferred systems express TGF-β and/or BMP. The biological system may also preferably express hepcidin or comprise hepcidin. In the context of this invention, in vitro, in vivo, and ex vivo systems are considered; and the system may be a cell, a biological fluid, a biological tissue, or an animal. A system may, for example, originate from a live subject (e.g., it may be obtained by drawing blood, or by biopsy), or from a deceased subject (e.g., it may be obtained at autopsy).

As used herein, the term "biological fluid" refers to a fluid produced by and obtained from a subject. Examples of biological fluids include, but are not limited to, urine, blood serum, and plasma. In the present invention, biological fluids include whole or any fraction of such fluids derived by purification, for example, by ultra-filtration or chromatography. As used herein, the term "biological tissue" refers to a tissue obtained from a subject. The biological tissue may be whole or part of any organ or system in the body (e.g., liver, gastrointestinal tract, kidney, pancreas, and the like).

A "pharmaceutical composition" is defined herein as comprising at least one compound of the invention (i.e., a candidate compound identified by an inventive screening method as a regulator of iron metabolism, and/or a regulator of hepcidin expression or activity), and at least one pharmaceutically acceptable carrier.

As used herein, the term "pharmaceutically acceptable carrier" refers to a carrier medium which does not interfere with the effectiveness of the biological activity of the active ingredients and which is not excessively toxic to the hosts at the concentrations at which it is administered. The term includes solvents, dispersion media, coatings, antibacterial and antifungal agents, isotonic agents, absorption delaying agents, and the like. The use of such media and agents for the formulation of pharmaceutically active substances is well known in the art (see, for example, Remington's Pharmaceutical Sciences, E. W. Martin, 18$^{th}$ Ed., 1990, Mack Publishing Co., Easton, Pa.).

DETAILED DESCRIPTION OF CERTAIN PREFERRED EMBODIMENTS

As mentioned above, the present invention provides improved systems and strategies for regulating iron metabolism in mammals. In particular, the inventive compounds and methods are less likely than existing therapies to induce undesirable side effects.

I. Agonists and Antagonists of TGF-β Superfamily Members as Regulators of Iron Metabolism The present invention encompasses the discovery that certain members of the TGF-β superfamily can regulate the expression of hepcidin, a key regulator of iron metabolism in mammals. As described in Example 1, the present Applicants have recognized that BMP (bone morphogenetic protein) signaling induces hepcidin expression in HepG2 liver hepatoma cells, while TGF-β (Transforming Growth Factor-beta) signaling inhibits the expression of hepcidin. Furthermore, using Noggin, a well-known BMP antagonist, the Applicants have shown that inhibition of BMP signaling resulted in reduction of hepcidin expression.

Accordingly, the present invention provides methods of using agonists and/or antagonists of members of the TGF-β superfamily to regulate hepcidin expression or activity, which, in turn, regulates iron metabolism.

A—Hepcidin

Hepcidin is a small, cysteine-rich cationic peptide with antimicrobial properties that was purified only recently from human urine and plasma ultra-filtrate (C. H. Park et al., J. Biol. Chem., 2001, 276: 7806-7810; A. Krause et al., FEBS Lett., 2000, 480: 147-150). This peptide of 20, 22 or 25 amino acids, differing by amino acid terminal truncation, forms a short hairpin with two arms linked by four disulfide bridges in a ladder-like fashion. Hepcidin contains eight cysteine residues that are conserved among species (G. Nicolas et al., Proc. Natl. Acad. Sci. USA, 2001, 98: 878-885; C. Pigeon et al., J. Biol. Chem., 2001, 276: 7811-7819). Even though the peptide was first isolated from urine and blood, hepcidin is predominantly expressed in the liver in both mice and humans. Expression is also detectable in the heart and brain, but to a much less extent (C. H. Park et al., 2001; C. Pigeon et al., 2001). Recently, hepcidin has also been found to be expressed in the kidney (H. Kulaksiz et al., J. Endocrinol., 2005, 184: 361-370).

Only one copy of the gene exists in humans, whereas two hepcidin genes (Hepc 1 and Hepc 2) have been reported in mice (G. Nicolas et al., Proc. Natl. Acad. Sci. USA, 2001, 98: 878-885; C. Pigeon et al., J. Biol. Chem., 2001, 276: 7811-7819). Both the human and mouse hepcidin genes consist of three exons and two introns, with the third exon encoding the mature peptide found in urine. In humans and rats, the exons encode an 84 (83 in mice) amino acid precursor, including a putative 24 amino acid signal peptide.

The connection between hepcidin and iron metabolism was first made by Pigeon et al. (J. Biol. Chem., 2001, 276: 7811-7819) while investigating hepatic responses to iron overload. Other studies have shown that mice lacking hepcidin mRNA developed iron overload affecting liver and pancreas, with deficit in the macrophage-rich spleen (G. Nicolas et al., Proc. Natl. Acad. Sci. USA, 2001, 98: 8780-8785). Transgenic mice overexpressing hepcidin were observed to die at birth of severe iron deficiency (G. Nicolas et al., Proc. Natl. Acad. Sci. USA, 2002, 99: 4596-4601). These studies suggested that hepcidin inhibits iron absorption in the small intestine, the release of recycled iron from macrophages (R. E. Fleming and W. S. Sly, Proc. Natl. Acad. Sci. USA, 2001, 98: 8160-8162), and transport of iron across the placenta (G. Nicolas et al., Proc. Natl. Acad. Sci. USA, 2002, 99: 4596-4601). In agreement with animal studies, patients with large hepatic adenomas and otherwise unexplained iron refractory anemia exhibit overexpressed hepcidin mRNA in the liver (D. A. Weinstein et al.; Blood, 2002, 100: 3776-3781). Recent studies have found abnormal hepcidin expression and disrupted hepcidin regulation (K. R. Bridle et al., Lancet, 2003, 361: 669-673; H. Kulaksiz et al., Gut, 2004, 53: 735-743) in hemochromatosis gene (HFE)-associated hemochromatosis and association of hepcidin mutations with severe juvenile hemochromatosis (A. Roetto et al., Nature Genetics, 2003, 33: 21-22). Based on these and other observations, it has been suggested that hepcidin is a key component of iron homeostasis that acts as a negative regulator of iron metabolism.

B—TGF-β Superfamily Members

The TGF-β superfamily of ligands presently comprises more than 30 members, including, among others, activins, inhibins, Transforming Growth Factors-beta (TGF-βs), Growth and Differentiation Factors (GDFs), Bone Morphogenetic Proteins (BMPs), and Müllerian inhibiting Substance (MIS). All of these molecules are peptide growth factors that are structurally related to TGF-β. They all share a common motif called a cysteine knot, which is constituted by seven especially conservative cysteine residues organized in a rigid structure (J. Massagué, Annu. Rev. Biochem., 1998, 67: 753-791). Unlike classical hormones, members of the TGF-β superfamily are multifunctional proteins whose effects depend on the type and stage of the target cells as much as the growth factors themselves.

TGF-β superfamily members suitable for use in the practice of the methods of the present invention include any member of the TGF-β superfamily whose signaling activity can regulate the expression or activity of hepcidin. Preferred TGF-β superfamily members include, but are not limited to, TGF-βs and BMPs.

Transforming Growth Factors-Beta (TGF-βs)

In certain embodiments of the invention, the TGF-β superfamily member is TGF-β. TGF-βs are extracellular polypeptides that are implicated in a broad range of biological processes (J. Massagué, Ann. Rev. Cell. Biol., 1990, 6: 597-641) and play a central role in key events during embryogenesis, adult tissue repair, and immunosuppression (M. B. Sporn and A. B. Roberts, J. Cell. Biol. 1992, 119: 1017-1021; S. W. Wahl, J. Clin. Immunol. 1992, 12: 61-74; D. M. Kingsley, Genes Dev. 1994, 8: 133-146). In mammals, TGF-β is produced by almost all cells of the organism, and almost all cells can serve as targets for its effects. TGF-β is a potent regulator of cell proliferation, cell differentiation, apoptosis, and extracellular matrix production.

Mammalian cells can produce three different isoforms of TGF-β: TGF-β1, TGF-β2, and TGF-β3. These isoforms exhibit the same basic structure (they are homodimers of 112 amino acids that are stabilized by intra- and inter-chain disulfide bonds) and their amino acid sequences present a high degree of homology (>70%). However, each isoform is encoded by a distinct gene, and each is expressed in both a tissue-specific and developmentally regulated fashion (J. Massagué, Annu. Rev. Biochem. 1998, 67: 753-791). According to modern concepts, TGF-β exerts its effects by first binding to membrane receptors on the target cell, thereby initiating downstream signaling events. Cross-linking studies have shown that TGF-β mainly binds to three high-affinity cell-surface proteins, called TGF-β receptors of type I, type II, and type III (J. Massagué and B. Like, J. Biol. Chem. 1985, 260: 2636-2645; S. Cheifetz et al., J. Biol. Chem. 1986, 261: 9972-9978).

Regulation of iron metabolism according to methods of the present invention may be achieved by inhibition or enhancement of the signaling activity of any one of the isoforms of TGF-β (i.e., TGF-β1, TGF-β2, and TGF-β3) as long as this inhibition or enhancement results in regulation of hepcidin expression or activity.

Bone Morphogenetic Proteins (BMPs)

In other embodiments of the present invention, the TGF-β superfamily member is BMP. BMPs were originally identified as proteins that induce bone formation at ectopic (i.e., non-skeletal) sites (A. H. Reddi, Curr. Opin. Genet. Dev., 1994, 4: 737-744). However, it is now clear that in addition to their roles in bone and cartilage morphogenesis, BMPs are also involved in prenatal development and postnatal growth and/or repair of the eye, heart, blood, lung, kidney, muscle, skin, and other tissues (K. A. Waite and C. Eng, Nat. Rev. Genet., 2003, 4: 763-773). Studies have shown that BMPs play an important role in regulating proliferation, apoptosis, differentiation, and chemotaxis of various cell types, including mesenchymal cells, epithelial cells, hematopoietic cells and neuronal cells. (J. Massagué and Y. G. Chen, Genes Dev., 2000, 14: 627-644; K. Miyazono et al., J. Cell Physiol., 2001, 187: 265-276: N. Morrell et al., Circulation, 2001, 104: 790-795; A. von Budnoff and K. W. Y. Cho, Dev. Biol., 2001, 239: 1-14).

In a manner similar to other members of the TGF-β superfamily, BMPs mediate their effects by forming a complex of two different types of transmembrane serine/threonine kinase receptors: type I and type II (C. H. Heldin et al., Nature, 1997, 390: 465-471; J. Newman et al., N. Engl. J. Med., 2001, 345: 319-324; B. L. Rosenzweig et al., Proc. Natl. Acad. Sci. USA, 1995, 92: 7632-7636). Three different BMP type I receptors (activin receptor-like kinase ALK2, ALK3, and ALK6) and three BMP type II receptors (BMP type II receptor (BMPRII); Activin type IIA receptor (ActRIIA); and Activin type BB receptor (ActRIIB)) have been identified (L. Attisano and J. L. Wrana, Science, 2002, 296: 1646-1647). BMP binding induces phosphorylating of the type I receptor by the type II receptor, which leads to phosphorylation of cytoplasmic receptor-activated Smads (C. H. Heldin et al., Nature, 1997, 390: 465-471).

To date, nearly 20 BMP isoforms have been identified and characterized in mammals and newer ones are being discovered (M. Kawabata et al., Cytokine Growth Factor Rev., 1998, 9: 49-61). The BMP family members have been classified in subgroups according to how closely they are related to each other structurally (T. Sakou, Bone, 1998, 22: 591-603; R. G. Schaub and J. Wozney, Curr. Opin. Biotechnol., 1991, 2: 868-871; J. M. Schmitt et al., J. Orthop. Res., 1999, 17: 269-278). In vivo, the BMP isoforms have different profiles of expression, different affinities for receptors and therefore unique biological activities.

Regulation of iron metabolism according to methods of the present invention may be achieved by inhibition or enhancement of the signaling activity of any one of the isoforms of BMP as long as this inhibition or enhancement results in regulation of hepcidin expression or activity.

C—Agonists and Antagonists of TGF-β Superfamily Members

Agonists and antagonists of a TGF-β superfamily member suitable for use in the methods of the present invention include any compound or agent that has the ability to modulate (i.e., enhance or inhibit) the signaling activity of the TGF-β superfamily member such that this modulation results in regulation of hepcidin expression or activity.

Suitable agonists and antagonists include naturally-occurring agonists and antagonists of the TGF-β superfamily member (including fragments and variants thereof that retain the biological characteristics of the naturally-occurring agonist and antagonist ligands). Suitable agonists and antagonists also include synthetic or human recombinant compounds. Classes of molecules that can function as agonists include, but are not limited to, small molecules, antibodies (including fragments or variants thereof, such as Fab fragments, Fab'2 fragments and scFvs), and peptidomimetics. Classes of molecules that can function as antagonists include, but are not limited to, small molecules, antibodies (including fragments or variants thereof), fusion proteins, antisense polynucleotides, ribozymes, small interfering RNAs (sRNAi), and peptidomimetics.

As will be appreciated by those skilled in the art, any compound or agent that is identified, for example, by the inventive screening assays (described below), as a modulator of a TGF-β superfamily member is suitable for use in the practice of methods of the present invention. In particular, small molecules modulators that exhibit high specificity may be of value in these methods.

Agonists and Antagonists of BMPs

Various antagonists of BMPs are known in the art (see, for example, G. J. Thomsen et al., Trends Genet., 1997, 13: 209-211; E. Canalis et al., Endocr. Rev. 2003, 24: 218-235; V. A. Botchkarev, J. Invest. Dermatol., 2003, 120: 36-47; U.S. Pat. No. 6,432,410, each of which is incorporated herein by reference in its entirety). In particular, the effects of BMPs can be modulated by a group of secreted polypeptides that prevent BMP signaling by binding BMPs, thereby precluding their binding to specific cell surface receptors. BMP antagonists suitable for use in the practice of the present invention include, but are not limited to, Noggin, chordin, ventroptin, follistatin and follistatin-related gene (FLRG). Other suitable BMP antagonists include cerberus, gremlin, caronte, DAN, Dante, and sclerostin and other structurally related proteins, which are collectively termed the DAN family (D. Hsu et al., Mol. Cell, 1998, 1: 673-683, which is incorporated herein by reference in its entirety). Proteins of the DAN family have a conserved cysteine-knot motif, which is also found in other growth factors, including TGF-β-like factors (J. J. Pearce et al., Dev. Biol., 1999, 209: 98-110; C. R. Rodrigez Esteban et al., Nature, 1999, 401: 243-251). However, other BMP antagonists lack sequence similarity with each other. In vivo, these BMP antagonists have distinct expression profiles, different affinities for various BMP isoforms, and regulate different biological responses.

The present invention also provides other BMP antagonists. As reported in Example 2, hemojuvelin (HJV) is a member of the repulsive guidance molecule (RGM) family of proteins. Individuals with HJV mutations are known to exhibit depressed levels of hepcidin. The present Applicants have shown that HJV enhances BMP but not TGF-β signaling. The results they obtained demonstrate that HJV binds directly to BMP-2; and that the enhancing effect of HJV on BMP signaling is reduced by administration of Noggin, indicating that HJV's action is ligand-dependent. Accordingly, a family of soluble HJV.Fc fusion proteins is provided herein as BMP antagonists suitable for use in the practice of the present invention.

The present Applicants have recently reported (T. A. Samad et al., "DRAGON: a bone morphogenetic protein co-receptor", J. Biol. Chem., 2005, 280: 14122-14129, which is incorporated herein by reference in its entirety) that DRAGON, a 436 amino acid glycosylphosphatidylinositol (GPI)-anchored member of the RGM family, which is expressed early in the developing nervous system, enhances BMP but not TGF-β signaling and acts as a BMP co-receptor. Accordingly, the present invention provides a family of soluble DRAGON.Fc fusion proteins as BMP antagonists suitable for use in the inventive methods. An example of a DRAGON.Fc fusion protein that can be used in the practice of the present invention has been described by the present Applicants (T. A. Samad et al., "DRAGON: A member of the repulsive guidance molecule-related family of neuronal- and muscle-expressed membrane proteins is regulated by DRG11 and has neuronal adhesive properties", J. Neuroscience, 2004, 24: 2027-2036, which is incorporated herein by reference in its entirety). Soluble DRAGON.Fc fusion protein has been found to bind selectively to BMP-2 and BMP-4, but not to BMP-7 or other members of the TGF-β superfamily of ligands (T. A. Samad et al., J. Biol. Chem., 2005, 280: 14122-14129).

Also provided herein is a family of RGMa.Fc (or DLN.Fc) fusion proteins as BMP antagonists suitable for use in the practice of the present invention. Like DRAGON, RGMa is a member of the repulsive guidance molecule (RGM) family of genes. RGMa and DRAGON are expressed in a complementary manner in the central nervous systems, where RGMa mediates repulsive axonal guidance and neural tube closure, while DRAGON contributes to neuronal cell adhesion through homophilic interactions. The present Applicants have shown that RGMa enhances BMP, but not TGF-β, signals in a ligand-dependent manner in cell culture and that the soluble extracellular domain of RGMa fused to human Fc (RGMa.Fc or DLN.Fc) forms a complex with BMP type 1 receptors and binds directly and selectively to radiolabeled BMP-2 and BMP-4 (J. L. Babitt et al., "Repulsive guidance molecule (RGMa), a DRAGON homologue, is a bone morphogenetic protein co-receptor", J. Biol. Chem., 2005, 280: 29820-29827, which is incorporated herein by reference in its entirety)

The present invention also provides mutant HJV, RGMa and DRAGON fusion proteins. In particular, mutant HJV, RGMa and DRAGON fusion proteins are provided that are more stable to proteolytic cleavage than the corresponding wild-type versions. It is known in the art that HJV, RMGa and DRAGON share a consensus proteolytic cleavage site. For human HJV, the cleavage site is situated after aspartic acid residue 172 (G. Papanikolaou et al., Nature Genetics, 2004, 36: 77-82, which is incorporated herein by reference in its entirety); for human DRAGON, after aspartic acid residue 168 (T A. Samad et al., J, Neuroscience, 24: 2027-2036, which is incorporated herein by reference in its entirety); and for human RGMa, after aspartic acid residue 168 (Genbank Sequence #NM 020211).

Mutant HJV, RGMa and DRAGON fusion proteins of the present invention contain one mutation or more than mutation that confers stability to the fusion protein, in particular stability to proteolytic cleavage. For example, the aspartic acid residue situated close to the cleavage site may be substituted by a different residue or deleted. Alternatively or additionally, a residue in the vicinity of the cleavage site may be substituted by a different residue or deleted. Methods that allow specific mutations or mutations in specific portions of a polynucleotide sequence that encodes an isolated polypeptide to provide variants are known in the art. The present Applicants have demonstrated the feasibility of producing mutant HJV, RGMa, and DRAGON proteins that are not proteolytically cleaved, as reported in Example 4.

Agonists and Antagonists of TGF-βs

Multiple naturally-occurring modulators have been identified that enhance or inhibit TGF-β signaling. Access of TGF-β ligands to receptors is inhibited by the soluble proteins LAP, decorin and a2-macroglobulin that bind and sequester the ligands (W. Balemans and W. Van Hul, Dev. Biol., 2002, 250: 231-250). TGF-β ligand access to receptors is also controlled by membrane-bound receptors. BAMBI acts as a decoy receptor, competing with the type I receptor (D. Onichtchouk et al., Nature, 1999, 401: 480-485); betaglycan (TGF-β type II receptor) enhances TGF-β binding to the type II receptor (C. B. Brown et al., Science, 1999, 283: 2080-2082; J. Massagué, Annu. Rev. Biochem., 1998, 67: 753-791; E. del Re et al., J. Biol. Chem., 2004, 279: 22765-22772); and endoglin enhances TGF-β binding to ALK1 in endothelial cells (D. A. Marchuk, Curr. Opin. Hematol., 1998, 5: 332-338; J. Massagué, Nat. Rev. Mol. Cell Biol., 200, 1: 169-178; Y. Shi and J. Massagué, Cell, 2003, 113: 685-700). Cripto, an EGF-CFC GPI-anchored membrane protein, acts as a co-receptor, increasing the binding of the TGF-β ligands, nodal, Vg1, and GDF1 to activin receptors (S. K. Cheng et al., Genes Dev., 2003, 17: 31-36; M. M. Shen and A. F. Schier, Trends Genet., 2000, 16: 303-309) while blocking activin signaling.

Thus, agonists and antagonists of TGF-β signaling suitable for use in the practice of the methods of the present invention include naturally-occurring TGF-β antagonists (e.g., decorin, see, for example, Y. Yamaguchi et al., Nature, 1990, 346: 281-284, which is incorporated herein by reference in its entirety); soluble forms of naturally-occurring TGF-β agonists (e.g., a soluble form of endoglin, see, for example, U.S. Pat. Nos. 5,719,120; 5,830,847; and 6,015,693, each of which is incorporated herein by reference in its entirety); as well as inhibitors of naturally-occurring TGF-β antagonists.

Other suitable TGF-β antagonists include antagonists that have been developed to suppress undesired effects of TGF-βs for therapeutic purposes. For example, anti-TGF-β antibodies, whose dissociation constants have been reported to be in the nanomolar range have been described (U.S. Pat. No. 5,571,714, which is incorporated herein by reference in its entirety). These anti-TGF-β antibodies have been successfully administered to animals with diverse pathological conditions (W. A. Broder et al., Nature, 1990, 346: 371-374; S. W. Wahl, J. Clin. Immunol. 1992, 12: 61-74; M. Shah et al., Lancet, 1992, 339: 213-214; M. S. Steiner and E. R. Barrack, Mol. Endocrinol. 1992, 6: 15-25; F. N. Ziyadeh et al., Proc. Natl. Acad. Sci. USA, 2000, 97: 8015-8020).

Other TGF-β inhibitors have been developed based on an in vitro study, which showed that adenovirus-mediated transfer of a truncated TGF-β type II receptor completely and specifically abolishes diverse TGF-β signaling (H. Yamamoto et al., J. Biol. Chem. 1996, 271: 16253-16259, which is incorporated herein by reference in its entirety). Several of these truncated receptors possess potent antagonistic activity against their ligands by acting as dominant-negative mutants (A. Bandyopadhyay et al., Cancer Res. 1999, 59: 5041-5046; Z. Qi et al., Proc. Natl. Acad. Sci. USA, 1999, 96: 2345-2349; T. Nakamura et al., Hepatol. 2000, 32: 247-255, each of which is incorporated herein by reference in its entirety).

Soluble forms of TGF-β type II receptor (Sakamoto et al., Gene Ther. 2000, 7: 1915-1924; H. Ueno et al., Gene Ther. 2000, 11: 33-42; J. George et al., Proc. Natl. Acad. Sci. USA, 1999, 96: 12719-12724, each of which is incorporated herein by reference in its entirety) and type III receptor (PCT application No. PCT/US2004/014175 to the present Applicants, which is incorporated herein by reference in its entirety) have also been produced as fusion proteins and have successfully been used to prevent or treat TGF-β-related pathophysiological conditions in animal models.

II. Identification of Regulators of Iron Metabolism

In another aspect, the present invention provides methods for the identification of compounds that regulate iron metabolism by modulating the signaling activity of a TGF-β superfamily member. The present invention also provides methods for the identification of compounds that regulate hepcidin expression or activity by modulating the signaling activity of a TGF-β superfamily member.

Preferably, these methods comprise incubating a biological system, which expresses at least one TGF-β superfamily member, with a candidate compound under conditions and for a time sufficient for the candidate compound to modulate the signaling activity of the TGF-β superfamily member, thereby obtaining a test system; incubating the biological system under the same conditions and for the same time absent the candidate compound, thereby obtaining a control system; measuring, in the test system, at least one factor that is representative of the signaling activity of the TGF-β superfamily member, measuring the factor in the control system; comparing the factor measured in the test and control systems; and determining that the candidate compound regulates hepcidin expression (and/or regulates iron metabolism), if the factor measured in the test system is less than or greater than the factor measured in the control system.

The screening methods provided herein will lead to the discovery and development of regulators of iron metabolism and regulators of hepcidin expression or activity that exert their effects by modulating the signaling activity of one or more TGF-β superfamily members. These regulators may be potentially useful in the treatment of conditions associated with perturbations in iron metabolism.

A—Biological Systems

The assay and screening methods of the present invention may be carried out using any type of biological systems, i.e., a cell, a biological fluid, a biological tissue, or an animal. In certain embodiments, the system is a biological entity that can exhibit iron deficiency or iron overload (e.g., an animal model, a blood sample, or whole or part of an organ, e.g., the liver); and/or a biological entity that expresses at least one TGF-β family member (e.g., a cell); and/or a biological entity that expresses hepcidin (e.g., a hepatocyte) or comprises hepcidin (e.g., a blood or urine sample).

In certain embodiments, the assay and screening methods of the present invention are carried out using cells that can be grown in standard tissue culture plastic ware. Such cells include all normal and transformed cells derived from any recognized sources. Preferably, cells are of mammalian (human or animal, such as rodent or simian) origin. More preferably, cells are of human origin. Mammalian cells may be of any organ or tissue origin (e.g., brain, liver, blood, or kidney) and of any cell types. Suitable cell type include, but are not limited to, epithelial cells, platelets, lymphocytes, monocytes, myocytes, macrophages, hepatocytes, cardiomyocytes, endothelial cells, tumor cells, and the like.

Cells to be used in the practice of the assays and screening methods of the present invention may be primary cells, secondary cells, or immortalized cells (e.g., established cell lines). They may be prepared by techniques well known in the art (for example, cells may be obtained by drawing blood from a patient or a healthy donor) or purchased from immunological and microbiological commercial resources (for example, from the American Type Culture Collection, Manassas, Va.). Alternatively or additionally, cells may be genetically engineered to contain, for example, a gene of interest such as a gene expressing a growth factor or a receptor.

Selection of a particular cell type and/or cell line to perform an assay according to the present invention will be governed by several factors such as the nature of the TGF-β superfamily member whose signaling activity is to be modulated and the intended purpose of the assay. For example, an assay developed for primary drug screening (i.e., first round(s) of screening) may preferably be performed using established cell lines, which are commercially available and usually relatively easy to grow, while an assay to be used later in the drug development process may preferably be performed using primary or secondary cells, which are often more difficult to obtain, maintain, and/or to grow than immortalized cells but which represent better experimental models for in vivo situations.

Examples of established cell lines that can be used in the practice of the assays and screening methods of the present invention include HepG2 liver hepatoma cells, Hep3B liver hepatoma cells, primary hepatocytes, and immortalized hepatocytes. Primary and secondary cells that can be used in the inventive screening methods, include, but are not limited to, epithelial cells, platelets, lymphocytes, monocytes, myocytes, macrophages, hepatocytes, cardiomyocytes, endothelial cells, and tumor cells.

Cells to be used in the inventive assays may be cultured according to standard cell culture techniques. For example, cells are often grown in a suitable vessel in a sterile environment at 37° C. in an incubator containing a humidified 95% air-5% $CO_2$ atmosphere. Vessels may contain stirred or stationary cultures. Various cell culture media may be used including media containing undefined biological fluids such as fetal calf serum. Cell culture techniques are well known in the art and established protocols are available for the culture of diverse cell types (see, for example, R. I. Freshney, "*Culture of Animal Cells: A Manual of Basic Technique*", 2nd Edition, 1987, Alan R. Liss, Inc.).

In certain embodiments, the screening methods are performed using cells contained in a plurality of wells of a multi-well assay plate. Such assay plates are commercially available, for example, from Stratagene Corp. (La Jolla, Calif.) and Corning Inc. (Acton, Mass.) and include, for example, 48-well, 96-well, 384-well and 1536-well plates.

B—Candidate Compounds

As will be appreciated by those of ordinary skill in the art, any kind of compounds or agents can be tested using the inventive methods. A candidate compound may be a synthetic or natural compound; it may be a single molecule, or a mixture or complex of different molecules. In certain embodiments, the inventive methods are used for testing one or more compounds. In other embodiments, the inventive methods are used for screening collections or libraries of compounds. As used herein, the term "collection" refers to any set of compounds, molecules or agents, while the term "library" refers to any set of compounds, molecules or agents that are structural analogs.

Traditional approaches to the identification and characterization of new and useful drug candidates generally include the generation of large collections and/or libraries of compounds followed by testing against known or unknown targets (see, for example, WO 94/24314; WO 95/12608; M. A. Gallop et al., J. Med. Chem. 1994, 37: 1233-1251; and E. M. Gordon et al., J. Med. Chem. 1994, 37: 1385-1401). Both natural products and chemical compounds may be tested by the methods of the invention. Natural product collections are generally derived from microorganisms, animals, plants, or marine organisms; they include polyketides; non-ribosomal peptides, and/or variants thereof (for a review, see, for example, D. E. Cane et al., Science, 1998, 82: 63-68). Chemical libraries often consist of structural analogs of known compounds or compounds that are identified as hits or leads via natural product screening. Chemical libraries are relatively easy to prepare by traditional automated synthesis, PCR, cloning or proprietary synthetic methods (see, for example, S. H. DeWitt et al., Proc. Natl. Acad, Sci. U.S.A. 1993, 90:6909-6913; R. N. Zuckennann et al., J. Med. Chem. 1994, 37: 2678-2685; Carell et al., Angew. Chem, Int. Ed. Engl. 1994, 33: 2059-2060; P. L. Myers, Curr. Opin. Biotechnol. 1997, 8: 701-707).

Collections of natural compounds in the form of bacterial, fungal, plant and animal extracts are available from, for example, Pan Laboratories (Bothell, Wash.) or MycoSearch (Durham, N.C.). Libraries of candidate compounds that can be screened using the methods of the present invention may be either prepared or purchased from a number of companies. Synthetic compound libraries are commercially available from, for example, Comgenex (Princeton, N.J.), Brandon Associates (Merrimack, N.H.), Microsource (New Milford, Conn.), and Aldrich (Milwaukee, Wis.). Libraries of candidate compounds have also been developed by and are commercially available from large chemical companies, including, for example, Merck, Glaxo Welcome, Bristol-Meyers-Squibb, Novartis, Monsanto/Searle, and Pharmacia UpJohn. Additionally, natural collections, synthetically produced libraries and compounds are readily modified through conventional chemical, physical, and biochemical means.

Useful regulators of iron metabolism and of hepcidin expression may be found within numerous classes of chemicals, including heterocycles, peptides, saccharides, steroids, and the like. In certain embodiments, the screening methods of the invention are used for identifying compounds or agents that are small molecules (i.e., compounds or agents with a molecular weight<600-700).

The screening of libraries according to the inventive methods will provide "hits" or "leads", i.e., compounds that possess a desired but not-optimized biological activity. The next step in the development of useful drug candidates is usually the analysis of the relationship between the chemical structure of a hit compound and its biological or pharmacological activity. Molecular structure and biological activity are correlated by observing the results of systemic structural modification on defined biological endpoints. Structure-activity relationship information available from the first round of screening can then be used to generate small secondary libraries which are subsequently screened for compounds with higher affinity. The process of performing synthetic modifications of a biologically active compound to fulfill stereoelectronic, physicochemical, pharmacokinetic, and toxicologic factors required for clinical usefulness is called lead optimization.

The candidate compounds identified by the screening methods of the invention can similarly be subjected to a structure-activity relationship analysis, and chemically modified to provide improved drug candidates. The present invention also encompasses these improved drug candidates.

C—Identification of Regulators of Iron Metabolism and Regulators of Hepcidin Expression According to the screening methods of the present invention, determination of the ability of a candidate compound to regulate iron metabolism or to regulate hepcidin expression includes comparison of at least one factor that is representative of the signaling activity of a TGF-β superfamily member measured in the test and control systems.

In the inventive screening methods, a candidate compound is identified as a regulator of hepcidin expression or activity and/or as a regulator of iron metabolism, if the factor measured in the test system is less or greater than the factor measured in the control system. More specifically, if a candidate compound is found to be an agonist of TGF-β or an antagonist of BMP, it is identified as an inhibitor of hepcidin expression or activity and/or as an enhancer of iron metabolism. Alternatively, if a candidate compound is found to be an antagonist of TGF-β or an agonist of BMP, it is identified as an enhancer of hepcidin expression or activity and/or as an inhibitor of iron metabolism.

Factors representative of the signaling activity of a TGF-β superfamily member include reporter assay signaling, and target gene expression (e.g., extracellular matrix protein genes). Other factors representative of the signaling activity of a TGF-β superfamily member include Smad phosphorylation, translocation of phosphorylated Smad proteins to the nucleus, and alterations in cell growth rates. In certain embodiments, the factor measured in the screening methods of the invention is the amount of iron present in the system. In other embodiments, the factor measured is the level of hepcidin mRNA expression in the system. In still other embodiments, the factor measured is the hepcidin/actin ratio in the system.

Reproducibility of the results obtained in the inventive screening methods may be tested by performing the analysis more than once with the same concentration of the same candidate compound (for example, by incubating cells in more than one well of an assay plate). Additionally, since candidate compounds may be effective at varying concentrations depending on the nature of the compound and the nature of its mechanism(s) of action, varying concentrations of the candidate compound may be tested (for example, different concentrations can be added to different wells containing cells). Generally, candidate compound concentrations from 1 fM to about 10 mM are used for screening. Preferred screening concentrations are generally between about 10 pM and about 100 µM.

In certain embodiments, the methods of the invention further involve the use of one or more negative and/or positive control compounds. A positive control compound may be any molecule or agent that is known to modulate the signaling activity of the TGF-β family member studied in the screening assay. A negative control compound may be any molecule or agent that is known to have no effect on the signaling activity of the TGF-β family member studied in the screening assay. In these embodiments, the inventive methods further comprise comparing the modulating effects of the candidate compound to the modulating effects (or absence thereof) of the positive or negative control compound. For example, Noggin and decorin may be used as positive controls for the inhibition of BMP signaling and TGF-β signaling, respectively.

D—Characterization of Candidate Compounds

As will be appreciated by those skilled in the art, it is generally desirable to further characterize regulators identified by the inventive screening methods.

For example, if a candidate compound has been identified as a modulator of the signaling activity in a given TGF-β superfamily member in a given cell culture system (e.g., an established cell line), it may be desirable to test this ability in a different cell culture system (e.g., primary or secondary cells). Alternatively or additionally, it may be desirable to directly evaluate the effects of the candidate compound on hepcidin expression, for example by quantitating hepcidin mRNA expression using real-time quantitative RT-PCR (as described in Example 1). It may also be desirable to evaluate the specificity of the candidate compound by testing its ability to modulate the signaling activity of other members of the TGF-β superfamily members. It may also be desirable to perform pharmacokinetics and toxicology studies.

Candidate compounds identified by screening methods of the invention may also be further tested in assays that allow for the determination of the compounds' properties in vivo. Suitable animal models include animal models that can exhibit iron deficient or iron overload or that have been determined to exhibit up-regulation of hepcidin expression or down-regulation of hepcidin expression.

Examples of animal models for iron overload include, but are not limited to, mice treated with carbonyl iron, β2-microglobulin knockout mice (C. Pigeon et al., J. Biol. Chem., 2001, 276: 7811-7819), USF2 (Upstream Stimulatory Factor 2) knockout mice (G. Nicolas et al., Proc. Natl. Acad. Sci. USA, 2001, 98: 8780-8785), and HFE knockout mice (K. A. Ahmad et al., Blood Cells Mol. Dis., 2002, 29: 361-366). Examples of animal models for iron deficiency include, but are not limited to, models of anemia in mice with acute hemolysis, provoked by phenylhydrazine, and mice with bleeding provoked by repeated phlebotomies (G. Nicolas et al., J. Clin. Invest., 2002, 110: 1037-1044). Examples of animal models exhibiting increased hepcidin mRNA expression include mice treated by partial hepatectomy (N. Kelley-Loughnane et al., Hepatology, 2002, 35: 525-534), by lipopolysaccharide (G. R. Lee, Semin. Hematol., 1983, 20: 61-80), and turpentine (G. Nicolas et al., J. Clin. Invest., 2002, 110: 1037-1044).

E—Pharmaceutical Compositions of Identified Regulators

The present invention also provides pharmaceutical compositions, which comprise, as active ingredient, an effective amount of at least one regulator of iron metabolism or at least one regulator of hepcidin expression or activity identified by an inventive screening assay. The pharmaceutical compositions of the invention may be formulated using conventional methods well known in the art. Such compositions include, in addition to the active ingredient(s), at least one pharmaceutically acceptable liquid, semiliquid or solid diluent acting as pharmaceutical vehicle, excipient or medium, and termed here "pharmaceutically acceptable carrier".

According to the present invention, pharmaceutical compositions may include one or more regulators of the invention as active ingredients. Alternatively, a pharmaceutical composition containing an effective amount of one inventive regulator may be administered to a patient in combination with or sequentially with a pharmaceutical composition containing a different inventive regulator. However, in both cases, the regulators preferably have the same regulatory effect on iron metabolism and/or hepcidin expression or activity. For example, an agonist of BMP and an antagonist of TGF-β, which both enhance hepcidin expression and inhibit iron metabolism, may be administered to a subject in a single pharmaceutical composition, or in two different pharmaceutical compositions.

As will be appreciated by one skilled in the art, a regulator of hepcidin expression or an iron metabolism regulator, or a pharmaceutical composition thereof, may be administered serially or in combination with conventional therapeutics used in the treatment of iron metabolism disorders. Such therapeutics include iron supplements (in the case of diseases associated with iron deficiency) and iron chelating agents (in the case of diseases associated with iron overload). Iron supplements include, but are not limited to, ferrous fumarate, ferrous gluconate, ferrous sulfate, iron dextran, iron polysaccharide, iron sorbitol, sodium ferric gluconate, and iron sucrose. Iron chelating agents include, for example, desferrioxamine, bathophenanthroline, and Clioquinol. Iron supplements or iron chelating agents may be included in pharmaceutical compositions of the present invention. Alternatively, they may be administered in separate pharmaceutical compositions.

Alternatively or additionally, a regulator of hepcidin expression or an iron metabolism regulator, or a pharmaceutical composition thereof, may be administered serially or in combination with conventional therapeutic regimens for the treatment of iron metabolism disorders. These include, for example, phlebotomy, in the case of conditions associated with iron overload.

III. Methods of Treatment

In another aspect, the present invention provides methods for the treatment and/or prevention of conditions associated with perturbations in iron metabolism, including conditions associated with iron overload and conditions associated with iron deficiency. These methods comprise administering to a subject having or at risk or having such a condition, an effective amount of a compound that modulates the signaling activity of at least one TGF-β superfamily member, wherein modulation of the signaling activity of the TGF-β superfamily member results in regulation of hepcidin expression or activity in the subject.

The compound may be a known agonist or antagonist of the TGF-β superfamily member. Alternatively, the compound may be a regulator of iron metabolism or a regulator of hepcidin expression identified, for example, by a screening method provided by the present invention.

A—Iron Metabolism Diseases

Conditions that may be treated and/or prevented using the methods of the present invention include any disease, disorder, or syndrome associated with perturbations in iron metabolism. Perturbations in iron metabolism may be associated with disturbances in one or more of iron uptake, iron absorption, iron transport, iron storage, iron processing, iron mobilization, and iron utilization. Generally, perturbations in iron metabolism result in iron overload or iron deficiency.

Conditions associated with iron overload include both primary and secondary iron overload diseases, syndromes or disorders, including, but not limited to, hereditary hemochromatosis, porphyria cutanea tarda, hereditary spherocytosis, hyprochromic anemia, hysererythropoietic anemia (CDAI), faciogenital dysplasia (FGDY), Aarskog syndrome, atransferrinemia, sideroblastic anemia (SA), pyridoxine-responsive sidero-blastic anemia, and hemoglobinopathies such as thalassemia and sickle cell. Some studies have suggested an association between iron metabolism disorders, such as thalassemia and hemochromatosis, and a number of disease states, such as type II (non-insulin dependent) diabetes mellitus and atherosclerosis (A. J. Matthews et al., J. Surg. Res., 1997, 73: 35-40; T. P. Tuomainen et al., Diabetes Care, 1997, 20: 426-428).

Diseases associated with iron deficiency include, but are not limited to, anemia of chronic disease, iron deficiency anemias, functional iron deficiency, and microcytic anemia. The term "anemia of chronic disease" refers to any anemia that develops as a result of, for example, extended infection, inflammation, neoplastic disorders, etc. The anemia which develops is often characterized by a shortened red blood cell life span and sequestration of iron in macrophages, which results in a decrease in the amount of iron available to make new red blood cells. Conditions associated with anemia of chronic disease include, but are not limited to, chronic bacterial endocarditis, osteomyelitis, rheumatic fever, ulcerative colitis, and neoplastic disorders. Further conditions include other diseases and disorders associated with infection, inflammation, and neoplasms, including, for example, inflammatory infections (e.g., pulmonary abscess, tuberculosis, etc), inflammatory noninfectious disorders (e.g., rheumatoid arthritis, systemic lupus erythrematosus, Crohn's disease, hepatitis, inflammatory bowel disease, etc.), and various cancers, tumors, and malignancies (e.g., carcinoma, sarcoma, lymphoma, etc.). Iron deficiency anemia may result from conditions such as pregnancy, menstruation, infancy and childhood, blood loss due to injury, etc.

It has also been suggested that iron metabolism plays a role in a number of other diseases states, including cardiovascular disease, Alzheimer's disease, Parkinson's disease, and certain types of colo-rectal cancers (see, for example, P. Tuomainen et al., Circulation, 1997, 97: 1461-1466; J. M. McCord, Circulation, 1991, 83: 1112-1114; J. L. Sullivan, J. Clin. Epidemiol., 1996, 49: 1345-1352; M. A. Smith et al., Proc. Nat. Acad. Sci., 1997, 94: 9866-9868; P. Riederer et al., J. Neurochem., 1989, 512: 515-520; P. Knekt et al., Int. J. Cancer, 1994, 56: 379-382).

B—Subject Selection

Subjects suitable to receive a treatment according to the inventive methods include individuals that have been diagnosed with a condition associated with perturbations in iron metabolism, including, but not limited to, the diseases and disorders listed above, and individuals that are susceptible to conditions associated with perturbations in iron metabolism. Suitable subjects may or may not have previously received traditional treatment for the condition.

Other suitable subjects are individuals that exhibit iron deficiency or iron overload. Iron overload and iron deficiency may be detected using a number of laboratory tests available in the art that allow for the determination of total iron-binding capacity (TIBC), levels of serum iron, ferritin, hemoglobin, hematocrit, and urinary creatinine.

C—Administration

A treatment according to methods of the present invention may consist of a single dose or a plurality of doses over a period of time. A regulator of hepcidin expression or modulator of iron metabolism, or a pharmaceutical composition thereof, may also be released from a depot form per treatment. The administration may be carried out in any convenient manner such as by injection (subcutaneous, intravenous, intramuscular, intraperitoneal, or the like), oral administration, or sublingual administration.

Effective dosages and administration regimens can be readily determined by good medical practice and the clinical condition of the individual patient. The frequency of administration will depend on the pharmacokinetic parameters of the compound and the route of administration. The optimal pharmaceutical formulation can be determined depending upon the route of administration and desired dosage. Such formulations may influence the physical state, stability, rate of in vivo release, and rate of in vivo clearance of the administered compounds.

Depending on the route of administration, a suitable dose may be calculated according to body weight, body surface area, or organ size. Optimization of the appropriate dosage can readily be made by those skilled in the art in light of pharmacokinetic data observed in human clinical trials. The final dosage regimen will be determined by the attending physician, considering various factors which modify the action of drugs, e.g., the drug's specific activity, the severity of the damage and the responsiveness of the patient, the age, condition, body weight, sex and diet of the patient, the severity of any present infection, time of administration and other clinical factors. As studies are conducted, further information will emerge regarding the appropriate dosage levels and duration of treatment for various conditions associated with iron overload and iron deficiency.

EXAMPLES

The following examples describe some of the preferred modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Some of the results presented in this section have been described by the Applicants in a recent scientific manuscript (J. L. Babitt et al., "Bone Morphogenetic Protein Signaling by Hemoguvelin Regulates Hepcidin Expression", submitted

Example 1

Effects of BMP and TGF-β on Hepcidin Transcription in Liver Cells

Study Protocol. The effects of BMP-2, Noggin (a well-known BMP inhibitor), and TGF-β1 on hepcidin mRNA expression in HepG2 liver hepatoma cells were studied and quantitated using real-time quantitative RT-PCR.

HepG2 cells (ATTC Number HB-8065) were grown in a-MEM (Minimal Essential Medium Alpha Medium with L-Glutamine supplemented with 10% fetal bovine serum, 100 U/mL penicillin and 100 µg/mL streptomycin) to 60% confluence on 6 cm tissue culture plates. Cells were then incubated in low-serum conditions (a-MEM with 1% FBS), with 1 µg/mL Noggin.Fc (R & D Systems, Minneapolis, Minn.) at 37° C. for 48 hours, or serum-starved for 6 hours followed by incubation with 50 ng/mL BMP-2 (R & D Systems) at 37° C. for 16 hours, or with 1 ng/mL TGF-β1 (R & D Systems) at 37° C. for 16 hours. Alternatively, cells were incubated at 37° C. for 72 hours with non-transferrin-bound iron (65 µM Fe-NTA). Fe-NTA was generated by combining 1:1 molar ratio of $FeCl_3$ hexahydrate (Sigma) in 0.1 molar HCl with nitrilotriacetic acid (NTA, Sigma) in a-MEM medium supplemented with 20 mM Hepes pH 7.5, as previously described (E. W. Randell et al., J. Biol. Chem., 1994, 269: 16046-16053; S. G. Gehrke et al., Blood, 2003, 102: 371-376).

Total RNA was isolated from HepG2 cells treated as described above using the RNAeasy Mini Kit (QIAGEN™, Valencia, Calif.) including DNAse digestion with the RNAse-free DNAse Set (QIAGEN™), according to the manufacturer's instructions. Real-time quantification of mRNA transcripts was performed using a 2-step reverse transcriptase polymerase chain reaction (RT-PCR) using the ABI PRISM® 7900HT Sequence Detection System and SDS software version 2.0. First strand cDNA synthesis was performed using ISCRIPT™ cDNA Synthesis Kit (BIORAD™ Laboratories, Hercules, Calif.) according to the manufacturer's instructions using 2 µg of total RNA template per sample. In a second step, transcripts of hepcidin were amplified with sense primer HepcF (5'-CTGCAACCCCAGGACAGAG-3' (SEQ ID NO: 1)) and antisense primer HepcR (5'-GGAATAAATAAG-GAAGGGAGGGG-3' (SEQ ID NO: 2)) and detected using ITAQ™ SYBR Green Supermix with ROX (BIORAD™). In parallel, transcripts of β-actin were amplified with sense primer BactF (5'-AGGATGCAGAAGGAGATCACTG-3' (SEQ ID NO: 3)) and antisense primer BactR (5'-GGGTG-TAACGCAACTAAGTCATAG-3' (SEQ ID NO: 4)) and detected in a similar mariner to serve as an internal control.

Standard curves for hepcidin and 13-actin were generated from accurately determined dilutions of cDNA clones of hepcidin (IMAGE clones 4715540) and β-actin (IMAGE clone 3451917) as templates (IMAGE clones were purchased from Open Biosystems, and DNA sequenced to verify their inserts). Samples were analyzed in triplicate, and results are reported as the ratio of mean values for hepcidin to β-actin:

Results. As shown in FIG. 1, incubation of HepG2 cells with Fe-NTA decreased the hepcidin/actin ratio expression approximately 6-fold (bar 4), a result which correlates well with a previously reported decrease in hepcidin expression caused by Fe-NTA in HepG2 cells (S. G. Gehrke et al., Blood, 2003, 102: 371-376). Significantly, incubation with 50 ng/mL BMP-2 increased the hepcidin/actin ratio expression by 10-fold (±8%) over baseline (compare bar 2 with bar 1). In contrast, incubation with 1 µg/mL Noggin.Fc (which inhibits endogenous BMP signaling) decreased hepcidin/actin ratio expression 50-fold (±19%) below baseline (compare bar 3 with bar 1).

Figure 2:
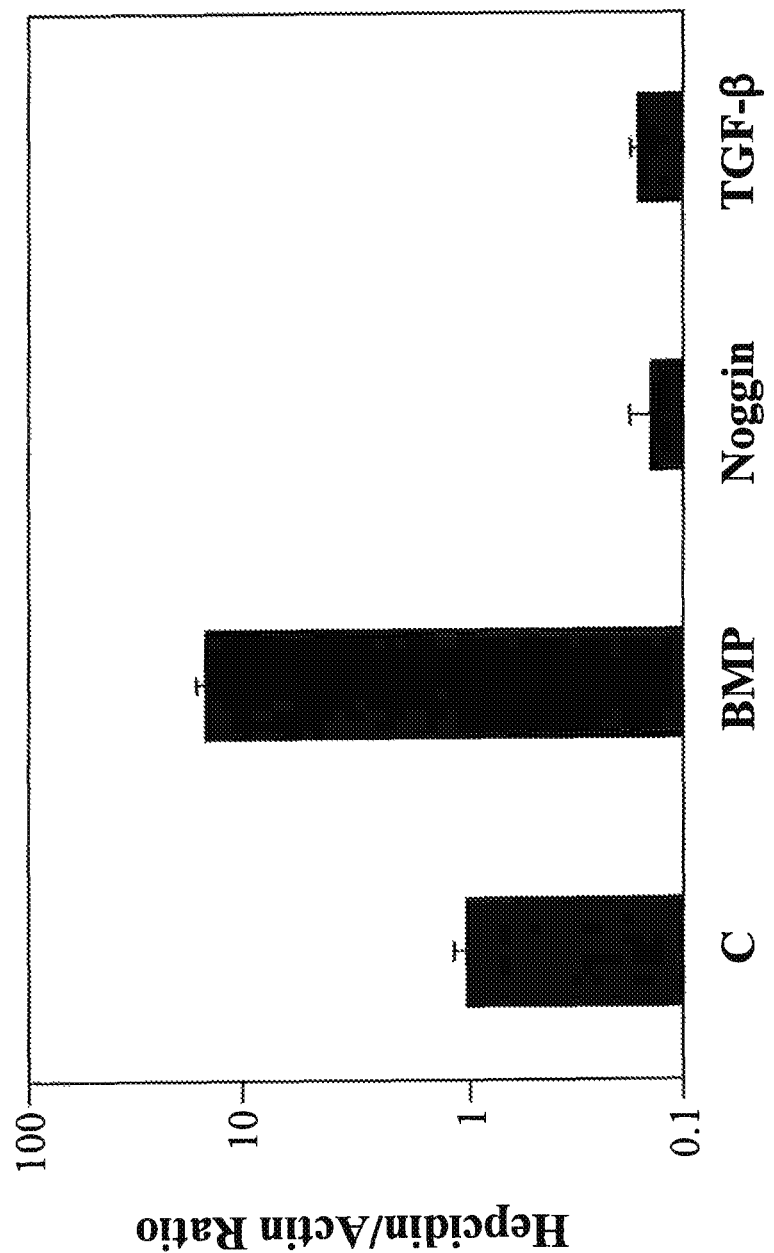
FIG. 2 is a graph showing the effects of BMP-2, Noggin.Fc, and TGF-β1 on the hepcidin/actin ratio in HepG2 cells compared to the hepcidin/actin ratio in control cells, C (i.e., HepG2 cells incubated in the absence of these agents).

As shown in FIG. 2, incubation of HepG2 cells with 50 ng/mL BMP-2 increased the hepcidin/actin ratio expression by 15-fold (±8%) over baseline (compare bar 2 with bar 1). In contrast, incubation with 1 µg/mL Noggin.Fc (which inhibits endogenous BMP signaling) decreased hepcidin/actin ratio expression 6-fold (±23%) below baseline (compare bar 3 with bar 1). In addition, incubation with 1 ng/ml TGF-β1 decreased hepcidin/actin ratio expression 6-fold (±6%) below baseline (compare bar 4 with bar 1).

Example 2

HJV.Fc Protein as Modulator of Hepcidin Expression

Juvenile hemochromatosis is a severe variant of hemochromatosis caused by mutations in two genes that give indistinguishable phenotypes. One gene encodes hepcidin (RAMP, 19q13.1). The second gene has recently been identified as hemojuvelin (HJV, 1q21). Although the function of HJV is unknown, hepcidin levels are depressed in persons with HJV mutations, indicating that HJV may be a modulator of hepcidin expression. As already mentioned herein, HJV is also a member of the repulsive guidance molecule (RGM) family of proteins, including RGMa and DRAGON, neuronal adhesion molecules which were recently shown by the present Applicants to function as a BMP co-receptor (J. L. Babitt et al., J. Biol. Chem., 2005, 280: 29820-29827; T. A. Samad et al., J. Biol, Chem., 2005, 280: 14122-14129, each of which is incorporated herein by reference in its entirety). The study presented below was undertaken to investigate whether HJV could similarly mediate BMP signaling.

Materials and Methods cDNA subcloning. cDNA encoding mutant murine HJV with a glycine to valine substitution at amino acid 313 (mHJVG313V) was generated by an overlapping PCR strategy. Two primers 5'-ACCGAATTCGGGGGACCTGGCTGGATAG-3' (SEQ ID NO: 5) and
5'-CGGAGGGCATACCCCAACACACAG-3' (SEQ ID NO: 6) were used to generate an N-terminal fragment of mHJV incorporating a substitution of valine for glycine at amino acid 313. Primers 5'-CTGTGTGTTGGGGtATGC-CCTCCG-3' (SEQ ID NO: 7) and
5'-CCCTCTAGATGGTGCCAGTCTCCAAAAGC-3' (SEQ ID NO: 8) were used to generate a C-terminal fragment of HJV with the identical substitution. A final round of PCR was performed using the outside primers to generate mutant mHJVG313V, which was then subcloned into the expression vector pCDNA 3.1 (INVITROGEN™, Carlsbad, Calif.).

cDNA encoding soluble mHJV.Fc fusion protein was generated by PCR of the extracellular domains of wild-type murine HJV using primers: 5'-GGAAGCTTATGGGC-CAGTCCCCTAGT-3' (SEQ ID NO: 9) and
5'-CCGGATCCGCTAAGTTCTCTAAATCCGTC-3' (SEQ ID NO: 10), followed by subcloning into the mammalian expression vector plgplus (R & D Systems, Minneapolis, Minn.) in-frame with the Fc portion of human IgG.

cDNA encoding flag-tagged human HJV (hHJV) was generated from human HJV transcript variant B (IMAGE clone 6198223), which does not contain exon 2, purchased form ATCC (#10642497). Exon 2 which codes for the signal peptide of the full length HJV isoform (variant A, ACCESSION #NM213653) was amplified by PCR from human genomic DNA using the forward primer: 5'-CGAGAATTCACTTA-CAGGGCTIVCGGTCA-3' (SEQ ID NO: 11) and the reverse primer: 5'-GCATTGAGAATGAGCATGTCCACAGAG-GAGCAGCAG-3' (SEQ ID NO: 12). A downstream cDNA fragment corresponding to the rest of the coding sequence (including the stop codon) was amplified by PCR from the IMAGE clone using the forward primer 5'-CCTCTGTGGA-CATGCTCATTCTCAATGCAAGATCCTCCGCTG-3' (SEQ ID NO: 13) and 5'-CGTCTCGAGTTACTGAATG-CAAAGCCACAGAACAAAGAGC-3' (SEQ ID NO: 14), as reverse primer. The two overlapping fragments were fused together by PCR and the full length cDNA product was then cut with EcoR I and Xho I and clone into pCDNA3.1 (INVITROGEN™), to generate pCDNA3.1-hHJV. To generate N-terminal Flag-tagged hHJV, an upstream fragment corresponding to the beginning of exon 3 was generated by PCR using forward primer:
5'-GACAGATCTGCGGCCGCTCATTCTCAAT-
GCAAGATCCTCCG-3' (SEQ ID NO: 15), and reverse primer: 5'-GAGCAGTTGTGCTGGATCATCAGG-3' (SEQ ID NO: 16). Following a Not I /Sac II digestion, the fragment was ligated together with a downstream Sac II/Xba I hHJV fragment, removed from pCDNA3.1-hHJV, into Not I/Xbal sites of p3XFLAGCMV9 (SIGMA-ALDRITCH®).

cDNA encoding mutant Flag-tagged hHJV G99V (hG99V), with a valine to glycine substitution at amino acid 99, was generated from hHJV by site directed mutagenesis using the QUIKCHANGE® kit (STRATAGENE™, La Jolla, Calif.). cDNA encoding the hepcidin promoter luciferase construct was generated by subcloning the −2649 to +45 region of the human hepcidin promoter 46 in the pGL2-Bsic vector (PROMEGA™, Madison, Wis.) upstream of the firefly luciferase reporter gene. All cDNA's were sequenced to verify the fidelity of the constructs (MGH, Molecular Biology DNA Sequencing Core Facility).

Cell culture and transfection. CHO cells (American Type Culture Collection ATCC #CCL-61) were cultured in F-12K Nutrient Mixture, Kaighn's Modification (INVITROGEN™) supplemented with 10% fetal bovine serum (FBS) (Atlanta Biologicals, Lawrenceville, Ga.). HepG2 cells and Hep3B cells (ATCC #HB-8065 and #HB-8064) were cultured in Minimal Essential Alpha Medium with L-glutamine (a-MEM, INVITROGEN™) containing 10% FBS. HEK 293 cells (ATCC #CRL-1573) were cultured in Dulbecco's modification of Eagle's medium (DMEM; CELLGRO® Mediatech, Herndon, Va.) supplemented with 10% FBS. All plasmid transfections were performed with Lipofectamine 2000 (INVITROGEN™) or Effectene transfection reagent (QIAGEN™ Inc, Valencia, Calif.) according to manufacturer instructions. Stably transfected cells were selected and cultured in 1 mg/ml Geneticin (CELLGRO® Mediatech, Herndon, Va.).

Luciferase assay. HepG2 or Hep3B cells were transiently transfected with 2.5 μg BMP responsive luciferase reporter (BRE-Luc), 2.5 μg TGF-β responsive luciferase reporter, $(CAGA)_{12}$MPL-Luc (CAGA-Luc) (both kindly provided by Peter ten Dijke, Leiden University Medical Center, The Netherlands), or 2.5 μg hepcidin promoter luciferase reporter construct, in combination with 0.25 μg pRL-TK Renilla luciferase vector (Promega) to control for transfection efficiency, with or without co-transfection with wild-type or mutant HJV cDNA. Forty-eight hours after transfection, cells were serum starved in a-MEM supplemented with 1% FBS for 6 hours and treated with varying amounts of TGF-β1 or BMP ligands (R & D Systems) for 16 hours, in the absence or presence of 1 μg/ml noggin (R & D Systems) or 20 μg/ml neutralizing anti-BMP-2/4 antibody (R & D Systems). Cells were lysed, and luciferase activity was determined with the Dual Reporter Assay according to the manufacturer's instructions (PROMEGA™). Experiments were performed in duplicate or triplicate wells. Relative luciferase activity was calculated as the ratio of firefly (reporter) and Renilla (transfection control) luciferase values, and is expressed as the fold increase over unstimulated cells transfected with reporter alone.

Purification of mHJV.Fc. CHO cells stably expressing mHJV.Fc were cultured in F-12K Nutrient Mixture, Kaighn's Modicfication, supplemented with 5% ultra-low IgG FBS (Invitrogen) using 175-cm² multifloor flasks (Denville Scientific, Southplainfield, N.J.). mHJV.Fc was purified from the media of stably transfected cells via one-step Protein A affinity chromatography using HiTrap rProtein A FF columns (Amersham Biosciences, Piscataway, N.J.) as previously described (E. del Re et al., J. Biol. Chem., 2004, 279: 22765-22772, which is incorporated herein by reference in its entirety). Purified protein was eluted with 100 mM glycine-HCI, pH 3.2 and neutralized with 0.3 M Tris-HCI pH 9 as previously described (E. del Re et al., J. Biol. Chem., 2004, 279: 22765-22772). mHJV.Fc was subjected to reducing sodium dodecylsulfate-polyacrylamide gel electrophoresis (SDS-PAGE) and gels were stained with Bio-safe Coomassie blue (Bio-Rad, Hercules, Calif.) to determine purity and quantify protein concentration.

Generation of HJV antibody and immunoblot analysis. An affinity purified rabbit polyclonal anti-murine HJV antibody (αHJV) was raised against the peptide RVAEDVARAF-SAEQDLQLC (SEQ ID NO: 17), amino acids 292-310 in the C-terminus of murine HJV upstream of its hybrophobic tail (G. Papamokolaou et al, Nat. Genet., 2004, 36: 77-82). Livers from 129S6/SvEvTac wild-type or Hjv−/− mice (F. W. Huang et al., J. Clin. Invest., 2005, 115: 2187-2191), or cells transfected with wild-type or mutant HJV, were homogenized/sonicated in lysis buffer (200 mM Tris-HCI, pH 8, 100 mM NaCl, 1 mM EDTA, 0.5% NP-40, and 10% glycerol) containing a mixture of protease inhibitors (Roche, Mannheim, Germany) as previously described (J. L. Babitt et al., J. Biol. Chem., 2005, 280: 29820-29827, which is incorporated herein by reference in its entirety). For assays examining phosphorylated Smad expression, 1 mM sodium orthovanadate (Sigma, St. Louis, Mo.) and 1 mM sodium fluoride (SIGMA-ALDRITCH®) were added to the lysis buffer as phosphatase inhibitors. Purified mHJV.Fc, transfected cell lysates, or liver lysates, were subjected to reducing sodium dodecylsulfate-polyacrylamide gel electrophoresis (SDS-PAGE) and Western blot as previously described (J. L. Babitt et al., J. Biol. Chem., 2005, 280: 29820-29827) using HJV antibody (1:1000, 4 mg/mL) at 4° C. overnight, goat anti-human Fc antibody (1:1000) (Jackson ImmunoResearch Laboratories, West Grove, Pa.) at room temperature for 1 hour, or rabbit polyclonal anti-phosphosmad1/5/8 antibody (1:1000) (Cell Signaling, Beverly, Mass.) at 4° C. overnight. Blots were stripped and re-probed with mouse monoclonal anti-β-actin antibody (1:5000) (clone AC 15, SIGMA-ALDRITCH®), rabbit polyclonal anti-Smad1 antibody (1:250) (Upstate Biotechnology, Lake Placid, N.Y.) at 4° C. overnight, or rabbit polyclonal anti-actin antibody (1:50) (Biomedical Technologies, Inc., Stoughton, Mass.) for room temperature at 1 hour as loading controls.

Figure 3:
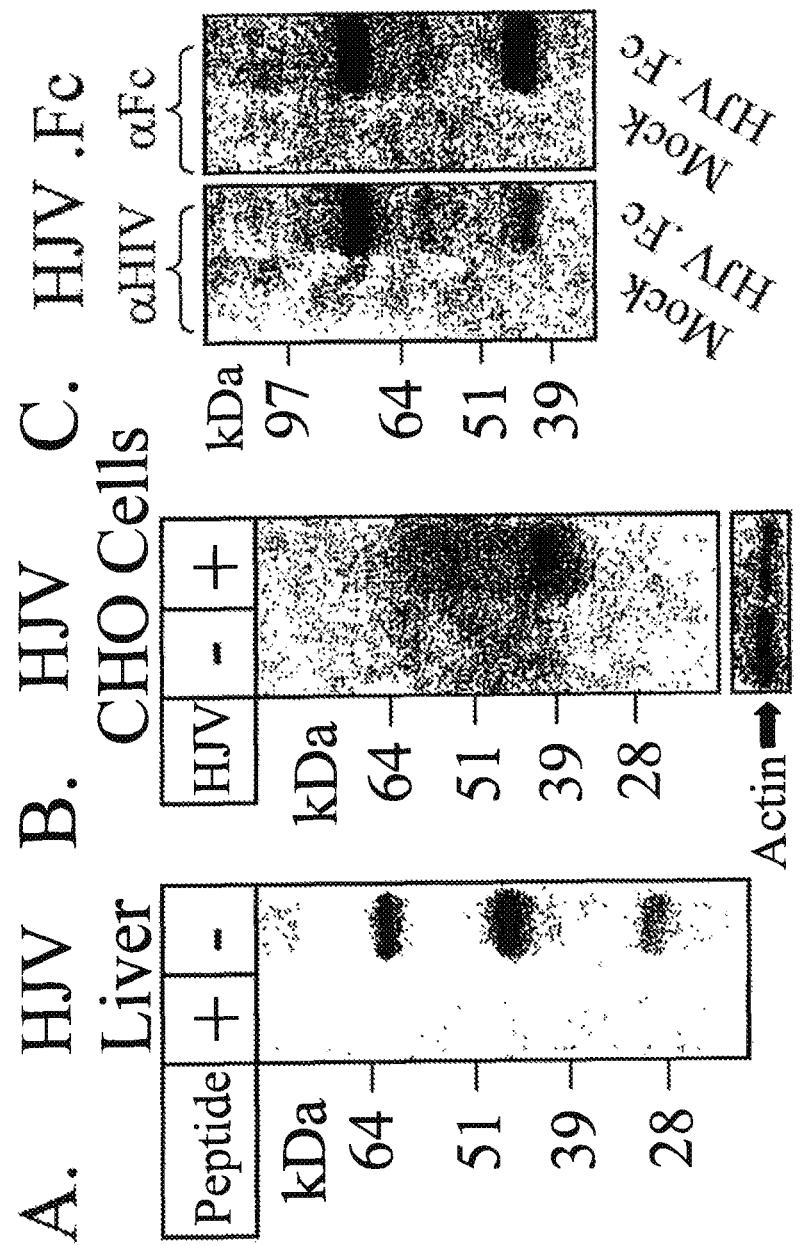
FIG. 3 shows a set of Western blot analyses of HJV protein in the liver (A) and transfected CHO cells (B), and of soluble HJV.Fc fusion protein (C).

HJV antibody recognizes major bands at ~49 kDa and ~30 kDA in the liver (lane 2, FIG. 3(A)), corresponding to the predicted size of full-length HJV and HJV which has been cleaved at a previously described proteolytic cleavage site. The ~62 kDa band likely represents a higher order form. No bands were seen after pre-incubation of antibody with competing peptide (lane 1). Similar results were seen in transfected CHO cells with the difference in size likely due to differential glycosylation or altered processing (FIG. 3(B)). HJV.Fc cDNA, generated by fusing the extracellular domain of HJV with human Fc, was stably transfected into CHO cells, and HJV.Fc protein was purified from the media by one-step protein A chromatography. Western Blot of purified protein with anti-HJV antibody (lanes 1-2) or anti-Fc antibody (lanes 34) confirmed the presence of both domains in the purified protein and provided further validation of the anti-HJV antibody. Both antibodies recognized ~70-75 kDa and ~60 kDa bands, corresponding to the predicted sizes of the full-length and proteolytically cleaved proteins. A lower band at ~40-45 kDa suggests another possible proteolytic cleavage site.

Ligand iodination and crosslinking. Two (2) µg of carrier-free human BMP-2 or BMP-4 ligand (R & D Systems) per reaction was iodinated with [$^{125}$I] by the modified chloramine-T method as previously described (C. A. Frolick et al., J. Biol. Chem., 1984, 259: 10995-11000, which is incorporated herein by reference in its entirety). $^{125}$I-BMP-2 was incubated with 60 ng mHJV.Fc or ALK5.Fc (R & D Systems) in 20 mM HEPES (pH 7.8) with 0.1% BSA and a mixture of protease inhibitors (Roche Diagnostics) or with buffer alone. This mixture was incubated in the absence or presence of 2.5 M disuccinimidyl suberate (DSS, Sigma, St. Louis, Mo.) followed by incubated with Protein A Sepharose beads (Amersham) as previously described (J. L. Babitt et al., J. Biol. Chem., 2005, 280: 29820-29827). Beads were washed with phosphate buffered saline (PBS) and protein eluted by non-reducing Laemmli sample buffer (Bio-Rad). Eluted protein was separated by SDS-PAGE and analyzed by autoradiography.

Quantitative reverse transcription polymerase chain reaction (RT-PCR). HepG2 or Hep3B cells were grown to 60% confluence on 6 cm tissue culture plates. Where indicated, cells were transfected with varying amounts of hHJV or hG99V cDNA. Twenty-four (24) hours after transfection, cells were serum-starved in a-MEM with 1% FBS followed by incubation with 50 ng/mL BMP-2 at 37° C. for various times or with 1 µg/mL noggin at 37° C. for 48 hours. For cycloheximide experiments, 10 µg/ml cycloheximide was added for 30 minutes prior to addition of BMP-2. Total RNA was isolated using the RNeasy Mini Kit (QIAGEN™ Inc., Valencia Calif.), including DNAse digestion with the RNase-Free DNase Set (QIAGEN)™ according to the manufacturer's instructions. Real time quantification of mRNA transcripts was performed using a 2-step reverse transcriptase polymerase chain reaction (RT-PCR) using the ABI PRISM® 7900HT Sequence Detection System and SDS software version 2.0. First strand cDNA synthesis was performed using ISCREPT™ cDNA Synthesis Kit (BIORAD™) according to the manufacturer's instructions using 2 µg total RNA template per sample.

In a second step, transcripts of hepcidin were amplified with sense primer HepcF 5'-CTGCAACCCCAGGACA-GAG-3' (SEQ ID NO: 1) and antisense primer HepcR 5'-GGAATAAATAAGGAAGGGAGGGG-3' (SEQ ID NO: 2) and detected using ITAQ™ SYBR Green Supermix with ROX (BIORAD™) according to the manufacturer's instructions. In parallel, transcripts of β-actin were amplified with sense primer BactF 5'-AGGATGCAGAAGGAGATCACTG-3' (SEQ ID NO: 3) and antisense primer 5'-GGGTGTAACG-CAACTAAGTCATAG-3' (SEQ ID NO: 4) and detected in a similar manner to serve as an internal control. Standard curves for hepcidin and β-actin were generated from accurately determined dilutions of plasmids containing cDNA sequences of hepcidin and β-actin as templates (IMAGE clones 4715540 and 3451917 from Open Biosystems followed by sequence analyses to verify the proposed insert). Samples were analyzed in triplicate, and results are reported as the ratio of mean values for hepcidin to β-actin. Transcripts for BMP-2 and BMP-4 were amplified from HepG2 cDNA generated above using the forward primer 5'-CGTGACCA-GACITTTGGACAC-3' (SEQ ID NO: 18) and reverse primer 5'-GGCATGATTAGTGGAGTIVAG-3' (SEQ ID NO: 19) (for BMP-2) and the forward primer: 5'-AGCAGCCAAAC-TATGGGCTA-3' (SEQ ID NO: 20) and reverse primer 5'-TG-GTTGAGTTGAGGTGGICA-3' (SEQ ID NO: 21) (for BMP-4).

Primary Hepatocyte Isolation and Culture. Primary hepatocytes were isolated by collagenase digestion of livers from 8 to 10 week old 129S6/SvEvTac wild-type or Hjv−/− mice (F. W. Huang et al., J. Clin. Invest., 2005, 115: 2187-2191) using previously described methods (J. Lin et al., Cell, 2004, 119: 121-135, which is incorporated herein by reference in its entirety). Briefly, mice were perfused through the inferior vena cava with calcium-free Hank's Balanced Salt Solution (HBSS) (Mediatech Inc.) supplemented with 0.5 mM EDTA and 16.7 mM sodium bicarbonate for 4 minutes at a rate of ~1.5 mL/min. Mice were subsequently perfused with calcium-containing HBSS containing 0.05% collagenase (SIGMA-ALDRITCH®), 1% bovine serum albumin and 16.7 mM sodium bicarbonate for 8 min. After enzymatic digestion, hepatocytes were liberated into culture medium [1:1 Dulbecco's modified Eagle's/Ham's F12 medium (GIBCO™, Grand Island, N.Y.) supplemented with 100 IU/ml penicillin, 100 µg/ml streptomycin, 18 mM HEPES, 1 mM sodium pyruvate, 10 µg/ml insulin, 5.5 µg/ml transferrin, and 5 ng/ml selenium (ITS; SIGMA-ALDRITCH®), 2 mM L-glutamine, 0.1 mM non-essential amino acids (Gibco™), 10% FBS (HYCLONE™, Logan Utah)], passed through a 100 µm BD FALCON™ mesh cell strainer (BD Biosciences, San Jose Calif.), centrifuged, gently washed with culture medium, and counted.

Cells (>90% hepatocytes by microscopy) were seeded on collagen-coated plates (SIGMA-ALDRITCH®) at $5 \times 10^5$ cells/60 mm dish. After 2 to 3 hours, cells were washed with PBS, serum starved with culture medium containing 1% FBS for 6 hours, and stimulated with recombinant human BMP-2 at varying concentrations for 12 hours. RNA was isolated using the RNeasy kit according to manufacturer's directions (QIAGEN™).

Northern Blot Analysis. Total RNA (2.5 µg) from primary hepatocytes was separated on a 1% formaldehyde agarose gel and transferred onto Hybond N+ membranes (Amersham Pharmacia Biotech). Membranes were baked for two hours at 80° C. under vacuum and hybridized with radioactively labeled probes specific for mouse hepcidin 1 amplified from Soares mouse p3NMF19.5 Mus musculus cDNA IMAGE clone: 317863 with primers 5'-TCCTTAGACTGCACAG-CAGAA-3' (SEQ ID NO: 22) and 5'-ATAAATAAGGACGG-GAGGGG-3' (SEQ ID NO: 23) and β-actin (S. Alonso et al., I. MoI. Evol., 1986, 23: 11-22). Expression was quantified using a phosphorimager (Molecular Dynamics, now Amersham Biosciences) and normalized to β-actin or 28S RNA as loading controls.

Figure 4:
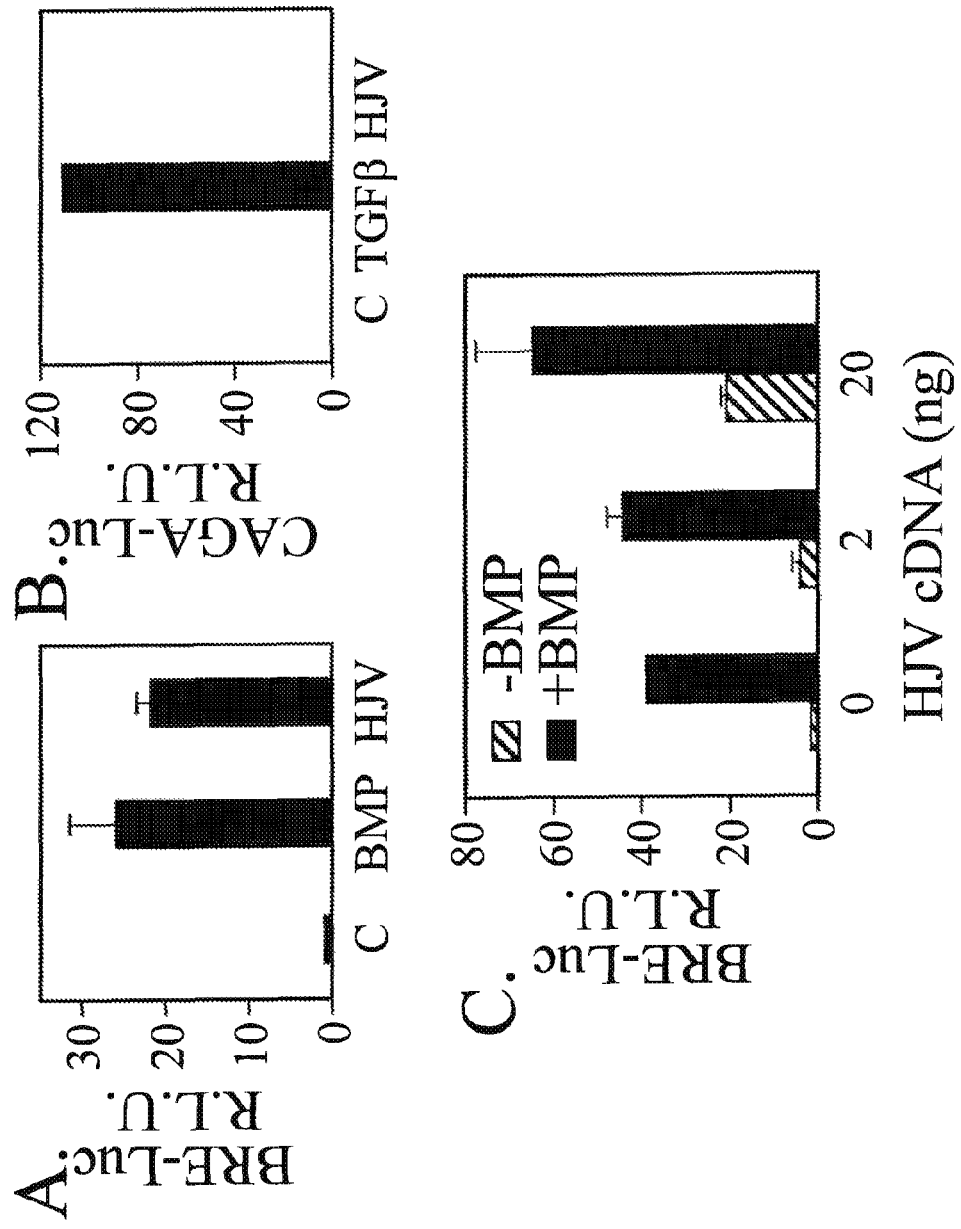
FIG. 4 is a set of three graphs showing measurements of luciferase activity in HepG2 cells transfected with a BMP-responsive luciferase reporter (A, C) or a TGF-β responsive luciferase reporter (B) incubated with or without BMP-2, BMP-4 or TGF-β1.

Statistical Analysis. A two-tailed Student's t-test was used with a P value of <0.05 to determine statistical significance.
Result 1: HJY Induces BMP but not TGF-β Signals HepG2 cells were transfected with a BMP-responsive luciferase reporter (BRE-Luc, FIG. 4, panels A and C) or TGF-β responsive luciferase reporter (CAGA-Luc, FIG. 4, panel B) either alone or in combination with cDNA encoding HJV. Transfected cells were then incubated with or without 0.5 nM BMP-2, BMP-4, or 40 pM TGF-β1 for 16 hours followed by measurement of luciferase activity. Stimulation with BMP or TGF-β3 increased the relative luciferase activity for their respective reporters compared with unstimulated cells (A and B, compare bars 2 to 1). Co-transfection with HJV similarly increased BRE luciferase activity even in the absence of exogenous BMP stimulation (A, bar 3). HJV-mediated BMP signaling was dose dependent (C, grey bars), and the presence of HJV augmented signaling produced by exogenous BMP (C, black bars). In contrast, co-transfection with HJV (up to 1 μg) did not increase CAGA-luciferase activity above baseline (B, bar 3). Taken together, these results demonstrate that HJV can mediate BMP signaling but not TGF-β signaling, and that HJV behaves in a manner consistent with a possible accessory receptor for BMP-2.

Result 2: HJV Mediated BMP Signaling is Inhibited by Noggin

The ability of HJV to mediate BMP signaling even in the absence of exogenous BMP ligand raises the question of whether HJV is acting in a ligand-independent manner, or whether it is augmenting signaling by endogenous BMP ligands. Studies were therefore undertaken to determine whether HJV-mediated signaling could be inhibited by Noggin, a soluble inhibitor of BMP signaling that functions by binding to BMP ligands and blocking the binding epitopes for BMP receptors.

Figure 5:
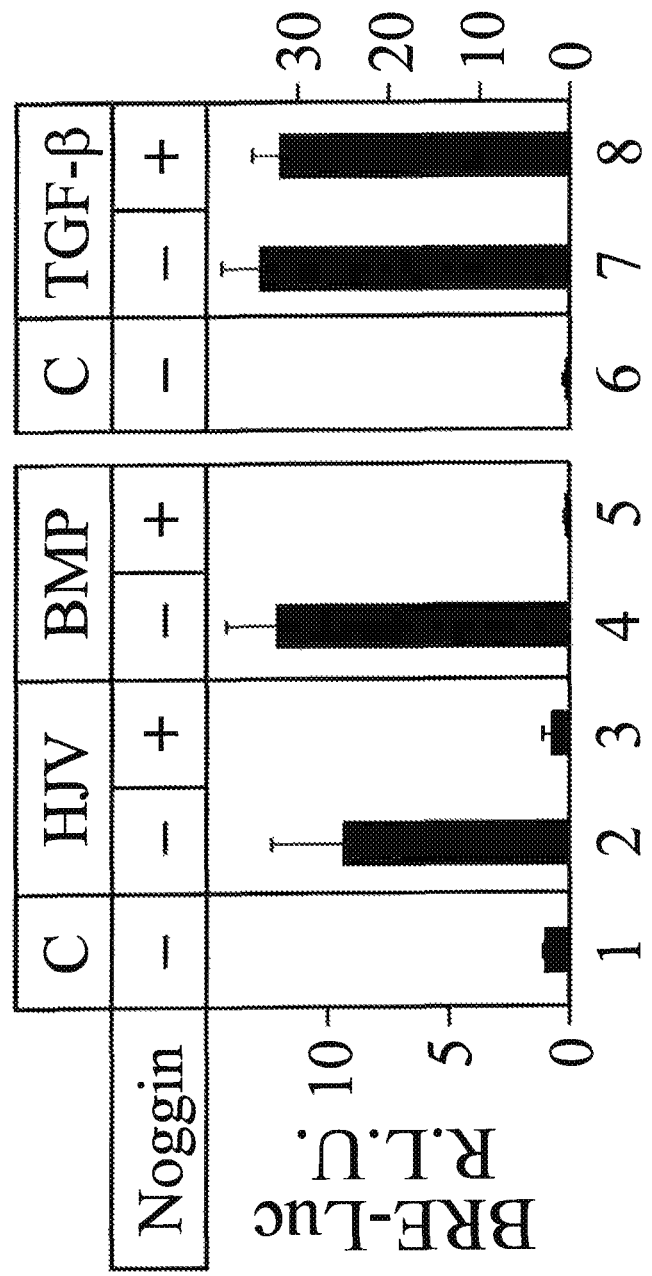
FIG. 5 is a graph showing measurements of luciferase activity in HepG2 cells transfected with BMP-responsive luciferase reporter and HJV cDNA or empty vector, and incubated with or without exogenous BMP-2 in the presence or absence of Noggin.

HepG2 cells were co-transfected with BRE-Luc and HJV cDNA or empty vector. Transfected cells were incubated with or without 0.5 nM exogenous BMP-2 in the presence or absence of 1 μg Noggin protein for 16 hours followed by measurement of luciferase activity. The results obtained are reported in FIG. 5.

In the absence of Noggin, co-transfection with HJV cDNA increased BRE luciferase activity 10 fold above baseline (compare bar 2 to bar 1). Similarly, incubation with exogenous BMP-2 increased BRE luciferase activity 12 fold over baseline (compare bar 4 to bar 1). This stimulation by either HJV or exogenous BMP could be blocked by the presence of Noggin protein (bars 3, 5). In contrast, Noggin did not affect TGF-β1 induced CAGA luciferase activity (bars 6-8). This data suggests that HJV generates BMP signals in a ligand-dependent manner, presumably via endogenously expressed BMP ligands.

Result 3: HJV.Fc Binds BMP-2 Selectively

Figure 6:
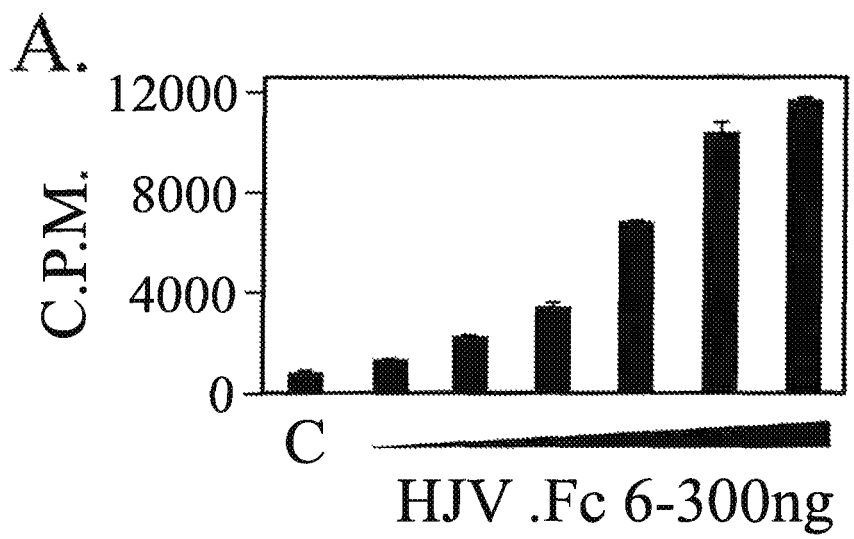
FIG. 6(A) is a graph showing results of radioactivity measurements from HJV.Fc incubated with $^{125}$I-labeled BMP-2.
FIG. 6(B) is a gel showing that $^{125}$I-BMP-2 can be chemically crosslinked with HJV.Fc in the presence of DSS (bar 4) and that this crosslinking can be inhibited by excess cold BMP-2 (bar 5).
Figure 6:
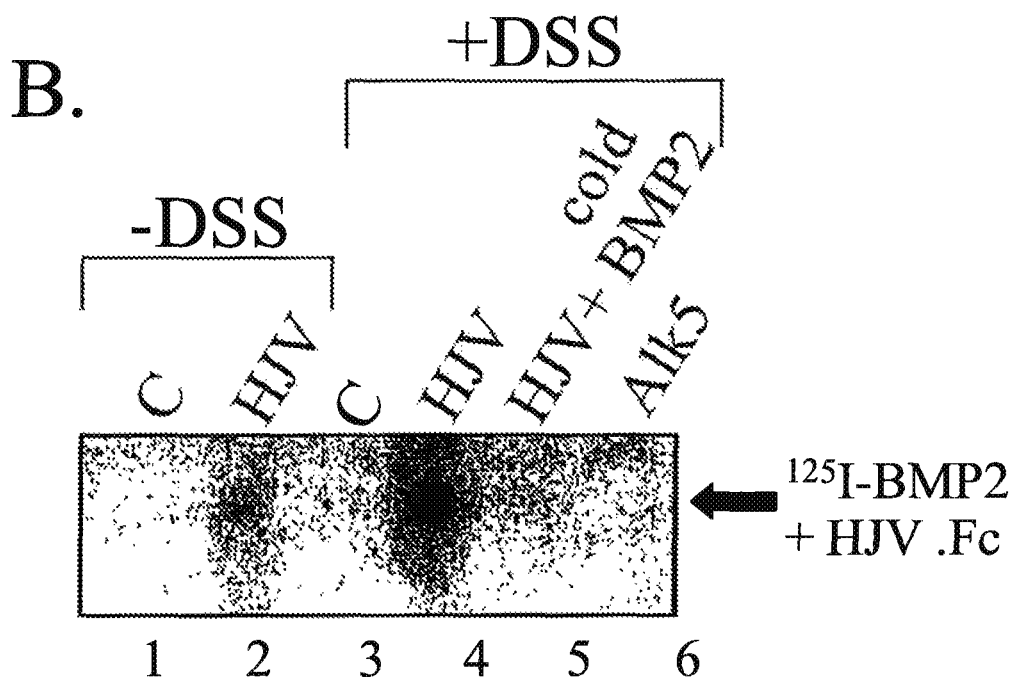
Figure 7:
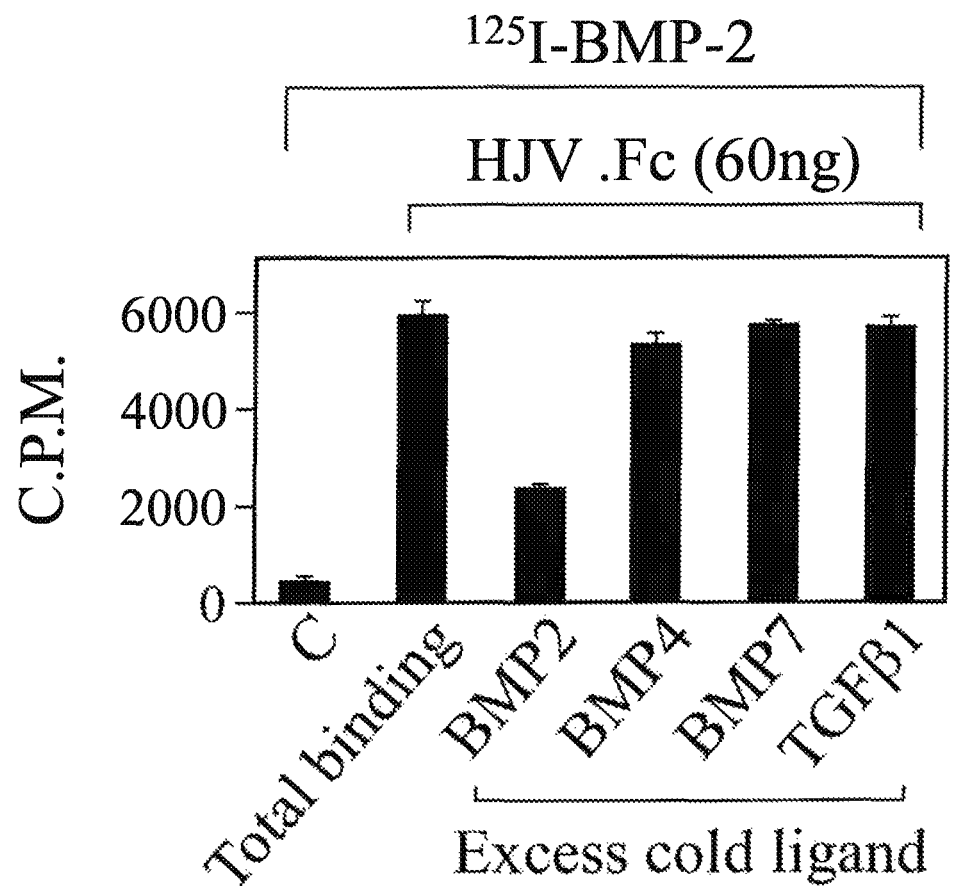
FIG. 7 is a graph reporting radioactivity measurements from HJV.Fc incubated with $^{125}$I-labeled BMP-2 with or without excess cold BMP-2, -4, -7, or TGF-β1.

HJV.Fc was incubated overnight with $^{125}$I-labeled BMP-2 with or without excess cold BMP-2, -4, -7 or TGF-β1, followed by incubation on protein A coated plates and determination of radioactivity (FIG. 6(A) and FIG. 7). Alternatively, chemical crosslinking of HJV.Fc with $^{125}$I-labeled BMP-2 was performed using DSS in a cell free system (FIG. 6(B)).

As shown in FIG. 6(A) HJV.Fc was able to bind to $^{125}$I-BMP-2 in a dose dependent fashion. Binding of HJV.Fc to $^{125}$I-BMP-2 was competitively inhibited by excess cold BMP-2 but not by BMP-4, BMP-7 or TGF-β1 (see FIG. 7). $^{125}$I-BMP-2 can be chemically crosslinked with HJV.Fc in the presence of DSS (FIG. 6(B), lane 4) and this can be inhibited by excess cold BMP-2 (lane 5). As negative controls, no band was seen in the absence of DSS (lanes 1 and 2) or when buffer alone (lane 3) or ALK5.Fc (a TGF-β type I receptor, lane 6) was used in place of HJV.Fc.

Result 4: HJV-Mediated BMP Signaling is Inhibited by Dominant Negative Type I Receptors ALK3 and ALK6 and by Dominant Negative Smad1

Figure 8A:
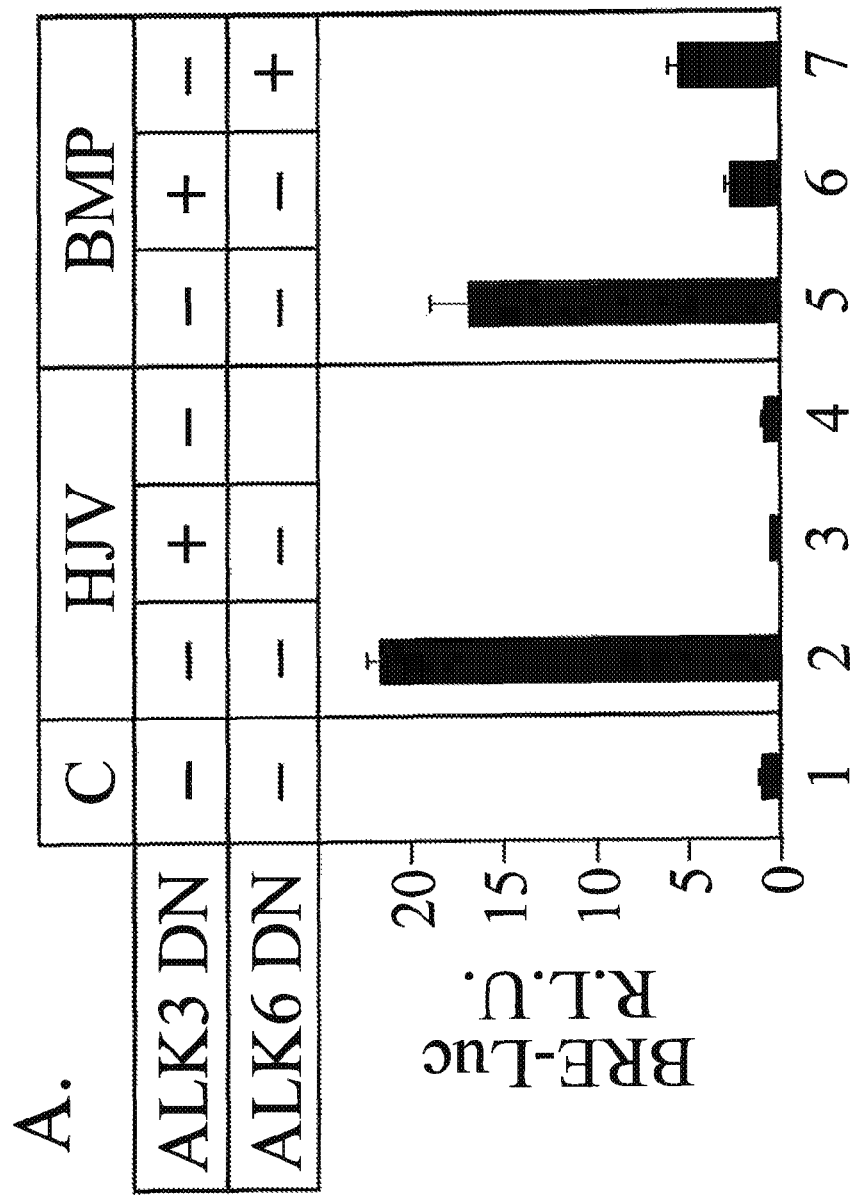
FIG. 8 is a set of two graphs showing measurements of luciferase activity in HepG2 cells co-transfected with BMP-responsive luciferase reporter and HJV either alone or in combination with dominant negative BMP type I receptor ALK3 (ALK3 DN) or ALK6 (ALK6 DN) (FIG. 8(A)), or with wild-type (WT) versus dominant negative (DN) R-Smad 1 (FIG. 8(B)).
Figure 8B:
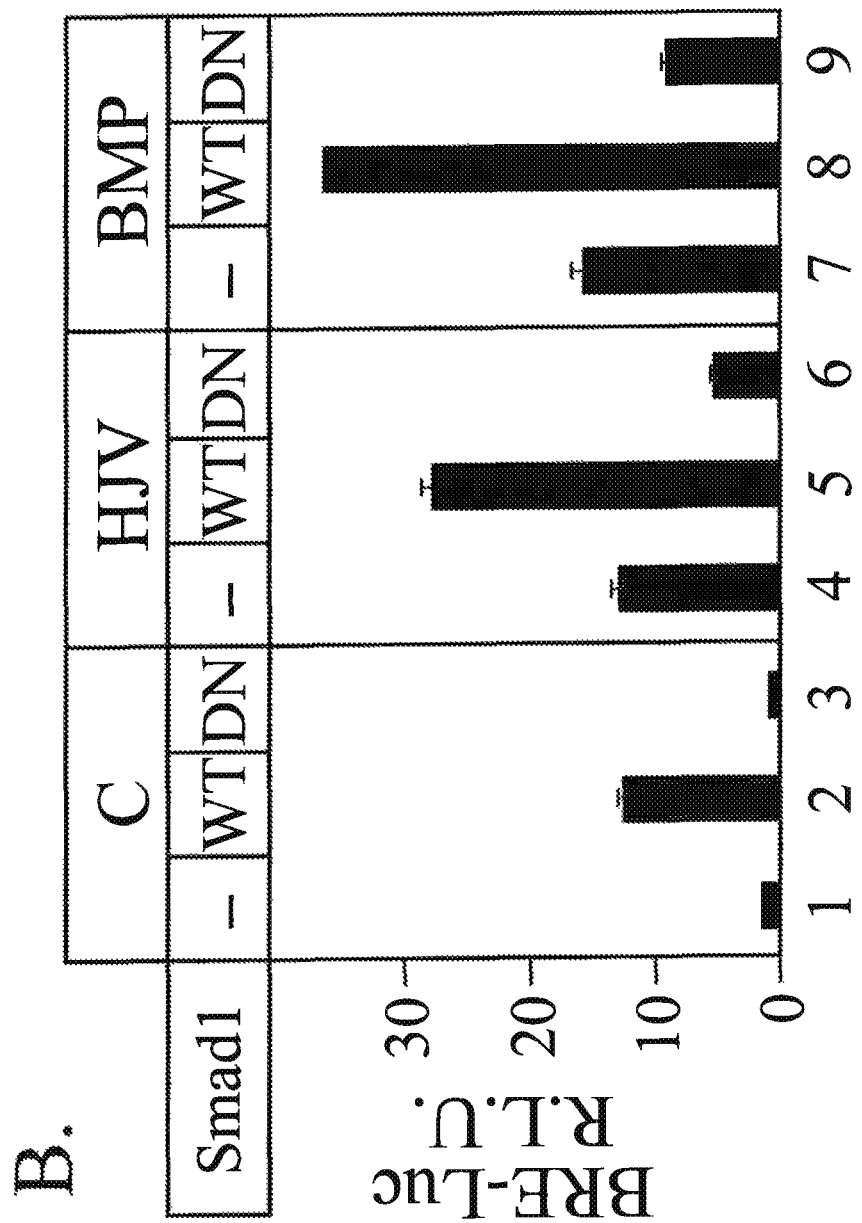

HepG2 cells were co-transfected with BRE-Luc and HJV either alone or in combination with dominant negative BMP type I receptor ALK3 (ALK3 DN) or ALK6 (ALK6 DN) (FIG. 8(A)), or with wildtype (WT) versus dominant negative (DN) R-Smad 1 (FIG. 8(B)). Transfected cells were then incubated in the presence or absence of 0.5 nM BMP-2 for 16 hours followed by measurement of luciferase activity.

As shown in FIG. 8(A), transfection with HJV or incubation of cells with exogenous BMP-2 increased BRE luciferase activity above baseline ~15-20 fold (compare bars 2 and 5 to bar 1). This stimulation by either HJV or exogenous BMP-2 could be blocked by co-transfection with dominant negative ALK3 (bars 3, 6) or dominant negative ALK6 (bars 4, 7).

As shown in FIG. 8(B), transfection with WT Smad 1 alone increased BRE luciferase activity ~12 fold above baseline (compare bars 2 to 1). In contrast, transfection with DN Smad 1 alone decreased BRE luciferase activity below baseline (compare bar 3 to bar 1). This provides further support that there is basal signal transduction via the BMP pathway in these cells in the absence of exogenously added ligand, and this signaling can be augmented by the presence of additional WT Smad 1 and inhibited by DN Smad 1. Transfection with HJV increased BRE luciferase activity ~12 fold above baseline (bar 4). Co-transfection of WT Smad 1 with HJV further augmented the signaling induced by either WT Smad 1 or HN alone (compare bar 5 to 2, 4). Co-transfection of DN Smad 1 with HN blocked the increase in signal seen with HJV alone (compare bar 6 to bar 4). Similar results were seen for the effect of WT Smad 1 and DN Smad 1 on exogenous BMP-2 stimulation (bars 7-9). Thus, HJV-mediated BMP signaling occurs via the classical BMP signaling pathway through BMP type I receptors ALK3 and ALK6 as well as R-Smad1.

Result 5: Production and Characterization of Mutant HJVG313V and HJVG3I3V.Fc Fusion Protein The most common mutation in HJV resulting in juvenile hemochromatosis is a point mutation substituting valine for glycine at amino acid 320 (corresponding to amino acid 313 in murine HJV). Mutant HJVG313V and soluble HJVG313V.Fc cDNA were made using PCR and subcloning techniques as described above, transfected into CHO cells, and analyzed by reducing SDS PAGE followed by Western blot with anti-HJV antibody (FIGS. 9(A) and (B) left panel) or anti-Fc antibody (FIG. 9(B), right panel). Alternatively, unpermeabilized transfected cells were analyzed by immunofluorescence microscopy using anti-HJV antibody (FIG. 10).

Figure 9:
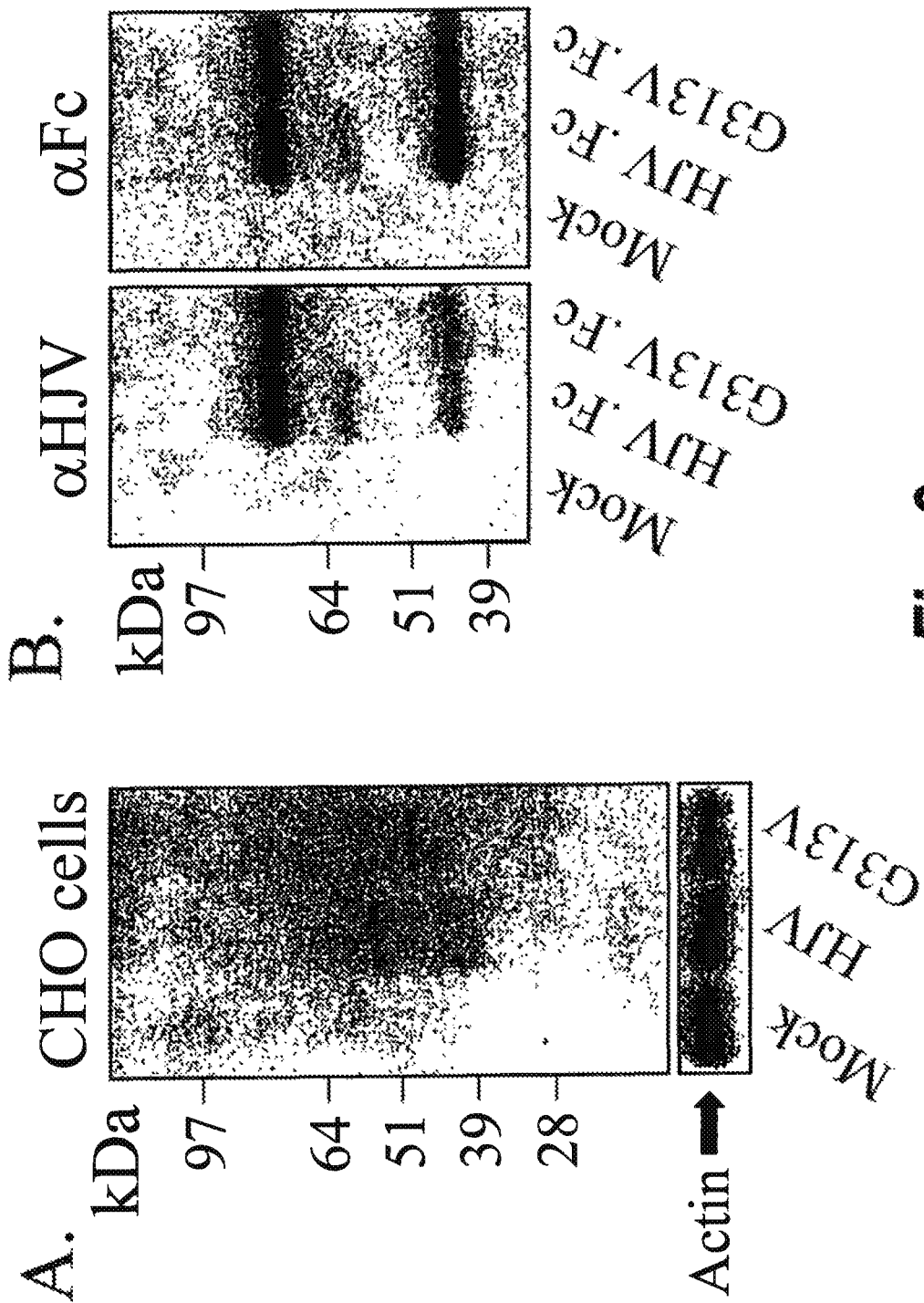
FIG. 9 shows two Western blot analyses of mutant HJVG313V (FIG. 9(A)) and soluble HJVG313V.Fc cDNA (FIG. 9(B)) made using PCR and subcloning techniques, and transfected into CHO cells

As shown in FIG. 9(A), mutant HJVG313V is expressed in CHO cells, but migrates with a different pattern than wild-type HJV suggesting it is processed differently, at least in this cell type. Mutant HJVG313V.Fc also appears to be processed differently from wild-type HN.Fc with a loss of the ~60kDa band (see FIG. 9(B)).

Figure 10:
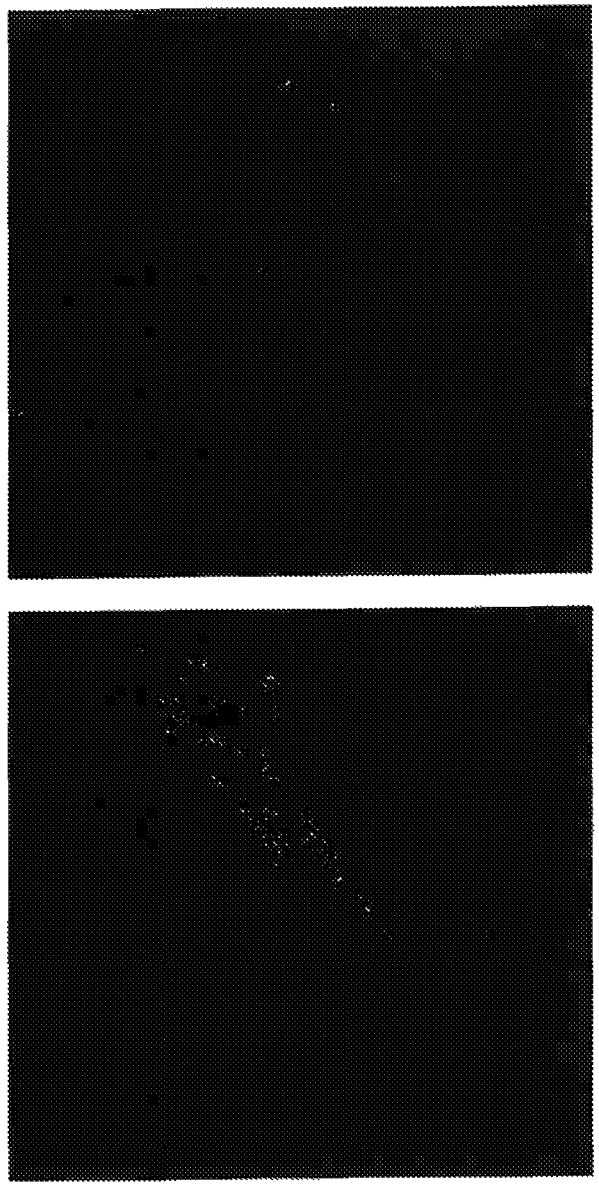
FIG. 10 shows immunofluorescence microscopy images of unpermeabilized cells transfected with wild-type HJV and mutant HJVG313V.

As shown in FIG. 10, both wildtype HJV and mutant HJVG313V are expressed on the cell surface in a punctate distribution.

Figure 11:
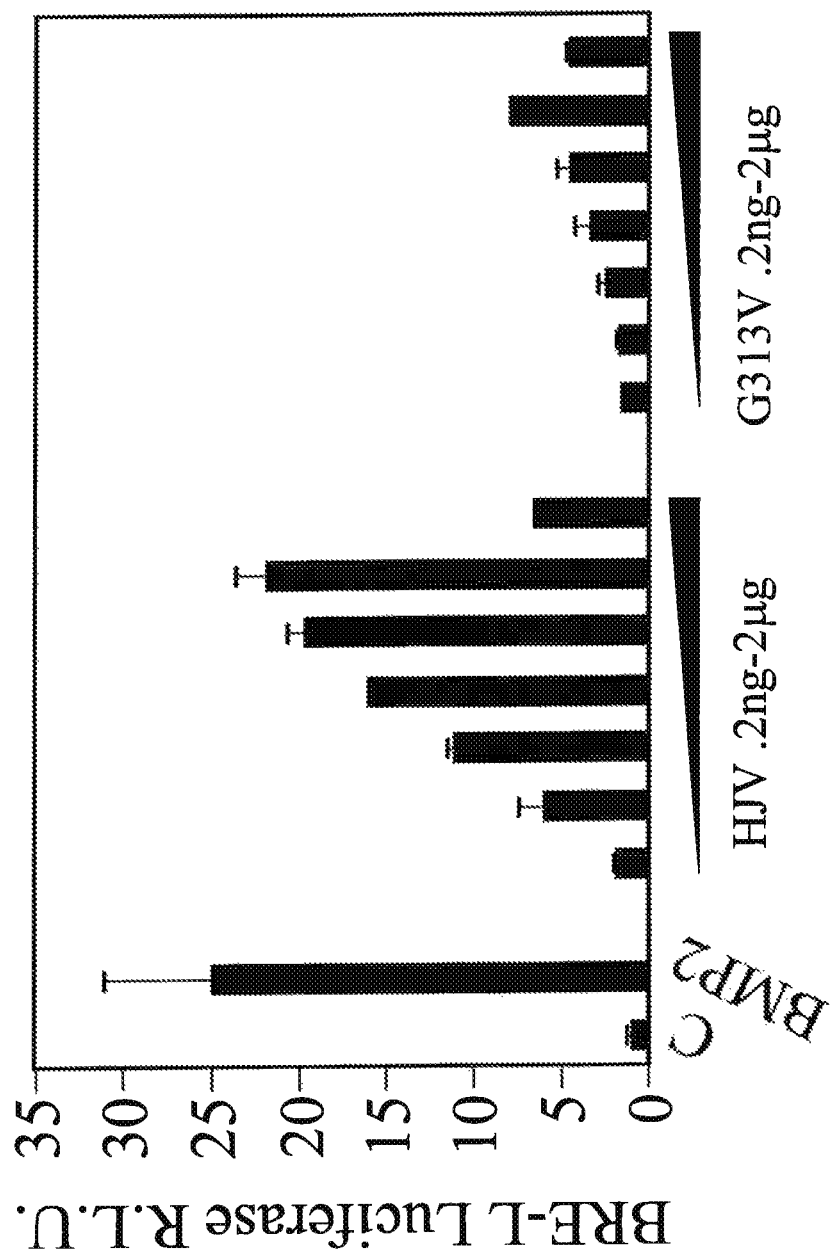
FIG. 11 is a graph reporting measurements of luciferase activity in HepG2 cells transfected with BMP-responsive luciferase reporter alone or in combination with increasing concentrations of wild-type HJV or mutant HJVG13V cDNA.

Result 6: Mutant HJVG3I3V Decreases BMP Signaling Ability Compared to Wild-Type HJV HepG2 cells were transfected with BRE-Luc alone or in combination with increasing concentrations of wildtype HJV or mutant HJVG13V cDNA. Transfected cells were incubated in the presence or absence of 0.5 nM BMP-2 for 16 hours followed by measurement of luciferase activity. As shown in FIG. 11, in the absence of exogenous ligand, wildtype HJV increased BRE luciferase activity up to 23 fold over baseline. This stimulation was on the order of that seen with 0.5 nM exogenous BMP-2. In contrast, mutant HJVG313V increased BRE luciferase activity only to a maximum of 9 fold. This suggests that mutant HJVG313V, which in humans can result in juvenile hemochromatosis, has decreased BMP signaling ability in liver cells, raising the question of whether BMP signaling might play a role in iron metabolism.

Conclusions

As reported above, the Applicants have shown that (1) HJV induces BMP but not TGF-β signaling; (2) HJV signaling is blocked by Noggin, a well-known BMP inhibitor; (3) HJV binds directly to radiolabeled BMP-2 ligand; (4) HJV signals via the BMP type I receptors, ALK-3 and ALK-6; (5) HJV signals via the BMP R-Smad, Smad1; (6) an HJV mutant known to cause juvenile hemochromatosis decreases BMP signaling ability; and (7) BMP increases, while Noggin decreases, hepcidin expression in liver cells.

These results suggest that HJV is a novel BMP co-receptor whose BMP signaling ability is important in regulating iron metabolism. Mutations in HJV could lead to decreased BMP signaling in liver cells, which could then decrease hepcidin expression, thereby explaining why persons with HJV mutations have depressed hepcidin levels and thus iron overload. The present findings regarding the novel mechanism of action of HJV reveal a heretofore undiscovered link between BMP signaling and iron metabolism, and could lead to novel treatment strategies of disorders of iron metabolism such as hemochromatosis and anemia of chronic disease.

Example 3

Effects of BMP-2 on Iron Binding Capacity in Vivo

Study Protocol: Normal mice were injected intraorbitally with 18 μg of BMP-2 (equivalent to 1 mg per kg body weight), or with carrier solution as a control. After 4 hours, blood was harvested and serum iron levels and total iron binding capacity was measured using colorimetric assays.

As shown on FIG. 12, the injection of BMP-2 led to significant decreases in both the serum iron and the total iron binding capacity. This result indicates that BMP ligands and BMP inhibitors will be useful as therapeutic agents to regulate iron levels in whole animals including humans.

Example 4

Proteolytically Stable HJV, RGMa, and Dragon Mutants

Experiments were undertaken to demonstrate the feasibility of producing mutant HJV, RGMa and Dragon proteins that, in contrast to their corresponding wild-type proteins, do not undergo proteolytic cleavage.

Figure 13:
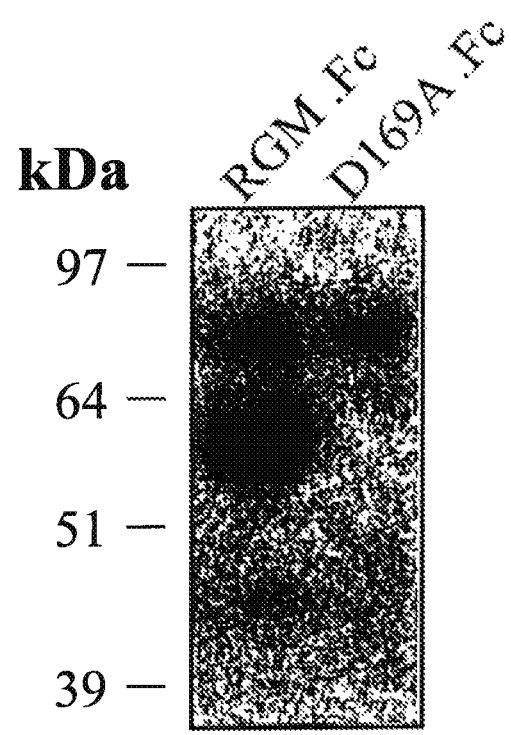
FIG. 13 is a gel showing that mouse RMGa-D169A.Fc fusion protein is not proteolytically cleaved compared to mouse RMGa.Fc fusion protein.

Mouse RGMa-D169A.Fc mutant cDNA was generated and expressed in HEK cell supernatants. FIG. 13 shows that the purified protein obtained is not proteolytically cleaved compared to wild-type mouse RMGa.Fc protein.

Figure 14:
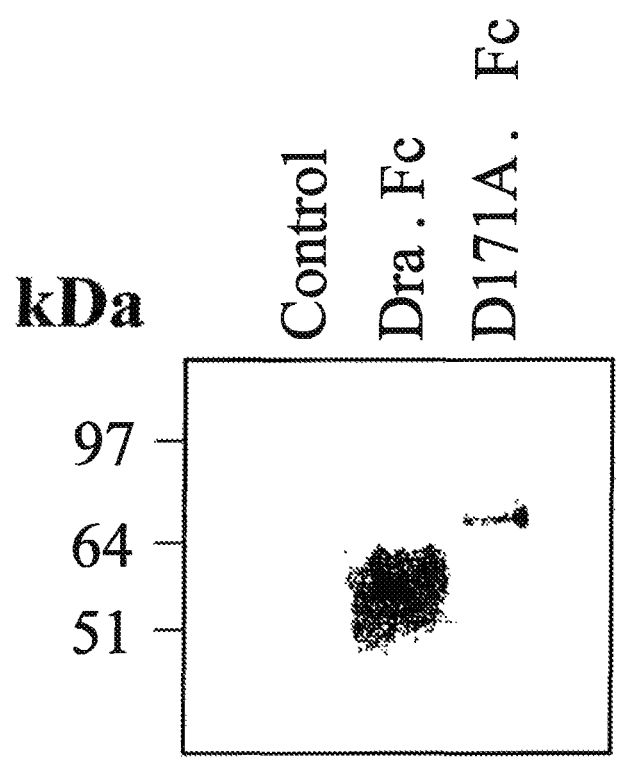
FIG. 14 is a gel showing that mouse Dragon-D171A.Fc fusion protein is not proteolytically cleaved compared to mouse Dragon.Fc fusion protein.

Similarly, mouse Dragon-D171A.Fc mutant cDNA was generated and expressed in HEK cell supernatants. The purified mutant protein obtained was shown to be stable to proteolytic cleavage compared to wild-type mouse Dragon.Fc protein (see FIG. 14).

In a third experiment, the human HJV-D172A mutant cDNA was generated and expressed in HEK cell supernatants. As shown on FIG. 15, in contrast to the wild-type human HJV protein, the mutant HJV protein did not undergo proteolytic cleavage.

Mutant HJV, RGMa, and Dragon fusion proteins that are more stable to proteolytic cleavage than the wild-type versions could be advantageously used in the methods of the present invention.

Example 5

Mutations in HFE2 Cause Iron Overload in Chromosome 1q-Linked Juvenile Hemochromatosis Juvenile hemochromatosis is an early-onset autosomal recessive disorder of iron overload resulting in cardiomyopathy, diabetes and hypogonadism that presents in the teens and early 20s (refs. 1,2). Juvenile hemochromatosis has previously been linked to the centromeric region of chromosome 1q (refs. 3-6), a region that is incomplete in the human genome assembly. Here we report the positional cloning of the locus associated with juvenile hemochromatosis and the identification of a new gene crucial to iron metabolism. We finely mapped the recombinant interval in families of Greek descent and identified multiple deleterious mutations in a transcription unit of previously unknown function (LOC 148738), now called HFE2, whose protein product we call hemojuvelin. Analysis of Greek, Canadian and French families indicated that one mutation, the amino acid substitution G320V, was observed in all three populations and accounted for two-thirds of the mutations found. HFE2 transcript expression was restricted to liver, heart and skeletal muscle, similar to that of hepcidin, a key protein implicated in iron metabolism[7-9]. Urinary hepcidin levels were depressed in individuals with juvenile hemochromatosis, suggesting that hemojuvelin is probably not the hepcidin receptor. Rather, HFE2 seems to modulate hepcidin expression.

Figure 16:
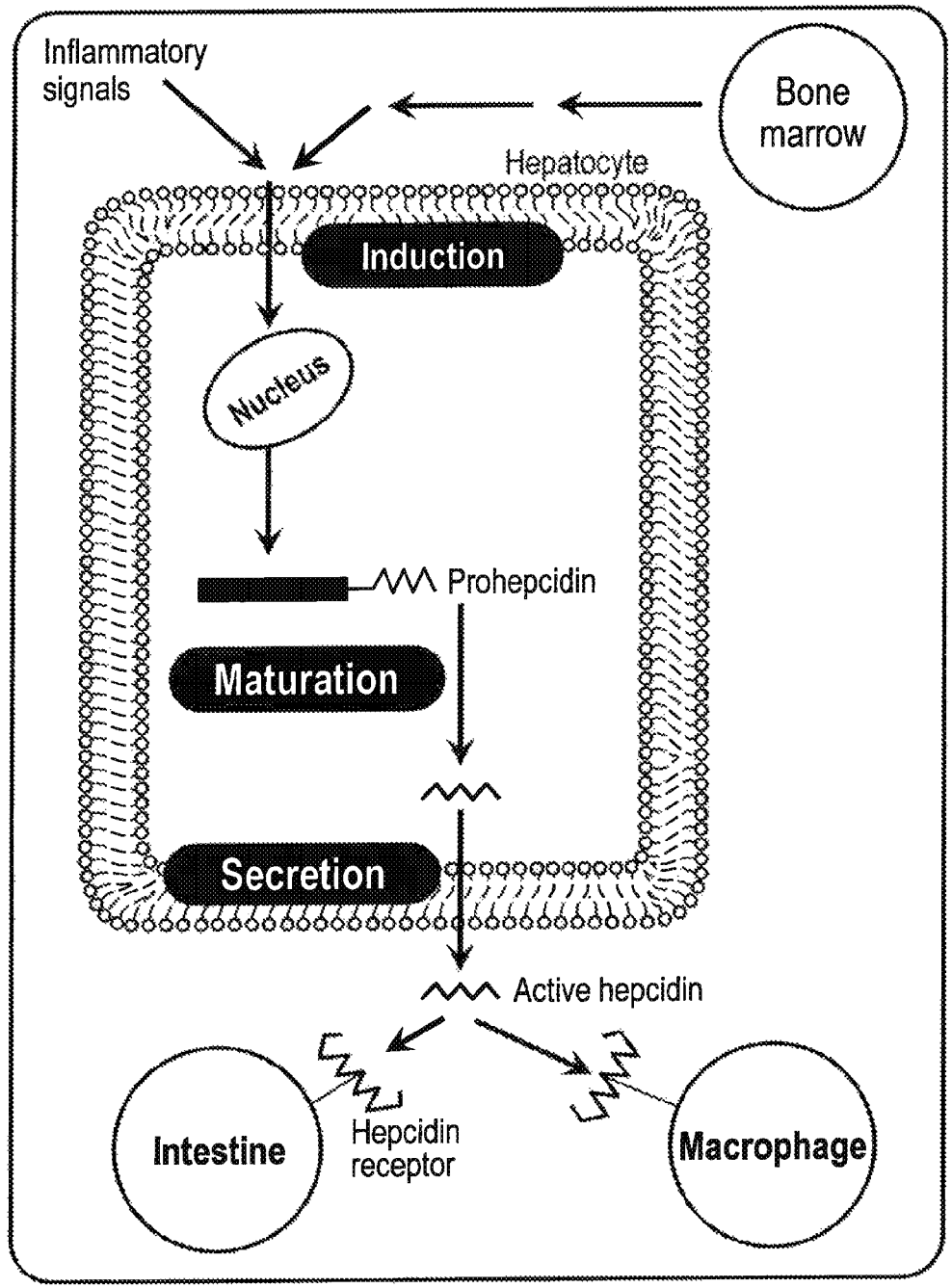
FIG. 16 shows a schematic describing how hepcidin modulates iron transport from enterocytes and macrophages. Hepcidin production is modulated by inflammatory signals, iron levels and signals from the bone marrow (erythroid drive). Hepcidin is initially produced as prohepcidin (84 amino acids), which is processed by cleavage to the putatively active form of 25 amino acids. Elevated levels of hepcidin prevent iron uptake from the intestine and iron release from macrophages.

Two families with juvenile hemochromatosis not linked to 1q were recently found to have loss-of-function mutations in the gene encoding hepcidin[10]. Hepcidin is a small peptide hormone predominantly secreted by the liver[11], whose levels correlate inversely with rates of iron uptake in the gut and with the release of iron from macrophages[12, 13] (FIG. 16). The clinical and biochemical phenotype of 1q-linked juvenile hemochromatosis is indistinguishable from that of hepcidin-deficient juvenile hemochromatosis, both having intestinal iron hyperabsorption leading to an early onset of severe iron overload associated with macrophages that do not load iron. This suggests that the more commonly mutated gene underlying 1q-linked juvenile hemochromatosis gene probably also functions in the hepcidin pathway.

To identify the gene associated with 1q-linked juvenile hemochromatosis, we collected samples from 12 unrelated families with juvenile hemochromatosis from Greece, Canada and France, 7 of whom were previously reported to be consistent with linkage to the juvenile hemochromatosis locus at 1q21 (HFE2; OMIM 602390). Only one family, JH7, is known to be consanguineous. Parents of all probands, where ascertained, were clinically and biochemically normal.

We verified absence of mutations of hepcidin in all 12 families and confirmed that juvenile hemochromatosis was consistent with linkage to 1q21 in these families by mapping a combination of publicly available markers and 18 new microsatellite markers identified from genomic sequence. Nine of the ten Greek families showed extended marker homozygosity in the 1q region (FIG. 17), consistent with linkage to a common gene as the chief determinant of juvenile hemochromatosis in this population. We reconstructed five different Greek haplotypes segregating in these families, one of which was observed repeatedly. Families JH4, JH8 and JH9 were each homozygous with respect to different haplotypes. The proband in family JH11 segregated alleles consistent with heterozygosity with respect to the common haplotype and a new haplotype.

We carried out multipoint linkage analysis to determine the statistical significance of the observed haplotype sharing and obtained a peak multipoint lod score of 4.05 in the shared segment for the Greek and Canadian families combined. The April 2003 genome sequence assembly (build 33) contains numerous gaps and duplications, but we were able to estimate the size of the linkage interval and define the linkage boundaries on the basis of existing sequence contigs. Recombinant events placed outer boundaries at CA3AL590452 and CA3AL359207.

We next embarked on a positional cloning effort. According to our interpretation of the genome assembly, the region of ~1.7 Mb associated with juvenile hemochromatosis contains 21 RefSeq annotated genes. In the course of sequencing these genes, we identified multiple mutations in one particular gene in the minimal recombinant interval (Table 1).

mutation. We detected six different mutations accounting for all 24 alleles in the ten Greek families, one Canadian family and one French family. None of the mutations was observed in over 500 control chromosomes. The mutations cosegregated completely with the juvenile hemochromatosis phenotype, and results of microsatellite-based haplotype analysis were consistent with recessive inheritance and full penetrance. We observed one common mutation, the G320V missense variant, in the seven Greek families who share the common Greek haplotype and in Canadian and French families.

Figure 18A:
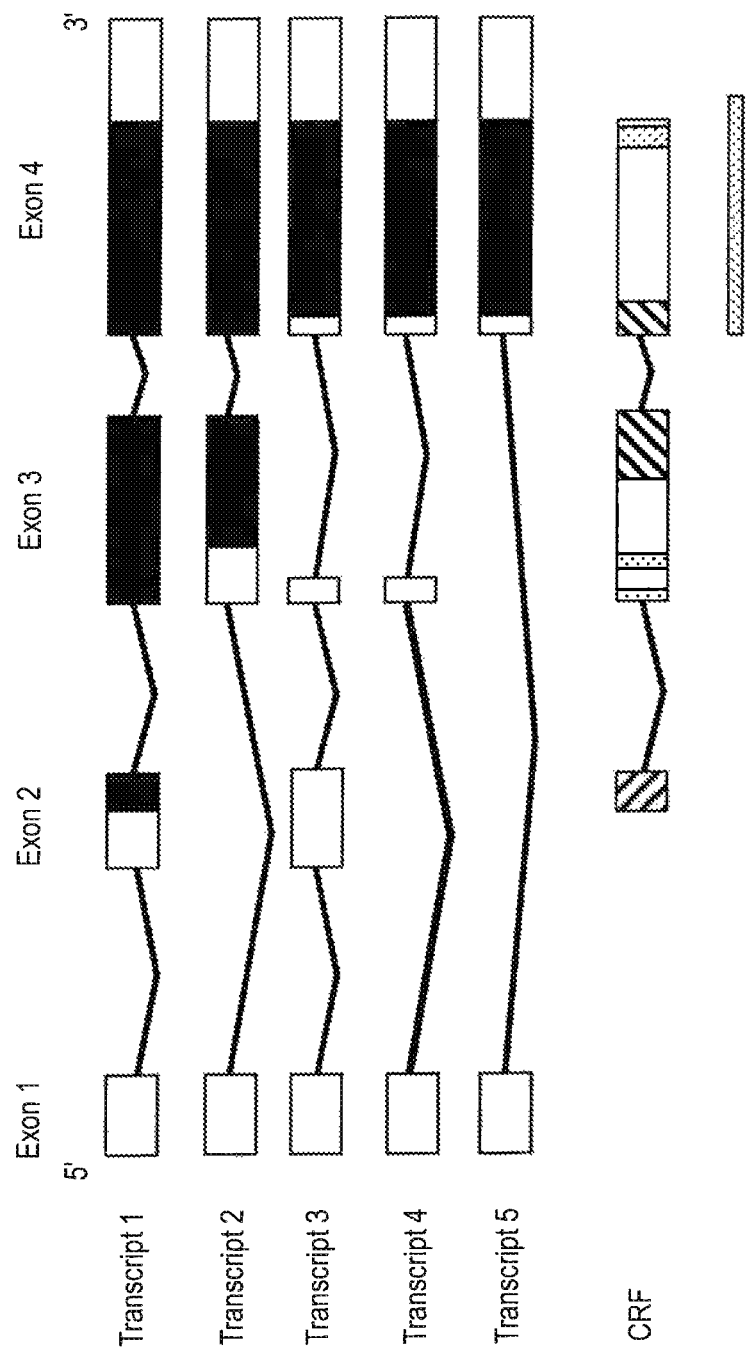
FIG. 18A shows a schematic displaying HFE2 gene structure and bioinformatics analysis. Transcript 1 was determined from sequencing a novel RT-PCR cDNA clone from human liver RNA. Alternatively spliced transcripts 2-5 were based on occurrence in EST or cDNA clones in public databases and RT-PCR experiments. Each of the five putative transcripts of HFE2 may be translated into a polypeptide. Transcripts 3, 4 and 5 generate the same protein; hence, there are three hemojuvelin isoforms of 426, 313 or 200 amino acids. Exon 2 was predicted in Ensembl for human HFE2 based on a rat cDNA clone containing this exon (incorrectly annotated as human but 100% identical with rat genomic sequence). Additional mouse ESTs, conservation of the exon in human genomic sequence and a novel human cDNA clone verified the coding region of transcript 1. Untranslated sequence is colored white, translated sequence black. Below the transcripts is shown a version of the longest open reading frame (ORF) with protein domains parsed across the exons and codon numbers given at splice junctions (SP, signal peptide; RGD, tri-amino acid motif; vWf, partial von Willebrandt factor; TM, transmembrane). Gray horizontal bar at bottom indicates northern-blot probe.
Figure 18B:
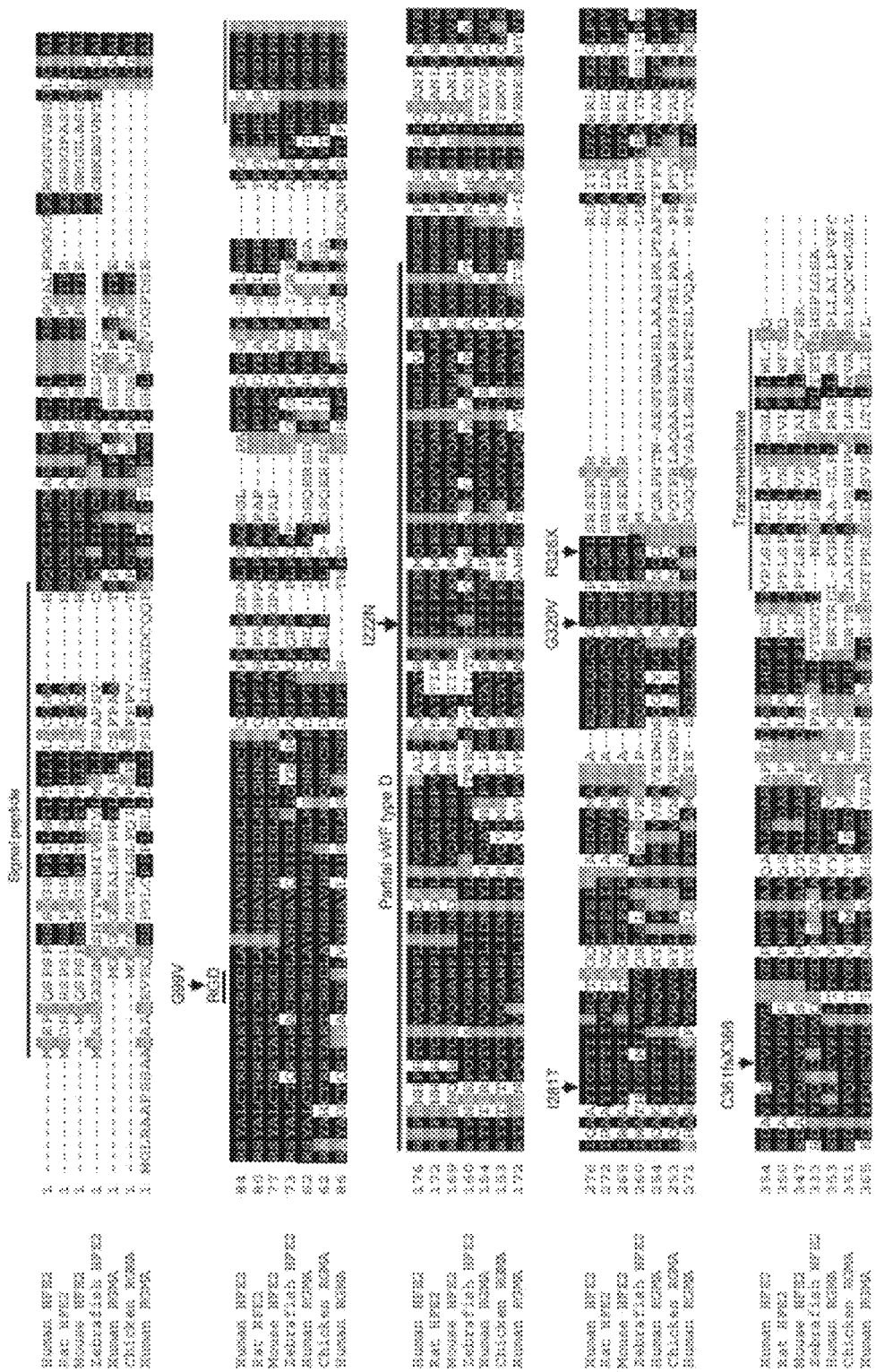
FIG. 18B shows a multiple sequence alignment of HFE2 (hemojuvelin) with orthologs of mouse, rat and zebrafish and paralogs of human and chicken. The longest cDNA sequence (transcript 1) and its predicted protein sequence were used as the basis for sequence numbering beginning from the putative initiating methionine. Above sequences, protein functional domains are shown as horizontal bars. Amino acid changes in individuals with juvenile hemochromatosis are indicated by arrows.

We predict that hemojuvelin is transcribed from a gene of 4,265 bp into a full-length transcript with five spliced isoforms (FIG. 18a). The putative full-length protein from the longest transcript (transcript 1) is 426 amino acids; the occurrence of this transcript in humans has been confirmed experimentally by RT-PCR and sequencing of a novel cDNA clone. Hemojuvelin contains multiple protein motifs (FIG. 18a) consistent with a function as a membrane-bound receptor or secreted polypeptide hormone. Orthologs of human hemojuvelin are found in mouse, rat and zebrafish (FIG. 18b). Sequence comparison shows that human hemojuvelin is

TABLE 1

Genetic and clinical information of families with mutations in HFE2

| Individual | Origin | Number of affected individuals in family | Age at onset | Age at diagnosis | Serum ferritin ($\mu g\, I^{-1}$) | Transferrin saturation (%) | Hypogonadism | Arthropathy |
|---|---|---|---|---|---|---|---|---|
| JH1-301 | Canada | 3 | 7 | 7 | 339 | 94 | − | − |
| JH3-201 | Greece | 1 | 21 | 25 | 2,283 | 100 | + | + |
| JH4-203 | Greece | 1 | 39 | 49 | 4,127 | 90 | + | + |
| JH5-201 | Greece | 2 | 32 | 39 | 3,553 | 100 | | |
| JH6-205 | Greece | 2 | 25 | 32 | 2,500 | 100 | + | + |
| JH7-201 | Greece | 3 | 20 | 21 | NA | 100 | + | − |
| JH8-202 | Greece | 1 | 26 | 33 | 5,900 | 98 | + | − |
| JH9-201 | Greece | 2 | 28 | 33 | 1,125 | 80 | + | + |
| JH10-201 | Greece | 1 | 21 | 25 | 5,250 | 100 | + | − |
| JH11-201 | Greece | 1 | 33 | 37 | 731 | 100 | − | − |
| JH12-201 | Greece | 1 | 29 | 31 | 2,254 | 100 | + | − |
| JH13-301 | France | 1 | 16 | 23 | 7,125 | 83 | + | + |

| Individual | Skin pigmentation | Glucose intolerance | Heart disease | Hepatic fibrosis | Mutation status | Effect on coding sequence |
|---|---|---|---|---|---|---|
| JH1-301 | + | − | − | + | Compound heterozygous | I222N, G320V |
| JH3-201 | + | − | − | + | Homozygous | G320V |
| JH4-203 | + | − | − | + | Homozygous | I281T |
| JH5-201 | | | | | Homozygous | G320V |
| JH6-205 | + | + | + | + | Homozygous | G320V |
| JH7-201 | + | − | − | NA | Homozygous | G320V |
| JH8-202 | + | − | − | + | Homozygous | C361fsX366 |
| JH9-201 | − | + | − | + | Homozygous | G99V |
| JH10-201 | − | − | − | + | Homozygous | G320V |
| JH11-201 | + | − | − | − | Compound heterozygous | G320V, R326X |
| JH12-201 | − | − | − | NA | Homozygous | G320V |
| JH13-301 | + | + | + | + | Homozygous | G320V |

+, present;
−, absent:
NA, information not available.

This gene corresponds to anonymous transcript LOC148738 in RefSeq, although we predicted a slightly more complex gene structure from available cDNA and expressed-sequence tag (EST) evidence (FIG. 18a). The observed mutations include four missense mutations in residues that are highly conserved in evolution (Table 1 and FIG. 18b), a premature termination mutation and a frameshift >85% identical to the mammalian orthologs and ~45% identical to the fish ortholog. The hemojuvelin isoform of 426 amino acids also shares considerable sequence similarity with the repulsive guidance molecule 14 (RGM or RGMA) of human (48% identity) and chicken (46% identity; FIG. 18b). In humans there is a third RGM-like protein, RGMB, whose biological function is currently unknown.

Figure 19:
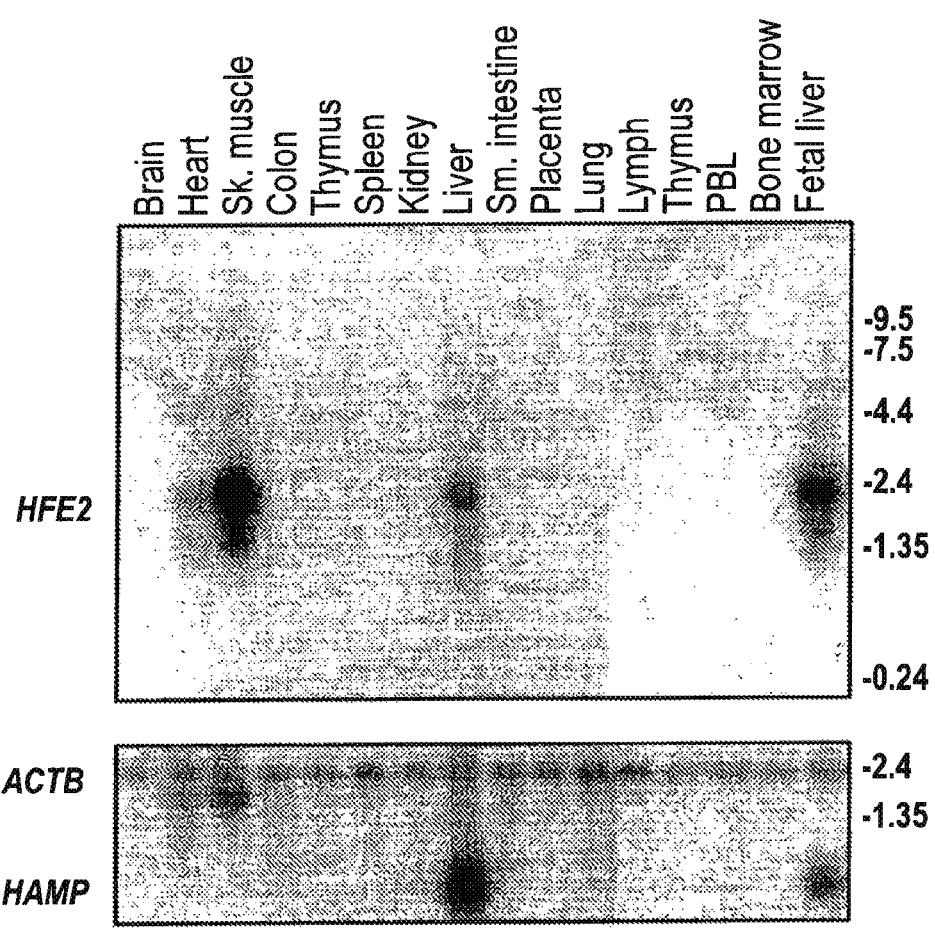
FIG. 19 shows a northern blot displaying tissue expression of hemojuvelin. Northern blots of human tissues were probed with sequences encompassing exon 4 of HFE2 and then reprobed with probes for hepcidin (HAMP) and β-actin (ACTB). The ACTB probe highlights a second isoform specific to skeletal muscle and heart, in addition to the ubiquitous transcript in these tissues. Sizes are relative to lane standards. PBL, peripheral blood lymphocytes.

We examined HFE2 expression in 16 human tissue types by probing northern blots with a probe from exon 4 and detected substantial expression in adult and fetal liver, heart and skeletal muscle (FIG. 19). The primary RNA observed in these tissues migrated at about 2.2 kb, consistent with full-length transcript 1 in FIG. 18a. After reprobing the same blots for hepcidin, we detected strong expression in adult and fetal liver only. We later detected expression of hepcidin in a heart-specific northern blot.

Figure 20:
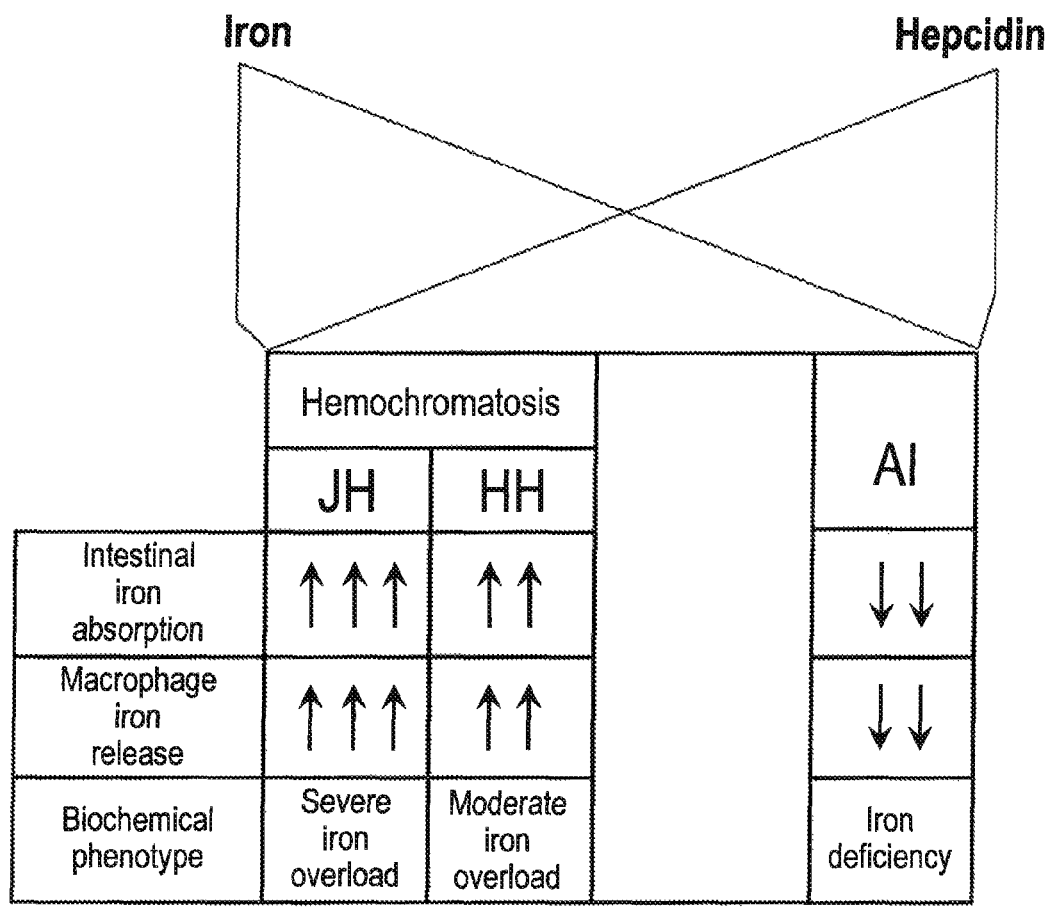
FIG. 20 shows a schematic summarizing that anemia of inflammation and hemochromatosis represent opposite ends of the phenotypic spectrum of iron-related disorders. Anemia of inflammation (AI) is characterized by high levels of hepcidin, which leads to iron deficiency and iron-rich macrophages. In contrast, in hemochromatosis, hepcidin levels are low with enhanced intestinal absorption and whole-body iron overload. Macrophages in hemochromatosis are iron-depleted. Juvenile hemochromatosis (JH) and adult-onset hereditary hemochromatosis (HH) both show iron overload with iron-depleted macrophages, but the phenotype is more severe in juvenile hemochromatosis.

We measured hepcidin peptide levels in urine samples from a subset of Greek individuals with juvenile hemochromatosis. Deleterious mutations of hemojuvelin reduce hepcidin levels despite iron overload, which normally induces hepcidin expression[15]. Hepcidin levels were consistently depressed in the individuals with juvenile hemochromatosis: homozygous affected individuals from five different families had 5-11 ng mg$^{-1}$ creatinine compared with 14-165 ng mg$^{-1}$ creatinine in four heterozygous unaffected carriers and 10-100 ng mg$^{-1}$ creatinine in unrelated controls. In one individual who did not have hemochromatosis who had an infection at the time of measurement, urine hepcidin level was very high (1,024 ng mg$^{-1}$ creatinine), as expected. These results suggest that HFE2 acts as a modulator of hepcidin expression, although it is not possible to distinguish a pretranscriptional from a post-transcriptional or even post-translational role for HFE2 in the absence of liver biopsies to measure hepcidin mRNA levels. In adult-onset hereditary hemochromatosis[16] and Hfe knockout mice[17, 18], hepcidin levels are inappropriately low for the degree of iron overload. Thus, we believe that juvenile hemochromatosis and adult-onset hereditary hemochromatosis are on the same biochemical and phenotypic spectrum, with juvenile hemochromatosis representing the more severe, earlier-onset phenotype with absent (or very low) hepcidin, and adult-onset hemochromatosis manifesting later in life with only partial deficiency for hepcidin[18] (FIG. 20). The direct result of this hepcidin deficiency is that in both adult-onset hemochromatosis and juvenile hemochromatosis there is intestinal iron hyperabsorption. The excessive iron uptake in juvenile hemochromatosis is greater than that seen in adult-onset hereditary hemochromatosis, reflecting the lower levels of hepcidin associated with juvenile hemochromatosis and culminating in an earlier onset of a more acute phenotype.

Loss of function of hepcidin in mice also leads to severe iron overload, mimicking the biochemical and clinical phenotype of juvenile hemochromatosis[8]. In contrast, in both other animal models[19] and human diseases[20], overexpression of hepcidin leads to macrophage iron retention and an iron-deficient phenotype typical of the iron disturbances found in anemia of inflammation (also called anemia of chronic disease)[21]. Anemia of inflammation is an acquired disorder, seen in individuals with various conditions including infection, malignancy and chronic inflanunation[22]. It is characterized by a retention of iron by macrophages and decreased intestinal iron absorption, which leads to reduced iron availability for erythropoesis[21, 23].

Consistent with the proposed role of hepcidin in the pathogenesis of anemia of inflammation, the defects in iron absorption and reuse in anemia of inflammation are accompanied by elevated urinary (and presumably serum) hepcidin levels. Existing therapy for anemia of inflammation is mainly targeted to treating the underlying disorder, with no efficacious treatment specifically directed to amelioration of the iron deficiency. Therapeutics that mimic the juvenile hemochromatosis phenotype (hepcidin deficiency) will serve to reduce hepcidin levels and thereby treat the opposite phenotype of anemia of inflammation (hepcidin excess). Thus, hemojuvelin represents a new therapeutic target for the treatment of anemia of inflammation.

Recent reports that adult-onset hereditary hemochromatosis can result from digenic inheritance with compound heterozygosity with respect to HFE and HAMP (encoding hepcidin) and that mutations in HAMP can contribute to the severity of adult-onset hereditary hemochromatosis24 suggest that modulation of other genes in the hepcidin pathway may also predispose to the adult phenotype. Therefore, we are currently exploring the role of hemojuvelin in modulating the onset and severity of adult-onset hemochromatosis. The identification of hemojuvelin presents new therapeutic and diagnostic opportunities for the management of iron-related disorders.

Methods

Selection of study subjects. All samples used in this study were collected with informed consent and approved for study by institutional review boards and ethics committees at all affiliated institutions. Families JH3-JH7 were previously reported[5] as families 1-5, respectively; families JH8 and JH9 were also previously reported[4] as families 1 and 2, respectively. Diagnoses of affected individuals in these families were previously reported[4, 25]. We diagnosed additional probands with juvenile hemochromatosis based on early presentation with disease-related clinical complications, including hypogonadotrophic hypogonadism, heart disease and skin pigmentation, along with testing of transferrin saturation, serum ferritin levels and hepatic siderosis (Table 1). Families JH11 and JH13 consist of individual probands. Families JH3, JH4 and JH5 originated in a small area in southwestern Greece; families JH6 and JH7 originated in a mountain area of central Greece; and family JH10 originated from northwestern and northeastern Greece (maternal and paternal sides, respectively). Families JH8, JH9, JH11 and JH12 also live in Greece, and family JH13 lives in France. Family JH1 lives in Canada and is of European origin. Consanguinity has been documented only in family JH7 (marriage between first cousins). Control DNAs included at least 90 DNAs from each of three different sources: Greek, northern European and the Coriell polymorphism discovery resource containing multiple ethnicities.

Markers and genotyping. We used commercially available markers (ABI) for genotyping in the 1q21 interval. We designed an additional 18 custom markers using existing sequence obtained from GenBank for fine-mapping. We carried out radiation hybrid mapping on selected microsatellite markers or other sequence-tagged sites using the TNG hybrid panel (Research Genetics) to resolve contig order. We carried out genotyping on an Applied Biosystems PRISM® 3100 Genetic Analyzer running GENEMAPPER® software. We verified mendelian inheritance of alleles for all markers using the PedCheck program26.

Linkage and haplotype analysis. We estimated allele frequencies from 16 untransmitted haplotypes from the ten Greek pedigrees and from 40 genotyped control Greek individuals. We carried out multipoint linkage analysis with Genehunter using an inheritance model with 0.99 penetrance, 0.000005 phenocopy rate and a recessive disease allele frequency of 0.01. We determined haplotypes using Genehunter.

Mutation detection. We designed primers to amplify coding sequences for genes present in the defined 1q interval. The process of primer design involved the identification of candidate genes and their respective exons in Ensembl, automated primer design for the exons using Primer3 and validation of the primers using e-PCR. We amplified PCR products using standard PCR conditions with QIAGEN™ Taq polymerase on a Peltier Thermal Cycler (MJ Research, PTC-225). We treated PCR products with 4 units exonuclease and 4 units shrimp alkaline phosphatase for 2-16 h and used 5 µl for sequencing. We carried out sequencing using BIGDYE® Terminator on an ABI 3700 sequencer (ABI) and sequence analysis and mutation detection using the Phred/Phrap/Consed/Polyphred[27,28] or SEQUENCHER® software suites. We designed additional primers to amplify and sequence all published and predicted exons of LOC148738, including the 5' and 3' untranslated regions and the 500-bp presumptive sequence upstream of the first exon. All primer sequences are available on request.

Northern-blot analysis. We purchased Clontech northern blots and probed them with 32P-labeled probes. We generated substrates for probes from purified, PCR-amplified products from genomic DNA for LOC148738 and HAMP and from manufacturer's supplied reagents for actin according to manufacturer's instructions. RNA for RT-PCR was either purchased from Clontech or Biochain or prepared from tissues using the QIAGEN™ RNeasy Protect Midi kit. We prepared single-strand cDNA using the INVITROGEN™ SUPERSCRIPT® First-Strand Synthesis for RT-PCR kit according to the manufacturer's instructions.

Bioinformatics. We carried out all pairwise sequence comparisons using BLAST 2 Sequences29 with the following parameters: program, blastp; matrix, BLOSUM62; open gap penalty, 11; extension gap penalty, 1; gap_x_dropoff, 50; word size, 3; expect, 10. We aligned sequences using ClustalX.

We identified orthologs of human hemojuvelin in mouse (although protein coding potential annotated in the database does not correspond to full-length open reading frame of the actual sequence), rat and zebrafish (identified by a sequence similarity search of genes predicted by Genscan, gene structure based on genomic sequence traces and supporting ESTs). We identified paralogs of hemojuvelin in human (RGM or RGMA, RGMB) and chicken (RGM) from Blast comparison to GenBank.

Urinary hepcidin assay. Urinary creatinine concentrations were measured by UCLA Clinical Laboratories. Cationic peptides were extracted from urine using CM Macroprep (BIORAD™), eluted with 5% acetic acid, lyophilized and resuspended in 0.01% acetic acid. Urinary hepcidin concentrations were determined by immunodot assay. Briefly, we analyzed urine extracts equivalent to 0.1-4 mg of creatinine along with 0.6-40 ng hepcidin standards on dot blots on IMMOBILON™-P membrane (Millipore). We detected hepcidin on the blots using rabbit antibody to human hepcidin[15] with goat antibody to rabbit horseradish peroxidase as second antibody. We developed the blots by the chemiluminescent detection method (SuperSignal West Pico Chemiluminescent Substrate, Pierce) and quantified them with the Chemidoc cooled camera running Quantity One software (BIORAD™). Using this assay, we determined the normal range of urinary hepcidin to be 10-100 ng per mg creatinine (data not shown).

GenBank accession numbers. Translated portion of HFE2 transcript 1, based on a novel sequenced cDNA clone, AY372521; predicted human HFE2 transcripts 1-5, BK001575-BK001578 and BC017926, respectively; predicted zebrafish HFE2 translated portion, BK001579. The mouse HFE2 ortholog sequence was inferred with modifications from NM_027126; rat HFE2 ortholog was inferred with modifications from AK098165 (annotated as human but identified as rat by comparison with genomic sequences); zebrafish HFE2 was inferred with modifications from A1437181 and BG985666.

References

1. De Gobbi, M. et al. Natural history of juvenile haemochromatosis. Br. J. Haematol. 117, 973-979 (2002).
2. Camasehella, C., Roetto, A. & De Gobbi, M. Juvenile hemochromatosis. Semin. Hematol. 39, 242-248 (2002).
3. Roetto, A. et al. Juvenile hemochromatosis locus maps to chromosome 1q. Am. J. Hum. Genet. 64, 1388-1393 (1999).
4. Papanikolaou, G. et al. Genetic heterogeneity underlies juvenile hemochromatosis phenotype: analysis of three families of northern greek origin. Blood Cells Mol. Dis. 29, 168-173 (2002).
5. Papanikolaou, G. et al. Linkage to chromosome 1q in Greek families with juvenile hemochromatosis. Blood Cells Mol. Dis. 27, 744-749 (2001).
6. Rivard, S. R. et al. Juvenile hemochromatosis locus maps to chromosome 1q in a French Canadian population. Eur. J. Hum. Genet. 11, 585-589 (2003).
7. Pigeon, C. et al. A new mouse liver-specific gene, encoding a protein homologous to human antimicrobial peptide hepcidin, is overexpressed during iron overload. J. Biol. Chem. 276, 7811-7819 (2001).
8. Nicolas, G. et al. Lack of hepcidin gene expression and severe tissue iron overload in upstream stimulatory factor 2 (USF2) knockout mice. Proc. Natl. Acad. Sci. USA 98, 8780-8785 (2001).
9. Nicolas, G. et al. Hepcidin, a new iron regulatory peptide. Blood Cells Mol. Dis. 29, 327-335 (2002).
10. Roetto, A. et al. Mutant antimicrobial peptide hepcidin is associated with severe juvenile hemochromatosis. Nat. Genet. 33, 21-22 (2003).
11. Park, C. H., Valore, E. V., Waring, A. J. & Ganz, T. Hepcidin, a urinary antimicrobial peptide synthesized in the liver. J. Biol. Chem. 276, 7806-7810 (2001).
12. Fleming, R. E. & Sly, W. S. Hepcidin: a putative iron-regulatory hormone relevant to hereditary hemochromatosis and the anemia of chronic disease. Proc. Natl. Acad. Sci. USA 98, 8160-8162 (2001).
13. Ganz, T. Hepcidin, a key regulator of iron metabolism and mediator of anemia of inflammation. Blood 102, 783-788 (2003).
14. Monnier, P. P. et al. RGM is a repulsive guidance molecule for retinal axons. Nature 419, 392-395 (2002).
15. Nemeth, E. et al. Hepcidin, a putative mediator of anemia of inflammation, is a type II acute-phase protein. Blood 101, 2461-2463 (2003).
16. Bridle, K. R. et al. Disrupted hepcidin regulation in HFE-associated haemochromatosis and the liver as a regulator of body iron homoeostasis. Lancet 361, 669-673 (2003).
17. Ahmad, K. A. et al. Decreased liver hepcidin expression in the hfe knockout mouse. Blood Cells Mol. Dis. 29, 361-366 (2002).
18. Muckenthaler, M. et al. Regulatory defects in liver and intestine implicate abnormal hepcidin and Cybrd1 expression in mouse hemochromatosis. Nat. Genet. 34, 102-107 (2003).
19. Nicolas, G. et al. Severe iron deficiency anemia in transgenic mice expressing liver hepcidin. Proc. Natl. Acad. Sci. USA 99, 4596-4601 (2002).
20. Weinstein, D. A. et al. Inappropriate expression of hepcidin is associated with iron refractory anemia: implications for the anemia of chronic disease. Blood 100, 3776-3781 (2002).
21. Roy, C. N., Weinstein, D. A. & Andrews, N. C. 2002 E. Mead Johnson Award for Research in Pediatrics Lecture: the molecular biology of the anemia of chronic disease: a hypothesis. Pediatr. Res. 53, 507-512 (2003).
22. Means, R. T. Jr. The anaemia of infection. Baillieres Best Pract. Res. Clin. Haematol. 13, 151-162 (2000).

23. Weiss, G. Pathogenesis and treatment of anaemia of chronic disease. Blood Rev. 16, 87-96 (2002).

24. Merryweather-Clarke, A. T. et al. Digenic inheritance of mutations in HAMP and FIFE results in different types of haemochromatosis. Hum. Mol. Genet. 12, 2241-2247 (2003).

25. Papanikolaou, G. et al. Hereditary hemochromatosis: HFE mutation analysis in Greeks reveals genetic heterogeneity. Blood Cells Mol. Dis. 26, 163-168 (2000).

26. O'Connell, J. R. & Weeks, D. E. PedCheck: a program for identification of genotype incompatibilities in linkage analysis. Am. J. Hum. Genet. 63, 259-266 (1998).

27. Nickerson, D. A., Tobe, V. O. & Taylor, S. L. PolyPhred: automating the detection and genotyping of single nucleotide substitutions using fluorescence-based resequencing. Nucleic Acids Res. 25, 2745-2751 (1997).

28. Ewing, B., Hillier, L., Wendl, M. C. & Green, P. Base-calling of automated sequencer traces using phred. I. Accuracy assessment. Genome Res. 8, 175-185 (1998).

29. Tatusova, T. A. & Madden, T. L. BLAST 2 Sequences, a new tool for comparing protein and nucleotide sequences. FEMS Microbiol. Lett. 174, 247-250 (1999).

Figure 15:
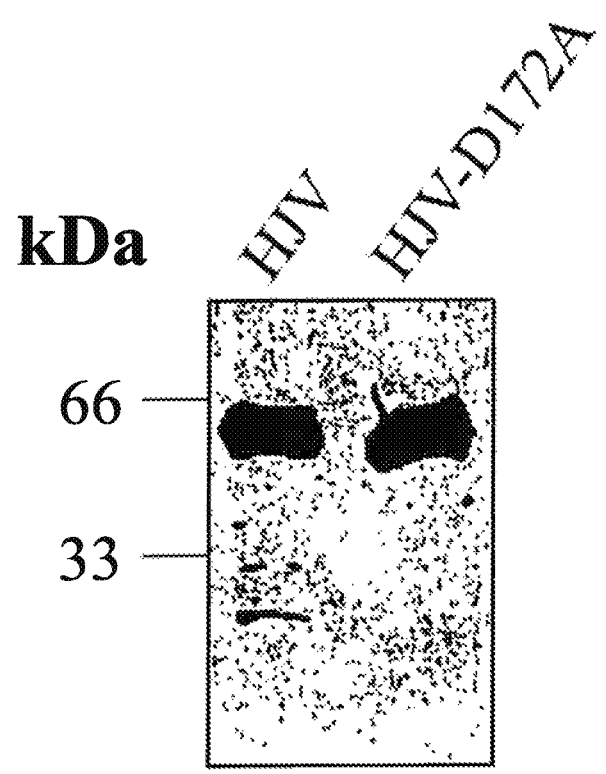
FIG. 15 is a gel showing that human HJV-D172A is not proteolytically cleaved compared to human HJV.

Please insert new FIGS. 16-20 after FIG. 15 in the specification.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A composition comprising a fusion protein comprising a polypeptide comprising an amino acid sequence at least 94% identical to SEQ ID NO:24, wherein the polypeptide is fused to Fc.

2. The composition of claim 1, wherein the Fc is human Fc.

3. The composition of claim 1, wherein the Fc is IgG Fc.

4. The composition of claim 1, wherein the polypeptide comprises an amino acid sequence at least 99% identical to SEQ ID NO:24.

5. A pharmaceutical composition comprising the fusion protein of claim 4 and a pharmaceutically acceptable carrier.

6. A pharmaceutical composition comprising the fusion protein of claim 1 and a pharmaceutically acceptable carrier.

7. A composition comprising a fusion protein comprising a polypeptide comprising an amino acid sequence at least 94% identical to amino acids 1-400 of SEQ ID NO:24, wherein the polypeptide is fused to Fc.

8. The composition of claim 7, wherein the polypeptide comprises an amino acid sequence at least 99% identical to amino acids 1-400 of SEQ ID NO:24.

9. A pharmaceutical composition comprising the fusion protein of claim 8 and a pharmaceutically acceptable carrier.

10. A pharmaceutical composition comprising the fusion protein of claim 7 and a pharmaceutically acceptable carrier.

11. The composition of claim 7, wherein the Fc is human Fc.

12. The composition of claim 7, wherein the Fc is IgG Fc.

13. A composition comprising a fusion protein comprising a polypeptide comprising an amino acid sequence at least 94% identical to amino acids 35-400 of SEQ ID NO:24, wherein the polypeptide is fused to Fc.

14. The composition of claim 13, wherein the polypeptide comprises an amino acid sequence at least 99% identical to amino acids 35-400 of SEQ ID NO:24.

15. A pharmaceutical composition comprising the fusion protein of claim 14 and a pharmaceutically acceptable carrier.

16. A pharmaceutical composition comprising the fusion protein of claim 13 and a pharmaceutically acceptable carrier.

17. The composition of claim 13, wherein the Fc is human Fc.

18. The composition of claim 13, wherein the Fc is IgG Fc.

* * * * *

UNITED STATES PATENT AND TRADEMARK OFFICE
CERTIFICATE OF CORRECTION

PATENT NO. : 8,637,023 B2
APPLICATION NO. : 13/407502
DATED : January 28, 2014
INVENTOR(S) : Herbert Y. Lin et al.

Page 1 of 1

It is certified that error appears in the above-identified patent and that said Letters Patent is hereby corrected as shown below:

In the Specification

Please insert the following section after the section of "CROSS-REFERENCE TO RELATED APPLICATIONS":

--STATEMENT REGARDING FEDERALLY SPONSORED RESEARCH OR DEVELOPMENT

This invention was made with Government support under Grant No(s). DK002716 awarded by the National Institutes of Health. The Government has certain rights in this invention.--

Signed and Sealed this
Fifteenth Day of July, 2014

Michelle K. Lee
*Deputy Director of the United States Patent and Trademark Office*